US009243293B2

(12) United States Patent
Holsboer et al.

(10) Patent No.: US 9,243,293 B2
(45) Date of Patent: Jan. 26, 2016

(54) GENES ASSOCIATED WITH POSTTRAUMATIC-STRESS DISORDER (PTSD)

(75) Inventors: Florian Holsboer, Munich (DE); Marcus Ising, Munich (DE); Rachel Yehuda, Bronx, NY (US); Joseph D. Buxbaum, New York, NY (US)

(73) Assignee: MAX-PLANCK-GESELLSCHAFT ZUR FORDERUNG DER WISSENSCHAFTEN E.V., Munich (DE)

( * ) Notice: Subject to any disclaimer, the term of this patent is extended or adjusted under 35 U.S.C. 154(b) by 270 days.

(21) Appl. No.: 13/063,696

(22) PCT Filed: Sep. 14, 2009

(86) PCT No.: PCT/EP2009/061890

§ 371 (c)(1), (2), (4) Date: May 23, 2011

(87) PCT Pub. No.: WO2010/029176

PCT Pub. Date: Mar. 18, 2010

(65) Prior Publication Data

US 2012/0039812 A1 Feb. 16, 2012

(30) Foreign Application Priority Data

Sep. 12, 2008 (EP) .................................. 08016126.8
Sep. 14, 2009 (WO) ................. PCT/EP2009/061890

(51) Int. Cl.
*C12Q 1/68* (2006.01)
*C12P 19/34* (2006.01)
*C07H 21/02* (2006.01)

(52) U.S. Cl.
CPC ........ *C12Q 1/6883* (2013.01); *C12Q 2600/136* (2013.01); *C12Q 2600/158* (2013.01)

(58) Field of Classification Search
CPC ........... C12Q 1/6883; C12Q 2600/136; C12Q 2600/158
See application file for complete search history.

(56) References Cited

U.S. PATENT DOCUMENTS

| | | | |
|---|---|---|---|
| 4,946,778 | A | 8/1990 | Ladner et al. |
| 6,080,560 | A | 6/2000 | Russell et al. |
| 2005/0084880 | A1 | 4/2005 | Duman et al. |
| 2005/0176057 | A1 | 8/2005 | Bremer et al. |

FOREIGN PATENT DOCUMENTS

WO 2006/013561 A2 2/2006

OTHER PUBLICATIONS

GenBank Locus: NM_004117 '*Homo sapiens* FK506 binding protein 5 (FKBP5), mRNA' Sep. 3, 2007, from www.ncbi.nlm.nih.gov, pp. 1-7.*

Binder E.B. et al. JAMA, Mar. 19, 2008, vol. 299, No. 11, pp. 1291-1305.*

Segman R.H. et al. Molecular Psychiatry (2005) 10, 500-513.*

Cheung V.G. et al. Nature Genetics, vol. 33, Mar. 2003, p. 422-425.*

Chen G. et al. Molecular & Cellular Proteomics 1.4 (2002) pp. 304-313.*

Enard W. et al. Science (2002) vol. 296, pp. 340-343.*

Cobb J.P. et al. Crit Care Med 2002 vol. 30, No. 12, pp. 2711-2721.*

Patsch et al., Conditional Mutagenesis by Cell-Permeable Proteins: Potential, Limitations and Prospects, Handbook of Experimental Pharmacology, 2007, 203-232, 178.

Perkonigg et al., Longitudinal Course of Posttraumatic Stress Disorder and Posttraumatic Stress Disorder Symptoms in a Community Sample of Adolescents and Young Adults, Am. J. Psychiatry, 2005, 1320-1327, 162(7).

Pitman et al., Twenty-four hour urinary cortisol and catecholamine excretion in combat-related posttraumatic stress disorder, Biol. Psychiatry, 1990, 245-247, 27(2).

Ribeiro et al., The DST as a predictor of outcome in depression: a meta-analysis, Am. J. Psychiatry, 1993, 1618-1629, 150(11).

Rose et al., Three-Dimensional Structures of HIV-1 and SIV Protease Product Complexes, Biochemistry, 1996, 12933-12944, 35(39).

Rutenber, A New Class of HIV-1 Protease Inhibitor: The Crystallographic Structure, Inhibition and Chemical Synthesis of an Aminimide Peptide Isostere, Bioorg. Med. Chem., 1996, 1545-1558, 4(9).

Saiki et al., Primer-Directed Enzymatic Amplification of DNA with a Thermostable DNA Polymerase, Science, 1988, 487-491, 239(4839).

Schier, Efficient in vitro affinity maturation of phage antibodies using BIAcore guided selections, Hum. Antibod. Hybridomas, 1996, 97-105, 7(3).

Spector et al. (Eds.), Cells: A Laboratory Manual, 1997, vols. 1-3, Cold Spring Harbor Laboratory Press (Table of Contents).

Stein et al., Genetic and Environmental Influences on Trauma Exposure and Posttraumatic Stress Disorder Symptoms: A Twin Study, Am. J. Psychiatry, 2002, 1675-1681, 159(1).

Su et al., Dysregulated Mitochondrial Genes and Networks with Drug Targets in Postmortem Brain of Patients with Posttraumatic Stress Disorder (PTSD) Revealed by Human Mitochondria-Focused cDNA Microarrays, Int. J. Biol Sci., 2008, 223-235, 4(4).

True et al., Twin Study of Genetic and Environmental Contributions to Liability for Posttraumatic Stress Symptoms, Arch. Gen. Psychiatry, 1993, 257-264, 50(4).

Turck et al., Proteomic strategies for biomarker discovery—from differential expression to isoforms to pathways, in Turck (Ed.), Biomarkers for Psychiatric Disorders, 2008, 57-74, Ch. 3, Springer, NY.

Velculescu et al., Serial Analysis of Gene Expression, Science, 1995, 484-487, 270(5235).

(Continued)

*Primary Examiner* — Stephen Kapushoc
(74) *Attorney, Agent, or Firm* — Roberts Mlotkowski Safran & Cole, P.C.

(57) ABSTRACT

The present invention relates to a method of identifying a predisposition for developing posttraumatic stress disorder (PTSD) in a subject comprising assessing in a sample obtained from said subject the expression level of one or more genes selected from the FK506 binding protein 5 (FKBP5) gene, the signal transducer and activator of transcription (STAT5B) gene and the nuclear factor I/A (NFIA) gene, wherein a decrease in the expression level of said one or more genes as compared to the expression level of the corresponding gene(s) of a control is indicative of a predisposition for developing PTSD. Further, the invention relates to a method of identifying a compound capable of preventing or treating PTSD or capable of serving as a lead compound for developing a compound capable of preventing or treating PTSD and also to a method of selecting a therapy to prevent or treat PTSD.

15 Claims, 1 Drawing Sheet

(56) References Cited

OTHER PUBLICATIONS

Wodak, Computer-Aided Design in Protein Engineering, Ann. NY Acad. Sci., 1987, 1-13, 501.
Xian et al., Genetic and environmental influences on posttraumatic stress disorder, alcohol and drug dependence in twin pairs, Drug Alcohol Depend., 2000, 95-102, 61(1).
Yehuda, Post-Traumatic Stress Disorder, N. Engl. J. Med., 2002, 108-114, 346(2).
Yehuda et al., Cortisol regulation in posttraumatic stress disorder and major depression: A chronobiological analysis, Biol. Psychiatry, 1996, 79-88, 40(2).
Yehuda et al., Circadian Rhythm of Salivary Cortisol in Holocaust Survivors With and Without PTSD, Am. J. Psychiatry, 2005, 998-1000, 162(5).
Yehuda et al., Transgenerational Effects of Posttraumatic Stress Disorder in Babies of Mothers Exposed to the World Trade Center Attacks during Pregnancy, J. Clin. Endocrinol. Metab., 2005, 4115-4118, 90(7).
Yehuda et al., Response Variation following Trauma: A Translational Neuroscience Approach to Understanding PTSD, Neuron, 2007, 19-32, 56(1).
Yehuda et al., Transgenerational transmission of cortisol and PTSD risk, Prog. Brain Res., 2008, 121-135, 167.
Yehuda et al., Gene Expression Patterns Associated with Posttraumatic Stress Disorder Following Exposure to the World Trade Center Attacks, Biol. Psychiatry, 2009, 708-711, 66(7).
Young et al., Cortisol and Catecholamines in Posttraumatic Stress Disorder, Arch. Gen. Psychiatry, 2004, 394-401, 61(4).
Zieker et al., Differential gene expression in peripheral blood of patients suffering from post-traumatic stress disorder, Mol. Psychiatry, 2007, 116-118, 12(2).
http://www.broad.mit.edu/mpg/haploview/.
http://www.universalprobelibrary.com.
Alberts et al., Molecular Biology of the Cell 4th Ed., 2002, Garland Science, NY (Table of Contents).
Bakay et al., Sources of variability and effect of experimental approach on expression profiling data interpretation, BMC Bioinformatics, 2002, 4, 3 (12 pages).
Baker et al., Higher Levels of Basal Serial CSF Cortisol in Combat Veterans With Posttraumatic Stress Disorder, Am. J. Psychiatry, 2005, 992-994, 162(5).
Bernstein et al., Development and validation of a brief screening version of the Childhood Trauma Questionnaire, Child Abuse Negl., 2003, 169-190, 27(2).
Binder et al., Polymorphisms in FKBP5 are associated with increased recurrence of depressive episodes and rapid response to antidepressant treatment, Nat. Genet., 2004, 1319-1325, 36(12).
Biola et al., Interleukin-2 Inhibits Glucocorticoid Receptor Transcriptional Activity through a Mechanism Involving STAT5 (Signal Transducer and Activator of Transcription 5) but Not AP-1, Mol. Endocrinol., 2001, 1062-1076, 15(7).
Blake et al. The development of a Clinician-Administered PTSD Scale, J. Trauma Stress 1995, 75-90, 8(1).
Breslau, Outcomes of posttraumatic stress disorder, J. Clin. Psychiatry, 2001, 55-59, 62(Suppl. 17).
Broekman et al., The genetic background to PTSD, Neurosci. Biobehav. Rev., 2007, 348-362, 31(3).
Bundgaard (Ed.), Design of Prodrugs, 1985, Elsevier, NY (Table of Contents).
Coffey et al., Screening for PTSD in a substance abuse sample: psychometric properties of a modified version of the PTSD symptom scale self-report, J. Trauma Stress, 1998, 393-399, 11(2).
Cole et al., The EBV-hybridoma technique and its application to human lung cancer, in Reisfeld et al. (Ed.), Monoclonal Antibodies and Cancer Therapy, 1985, 77-96, Alan R. Liss, Inc.
Cooper, The Cell—A Molecular Approach 2nd Ed., 2000, Sinauer Associates, Inc. Sunderland, MA (Table of Contents).
De Kloet et al., Stress and the brain: from adaptation to disease, Nat. Rev. Neurosci., 2005, 463-475, 6(6).
Denny et al., Squirrel Monkey Immunophilin FKBP51 is a Potent Inhibitor of Glucocorticoid Receptor Binding, Endocrinology, 2000, 4107-4113, 141(11).
Dorner, The synthesis of peptidomimetic combinatorial libraries through successive amide alkylations, Bioorg. Med. Chem., 1996, 709-715, 4(5).
Elbashir et al., Functional anatomy of siRNAs for mediating efficient RNAi in *Drosophila melanogaster* embryo lysate, EMBO J., 2001, 6877-6888, 20(23).
Falsetti et al., The Modified PTSD Symptom Scale: A brief self-report measure of posttraumatic stress disorder, Behav. Therapist, 1993, 161-162, 16(6).
Fassina, Identification of Interactive Sites of Proteins and Protein Receptors by Computer-Assisted Searches for Complementary Peptide Sequences, Immunomethods, 1994, 114-120, 5(2).
Gentleman et al., Bioinformatics and computational biology solutions using R and bioconductor, 2005, Springer, NY (Table of Contents).
Glover et al., Urinary cortisol and catecholamines in mothers of child cancer survivors with and without PTSD, Psychoneuroendocrinology, 2002, 805-819, 27(7).
Goleva et al., A Role for STAT5 in the Pathogenesis of IL-2-Induced Glucocorticoid Resistance, J. Immunol., 2002, 5934-5940, 169(10).
Griffiths et al., Modem Genetic Analysis, 1999, W.H. Freeman, NY (Table of Contents).
Harlow et al. (Ed.), Antibodies, A Laboratory Manual, 1988, Cold Spring Harbor Press, New York (Table of Contents).
Harlow et al. (Ed.), Using Antibodies: A Laboratory Manual, 1999, Cold Spring Harbor Publications, NY (Table of Contents).
Hebbar et al., Chromatin-dependent cooperativity between site-specific transcription factors in vivo, J. Biol. Chem., 2007, 8284-8291, 282(11).
Heber et al., Quality Assessment of Affymetrix GeneChip Data, Omics, 2006, 358-368, 10(3).
Heim et al., The potential role of hypocortisolism in the pathophysiology of stress-related bodily disorders, Psychoneuroendocrinology, 2000, 1-35, 25(1).
Holsboer, The Corticosteroid Receptor Hypothesis of Depression, Neuropsychopharmacology, 2000, 477-501, 23(5).
Ising et al., Polymorphisms in the FKP5 gene region modulate recovery from psychosocial stress in healthy controls, Eur. J. Neurosci., 2008, 389-398, 28(2).
Kim et al., Polony Multiplex Analysis of Gene Expression (PMAGE) in Mouse Hypertrophic Cardiomyopathy, Science, 2007, 1481-1484, 316(5830).
King et al., Early sexual abuse and low cortisol, Psychiatry Clin. Neurosci., 2001, 71-74, 55(1).
Kingsmore, Multiplexed protein measurement: technologies and applications of protein and antibody arrays, Nat. Rev. Drug Discov., 2006, 310-320, 5(4).
Kirkpatrick et al., The absolute quantification strategy: a general procedure for the quantification of proteins and post-translational modifications, Methods, 2005, 265-273, 35(3).
Koenen et al., Polymorphisms in FKBP5 are associated with peritraumatic dissociation in medically injured children, Mol. Psychiatry, 2005, 1058-1059, 10(12).
Kohler et al, Continuous cultures of fused cells secreting antibody of predefined specificity, Nature, 1975, 495-497, 256(5517).
Kozbor et al., The production of monoclonal antibodies from human lymphocytes, Immunology Today, 1983, 72-79, 4(3).
Kubinyi, QSAR: Hansch Analysis and Related Approaches, 1992, VCH Verlag, Weinheim (Table of Contents).
Lemieux et al., Abuse-Related Posttraumatic Stress Disorder: Evidence for Chronic Neuroendocrine Activation in Women, Psychosom. Med., 1995, 105-115, 57(2).
Malmborg, BIAcore as a tool in antibody engineering, J. Immunol. Methods, 1995, 7-13, 183(1).
Melani et al., Inhibition of Proliferation by c-myb Antisense Oligodeoxynucleotides in Colon Adenocarcinoma Cell Lines That Express c-myb, Cancer Res., 1991, 2897-2901, 51(11).
Mullis et al. (Eds.), The Polymerase Chain Reaction, 1994, Birkhauser (Table of Contents).

(56) References Cited

OTHER PUBLICATIONS

Neylan et al., PTSD symptoms predict waking salivary cortisol levels in police officers, Psychoneuroendocrinology 2005, 373-378, 30(4).
Nielsen, Serial Analysis of Gene Expression (SAGE): Methods and Protocols, 2008, Humana Press, Totowa, NJ (Table of Contents).
Oquendo et al., Lower Cortisol Levels in Depressed Patients with Comorbid Post-Traumatic Stress Disorder, Neuropsychopharmacology, 2003, 591-598, 28(3).
Ostresh, Generation and use of nonsupport-bound peptide and peptidomimetic combinatorial libraries, Methods Enzyma, 1996, 220-234, 267.
Ozawa, Strategic proposals for avoiding toxic interactions with drugs for clinical use during development and after marketing of a new drug—proposals for designing non-clinical and clinical studies—is the non-clinical study useful?, J. Toxicol. Sci., 1996, 323-329, 21(5).
PABO, Computer-Aided Model-Building Strategies for Protein Design, Biochemistry, 1986, 5987-5991, 25(20).
C Thiede—"Buccal swabs but not mouthwash samples can be used to obtain pretransplant DNA fingerprints from recipients of allogeneic bone marrow transplants", Bone Marrow Transplantation (2000) 25, 575-577.
Mirjam Van Zuiden et al.—"Glucocorticoid Receptor Pathway Components Predict Posttraumatic Stress Disorder Symptom Development: A Prospective Study", Biol Psychiatry 2012:71-:309-516.
Einat Levy-Gigi—"Association Among Clinical Response, Hippocampal Volume, and FKBPS Gene Expression in Individuals with Posttraumatic Stress Disorder Receiving Cognitive Behavioral Therapy", Biol Psychiatry 2013,74:793-800.

* cited by examiner

Impaired Gene Expression Predicts PTSD
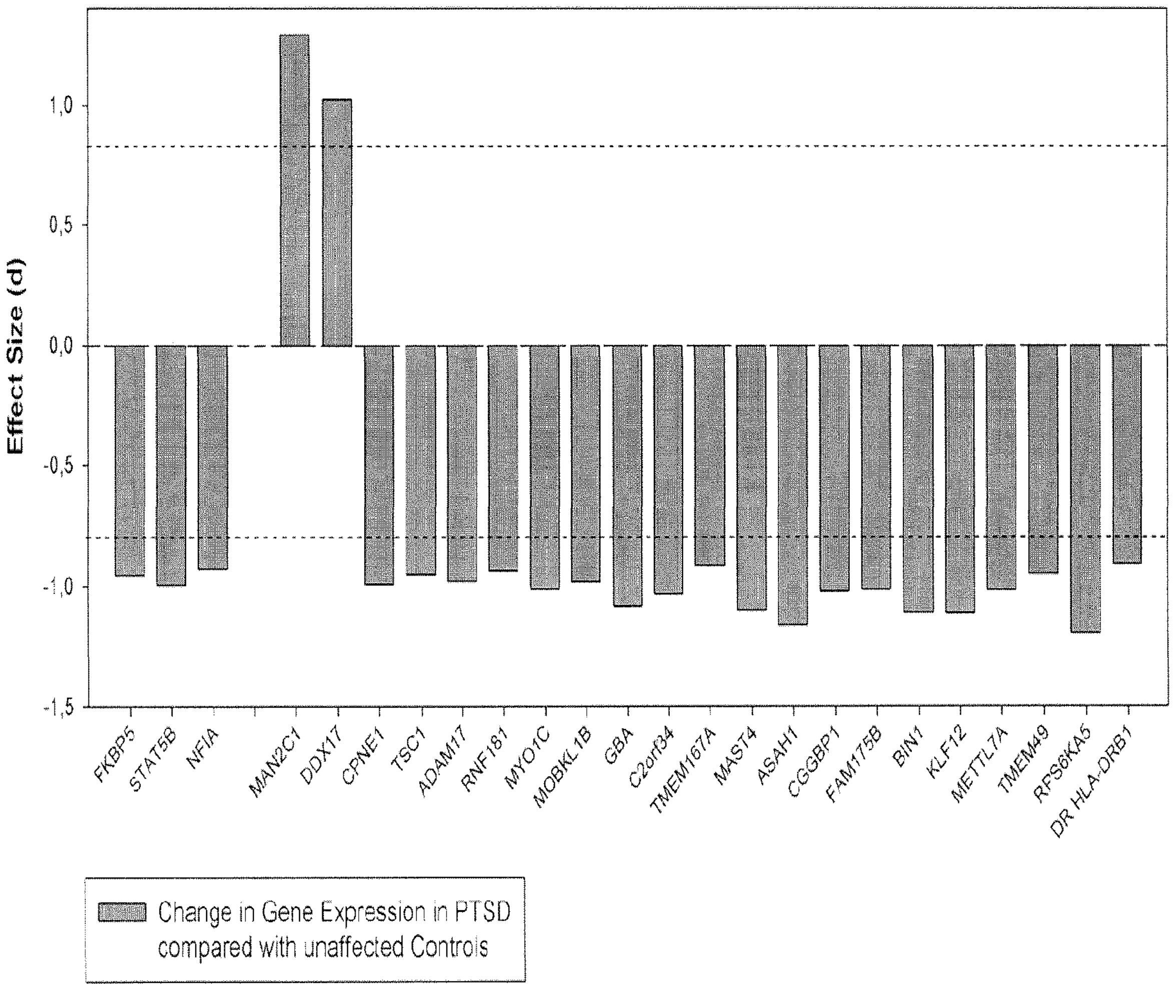

SEQUENCE LISTING

```
<160> NUMBER OF SEQ ID NOS: 25

<210> SEQ ID NO 1
<211> LENGTH: 3781
<212> TYPE: DNA
<213> ORGANISM: Homo sapiens
```

<400> SEQUENCE: 1

```
gggccggctc gcgggcgctg ccagtctcgg gcggcggtgt ccggcgcgcg ggcggcctgc     60
tgggcgggct gaagggttag cggagcacgg gcaaggcgga gagtgacgga gtcggcgagc    120
ccccgcggcg acaggttctc tacttaaaag acaatgacta ctgatgaagg tgccaagaac    180
aatgaagaaa gccccacagc cactgttgct gagcagggag aggatattac ctccaaaaaa    240
gacaggggag tattaaagat tgtcaaaaga gtggggaatg gtgaggaaac gccgatgatt    300
ggagacaaag tttatgtcca ttacaaagga aaattgtcaa atggaaagaa gtttgattcc    360
agtcatgata gaaatgaacc atttgtcttt agtcttggca aaggccaagt catcaaggca    420
tgggacattg gggtggctac catgaagaaa ggagagatat gccatttact gtgcaaacca    480
gaatatgcat atggctcggc tggcagtctc cctaaaattc cctcgaatgc aactctcttt    540
tttgagattg agctccttga tttcaaagga gaggatttat ttgaagatgg aggcattatc    600
cggagaacca aacggaaagg agagggatat tcaaatccaa acgaaggagc aacagtagaa    660
atccacctgg aaggccgctg tggtggaagg atgtttgact gcagagatgt ggcattcact    720
gtgggcgaag gagaagacca cgacattcca attggaattg acaaagctct ggagaaaatg    780
cagcgggaag aacaatgtat tttatatctt ggaccaagat atggttttgg agaggcaggg    840
aagcctaaat ttggcattga acctaatgct gagcttatat atgaagttac acttaagagc    900
ttcgaaaagg ccaaagaatc ctgggagatg gataccaaag aaaaattgga gcaggctgcc    960
attgtcaaag agaagggaac cgtatacttc aagggaggca aatacatgca ggcggtgatt   1020
cagtatggga agatagtgtc ctggttagag atggaatatg gtttatcaga aaaggaatcg   1080
aaagcttctg aatcatttct ccttgctgcc tttctgaacc tggccatgtg ctacctgaag   1140
cttagagaat acaccaaagc tgttgaatgc tgtgacaagg cccttggact ggacagtgcc   1200
aatgagaaag gcttgtatag gaggggtgaa gcccagctgc tcatgaacga gtttgagtca   1260
gccaagggtg actttgagaa agtgctggaa gtaaaccccc agaataaggc tgcaagactg   1320
cagatctcca tgtgccagaa aaaggccaag gagcacaacg agcgggaccg caggatatac   1380
gccaacatgt tcaagaagtt tgcagagcag gatgccaagg aagaggccaa taaagcaatg   1440
ggcaagaaga cttcagaagg ggtcactaat gaaaaaggaa cagacagtca agcaatggaa   1500
gaagagaaac ctgagggcca cgtatgacgc cacgccaagg agggaagagt cccagtgaac   1560
tcggcccctc ctcaatgggc tttcccccaa ctcaggacag aacagtgttt aatgtaaagt   1620
ttgttatagt ctatgtgatt ctggaagcaa atggcaaaac cagtagcttc ccaaaaacag   1680
ccccccctgct gctgcccgga gggttcactg aggggtggca cgggaccact ccaggtggaa   1740
caaacagaaa tgactgtggt gtggagggag tgagccagca gcttaagtcc agctcatttc   1800
agtttctatc aaccttcaag tatccaattc agggtccctg gagatcatcc taacaatgtg   1860
gggctgttag gttttacctt tgaactttca tagcactgca gaaacctttt aaaaaaaaat   1920
gcttcatgaa tttctccttt cctacagttg ggtagggtag gggaaggagg ataagctttt   1980
gtttttttaaa tgactgaagt gctataaatg tagtctgttg catttttaac caacagaacc   2040
cacagtagag gggtctcatg tctccccagt tccacagcag tgtcacagac gtgaaagcca   2100
gaacctcaga ggccacttgc ttgctgactt agcctcctcc caaagtcccc ctcctcagcc   2160
agcctccttg tgagagtggc tttctaccac acacagcctg tccctggggg agtaattctg   2220
tcattcctaa aacacccttc agcaatgata atgagcagat gagagtttct ggattagctt   2280
```

-continued

```
ttcctatttt cgatgaagtt ctgagatact gaaatgtgaa aagagcaatc agaattgtgc   2340

tttttctccc ctcctctatt ccttttaggg aataatattc aatacacagt acttcctccc   2400

agcattgcta ctgctcagct tcttctttca ttctaatcct tgctattaag aatttaagac   2460

ttgtgcttac aatatttttg acctggagtg gatctattta catagtcatt taggatccat   2520

gcagcttttt ttgtcttttt aagattattg gctcataagc atatgtatac tggtttatgg   2580

aactttattt acactcctct atcatgcaaa aaaattttga ctttttagta ctaagcttaa   2640

tttttaaaaa caaaatctgt agtgttgaca aataaatagt tgctcttcta cactaggggt   2700

ttcacctgca ggtttgacac gcagttgctc gcttttcctg ccctgtcaag cttctctgtt   2760

ctggcgtgag ttgtgaaaga gttgaagaca gcttcccatg ccggtacaca gccagtagcc   2820

taaatctcca gtacttgagc tgaccattga actagggcaa gtcttaaatg tgtacatgta   2880

gttgaatttc agtccttacg ggtaaacaga ttgagcatgg ctctctattc cctcagccta   2940

agaaacactc atgggaatgc atttggcaac ccaaggaacc atttgcttaa acctggaaca   3000

tctcaccttt ttaaatccta aaaaacactg gcagttatat tttaaattag tttttatttt   3060

tatgatggtt ttatcaaaag acttttatta ttagattggg accccccttca aacctaaaaa   3120

tcaagttatt tccttttata atacttttct tccccatgga acaaatggga tcaatttgtg   3180

agttttttcc tttaatgata actaaaatcc ctctaatttc tcatttatgc ttttgtcttt   3240

tttatgaaat atttctttta aaagccccag tctcacctac gaaatatgaa gagcaaaagc   3300

tgattttgct tacttgctaa actgttggga aagctctgta gagcatggtt ccagtgaggc   3360

caagattgaa atttgatact aaaaaggcca cctagctttt tgcagataac aaacaagaaa   3420

gctattccaa gactcagatg atgccagctg tctcccacgt gtgtattatg gttcaccagg   3480

gggaactggc aaaagtgtgt gtggggaggg gaagggtgtg tgagtggttc tgagcaaata   3540

actacagggt gcccattacc actcaagaag acacttcacg tattcttgta tcaaattcaa   3600

taatcttaaa caatttgtgt agaagtccac agacatcttt caaccacctt ttaggctgca   3660

tatggattgc caagtcagca tatgaggaat taaagacatt gtttttaaaa aaaaaaaatc   3720

atttagatgc actttttttgt gtgttcttta aataaatcca aaaaaaatgt gaaaaaaaaa   3780

a                                                                   3781
```

<210> SEQ ID NO 2
<211> LENGTH: 5171
<212> TYPE: DNA
<213> ORGANISM: Homo sapiens

<400> SEQUENCE: 2

```
ggcgggagga gagtcggcgg ccggagccgt caccccgggc ggggacccag cgcaggcaac     60

tccgcgcggc ggcccggccg agggagggag cgagcgggcg ggcgggcaag ccagacagct    120

gggccggagc agccgcgggc gcccgagggg ccgagcgaga ttgtaaacca tggctgtgtg    180

gatacaagct cagcagctcc aaggagaagc ccttcatcag atgcaagcgt tatatggcca    240

gcattttccc attgaggtgc ggcattattt atcccagtgg attgaaagcc aagcatggga    300

ctcagtagat cttgataatc cacaggagaa cattaaggcc acccagctcc tggagggcct    360

ggtgcaggag ctgcagaaga aggcagagca ccaggtgggg gaagatgggt ttttactgaa    420

gatcaagctg gggcactatg ccacacagct ccagaacacg tatgaccgct gccccatgga    480

gctggtccgc tgcatccgcc atatattgta caatgaacag aggttggtcc gagaagccaa    540

caatggtagc tctccagctg gaagccttgc tgatgccatg tcccagaaac acctccagat    600
```

-continued

```
caaccagacg tttgaggagc tgcgactggt cacgcaggac acagagaatg agttaaaaaa    660
gctgcagcag actcaggagt acttcatcat ccagtaccag gagagcctga ggatccaagc    720
tcagtttggc ccgctggccc agctgagccc ccaggagcgt ctgagccggg agacggccct    780
ccagcagaag caggtgtctc tggaggcctg gttgcagcgt gaggcacaga cactgcagca    840
gtaccgcgtg gagctggccg agaagcacca gaagaccctg cagctgctgc ggaagcagca    900
gaccatcatc ctggatgacg agctgatcca gtggaagcgg cggcagcagc tggccgggaa    960
cggcgggccc cccgagggca gcctggacgt gctacagtcc tggtgtgaga agttggccga   1020
gatcatctgg cagaaccggc agcagatccg cagggctgag cacctctgcc agcagctgcc   1080
catccccggc ccagtggagg agatgctggc cgaggtcaac gccaccatca cggacattat   1140
ctcagccctg gtgaccagca cgttcatcat tgagaagcag cctcctcagg tcctgaagac   1200
ccagaccaag tttgcagcca ctgtgcgcct gctggtgggc gggaagctga acgtgcacat   1260
gaaccccccc caggtgaagg ccaccatcat cagtgagcag caggccaagt ctctgctcaa   1320
gaacgagaac acccgcaatg attacagtgg cgagatcttg aacaactgct gcgtcatgga   1380
gtaccaccaa gccacaggca cccttagtgc ccacttcagg aatatgtccc tgaaacgaat   1440
taagaggtca gaccgtcgtg ggcagagtc ggtgacagaa gaaaaattta caatcctgtt   1500
tgaatcccag ttcagtgttg gtggaaatga gctggttttt caagtcaaga ccctgtccct   1560
gccagtggtg gtgatcgttc atggcagcca ggacaacaat gcgacggcca ctgttctctg   1620
ggacaatgct tttgcagagc ctggcagggt gccatttgcc gtgcctgaca aagtgctgtg   1680
gccacagctg tgtgaggcgc tcaacatgaa attcaaggcc gaagtgcaga gcaaccgggg   1740
cctgaccaag gagaacctcg tgttcctggc gcagaaactg ttcaacaaca gcagcagcca   1800
cctggaggac tacagtggcc tgtctgtgtc ctggtcccag ttcaacaggg agaatttacc   1860
aggacggaat tacactttct ggcaatggtt tgacggtgtg atggaagtgt taaaaaaaca   1920
tctcaagcct cattggaatg atggggccat tttggggttt gtaaacaagc aacaggccca   1980
tgacctactc attaacaagc cagatgggac cttcctcctg agattcagtg actcagaaat   2040
tggcggcatc accattgctt ggaagtttga ttctcaggaa agaatgtttt ggaatctgat   2100
gccttttacc accagagact tctccattcg gtccctagcc gaccgcttgg gagacttgaa   2160
ttaccttatc tacgtgtttc ctgatcggcc aaaagatgaa gtatactcca aatactacac   2220
accagttccc tgcgagtctg ctactgctaa agctgttgat ggatacgtga agccacagat   2280
caagcaagtg gtccctgagt ttgtgaacgc atctgcagat gccgggggcg gcagcgccac   2340
gtacatggac caggccccct ccccagctgt gtgtccccag gctcactata acatgtaccc   2400
acagaaccct gactcagtcc ttgacaccga tggggacttc gatctggagg acacaatgga   2460
cgtagcgcgg cgtgtggagg agctcctggg ccggccaatg gacagtcagt ggatcccgca   2520
cgcacaatcg tgaccccgcg acctctccat cttcagcttc ttcatcttca ccagaggaat   2580
cactcttgtg gatgttttaa ttccatgaat cgcttctctt ttgaaacaat actcataatg   2640
tgaagtgtta atactagttg tgaccttagt gtttctgtgc atggtggcac cagcgaaggg   2700
agtgcgagta tgtgtttgtg tgtgtgtgtg tgtgtgtgtg tgtgtgcgtg tttgcacgtt   2760
atggtgtttc tccctctcac tgtctgagag tttagttgta gcagaggggc cacagacaga   2820
agctgtggtg gtttttactt tgtgcaaaaa ggcagtgagt ttcgtgaagc ctggaagttg   2880
gccatgtgtc ttaagagtgg ctggactttg acatgtggct gtttgaataa gagaaggaca   2940
```

```
aagggaggag aaagcacatg tgctccagtg agtcttcgtc actctgtctg ccaagcaatt   3000
gatatataac cgtgattgtc tctgcttttc ttctgaaatg tagataactg ctttttgaca   3060
aagagagcct tccctctccc ccacccctgt gttcttgggt aggaatggga aaaggggcaa   3120
cctacaaaga ttgttggggc aagggaagtc acaagctttc ggatgggcgg tggcttttca   3180
caaaacattt agctcatctt attctctctt tgtcctctct cccctcctgc ccgcccgcac   3240
cctggaattg ccactcagtt cctctgggtg tgcacatatg tttggagaaa tagaggagag   3300
aaaagagggc cacgtaactg agagcttaca gtgccaatgc cgtttgtgtt ctggccagag   3360
tggagtgcgc agccctgact cccaggcgct gagattgttg cctggttacc caggaagctg   3420
ctgttccggc tgcccagcct ttctctgagc cagcggatgc acagtccgtg gccttcttca   3480
ggcttattga tgatgctttt tgcaaatgtt gaatcatggt tctgtttcta agttggatct   3540
tttttgtttt ctccttgcca ccctaatttg acatcaaaat tctctcttgt gcattgggcc   3600
ctgggtcatt caaacccagg tcacctcatt ccccttctct gttcacacct aatgtcttga   3660
agagtaggta gcagcagtgt gggctgaacc taggccagct tgcttagcgg gtcaccctgc   3720
tgtgaagtcc tggcaggtgt tggtaatgtg tggaaatgca gtcagcaagt ttgctgggga   3780
gtttgataaa agtataaaac aaaacaaaaa aagcctcggt ataattttgt tccacgactt   3840
cttctgtagc tttacaccag aaggaaggaa tgggctacag caggtagtgg aggaagaggg   3900
gggtgagcag gtgtattaaa atagcttacg ggtaaggcct aaaaggtcac ccctcggccc   3960
cctctccaaa agaagggcat gggcaccccc aggagaggat ggccccaaaa accttatttt   4020
tatacatgag agtaaataaa catatttttt ttacaaaaat aacttctgaa tttatcagtg   4080
ttttgccgtt aaaaatattc ctctatagta aattatttat tggaagatga ctttttttaaa   4140
gctgccgttt gccttggctt ggtttcatac actgatttat ttttctatgc caggcagtag   4200
agtctctctg cctctgagga gcaggctacc cgcatcccac tcagcccctc cctacccctc   4260
aagatttgat gaaaattcca accatgagga tgggtgcatc ggggaagggt gagaaggaga   4320
gcctgcctgc tcagggatcc aggctcgtag agtcactccc tgcccgtctc ccagagatgc   4380
ttcaccagca cctgcctctg agacctcgct ctctgttcca gcaaccctgg ttggggggtc   4440
agacttgata cactttcagg ttgggagtgg acccacccca gggcctgctg aggacagagc   4500
agccaggccg tcctggctca ctttgcagtt ggcactgggt tggggaggaa gagagctgat   4560
gagtgtggct tccctgagct ggggtttccc tgcttgtcca gttgtgagct gtcctcggtg   4620
ttaccgaggc tgtgcctaga gagtggagat ttttgatgaa aggtgtgctc gctctctgcg   4680
ttctatcttc tctctcctcc ttgttcctgc aaaccacaag ataaaggtag tggtgtgtct   4740
cgaccccatc agcctctcac ccactcccag acacacacaa gtcctcaaaa gtttcagctc   4800
cgtgtgtgag atgtgcaggt tttttctagg gggtaggggg agactaaaat cgaatataac   4860
ttaaaatgaa agtatacttt ttataatttt tctttttaaa acttggtgaa attatttcag   4920
atacatattt tagtgtcaag gcagattagt tatttagcca ccaaaaaaaa gtattgtgta   4980
caatttgggg cctcaaattt gactctgcct caaaaaaaag aaatatatcc tatgcagagt   5040
tacagtcaca aagttgtgta ttttatgtta caataaagcc ttcctctgaa gggaaaaaaa   5100
aaaaaaaaaa aaaaaaaaaa aaaaaaaaaa aaaaaaaaaa aaaaaaaaaa aaaaaaaaaa   5160
aaaaaaaaaa a                                                        5171
```

<210> SEQ ID NO 3
<211> LENGTH: 2684

<212> TYPE: DNA
<213> ORGANISM: Homo sapiens

<400> SEQUENCE: 3
gtcttggaaa tgtgaacgca agaagcaggc ttgatttttt tttctccccc cttctctctc 60
tctctctctc tctctcttcc tctctccctc tttctcctct ctcacccaca ctcacgcaca 120
cctccaaacc gcacacccag acgcacacgc ataccccagc gcccggcagt tatgtattct 180
ccgctctgtc tcacccagga tgaatttcat cctttcatcg aagcacttct gccccacgtc 240
cgagcctttg cctacacatg gttcaacctg caggcccgaa aacgaaaata cttcaaaaaa 300
catgaaaagc gtatgtcaaa agaagaagag agagccgtga aggatgaatt gctaagtgaa 360
aaaccagagg tcaagcagaa gtgggcatct cgacttctgg caaagttgcg gaaagatatc 420
cgacccgaat atcgagagga ttttgttctt acagttacag ggaaaaaacc tccatgttgt 480
gttctttcca acccagacca gaaaggcaag atgcgaagaa ttgactgcct ccgccaggca 540
gataaagtct ggaggttgga ccttgttatg gtgattttgt ttaaaggtat tccgctggaa 600
agtactgatg gcgagcgcct tgtaaagtcc ccacaatgct ctaatccagg gctctgtgtc 660
caaccccatc acataggggt ttctgttaag gaactcgatt tatatttggc atactttgtg 720
catgcagcag attcaagtca atctgaaagt cccagccagc caagtgacgc tgacattaag 780
gaccagccag aaaatggaca tttgggcttc caggacagtt ttgtcacatc aggtgttttt 840
agtgtcactg agctagtaag agtgtcacag acaccaatag ctgcaggaac tggcccaaat 900
ttttctctct cagatttgga aagttcttca tactacagca tgagtccagg agcaatgagg 960
aggtctttac ccagcacatc ctctacgagc tccacaaagc gcctcaagtc tgtggaggat 1020
gaaatggaca gtcctggtga ggagccattt tatacaggcc aagggcgctc cccaggaagt 1080
ggcagtcagt caagtggatg gcatgaagtg gagccaggaa tgccatctcc aaccacactg 1140
aagaagtcgg agaagtctgg tttcagcagc cctcccctt cacagacctc ctccctggga 1200
acggcgttca cacagcatca ccgacctgtc attacaggac ccagagcaag tccgcatgca 1260
acaccatcga ctcttcattt cccgacatca cccattatcc agcagcctgg gccttacttc 1320
tcacacccag ccatccgcta tcaccctcag gagacgctga aagaatttgt ccaacttgtc 1380
tgccctgatg ctggtcagca ggctggacag gtggggttcc tcaatcccaa tgggagcagc 1440
caaggcaagg tgcacaaccc attccttccc accccaatgt tgccaccgcc accgccacca 1500
ccgatggcca ggcctgtgcc tctgccggtg ccagacacaa agcctccaac cacgtcaaca 1560
gaaggaggtg cagcctcccc cacgtcacca atcctggtac ctgggataaa agttgcagcg 1620
tcccaccatc caccagacag accacctgac cccttctcaa ctctgtaaca tggacgcaac 1680
ctcaacccag cgcagttaca acttcactat cagcggaagg ggagaaaaac cgattcaaat 1740
caacttgtac atggaaacag caagcattat ggtcaaacag caaaggccat aaccttttgg 1800
gatttttttt tttttttaaa tactttaggg actgttgtaa tttctcatat ggtgctggaa 1860
atggttgggc tttgtaacat ttgaagtgtt tccatggtag cgtgagcatt aggtgacgtg 1920
gctagcggag gactaccctt gctcactgac ttcctgttgt aacacacttt ccttacggag 1980
cctggctgtt tcacagtatt tcatgaattt acccacacag gtgtgatcct ccttgagcat 2040
tgaggaggca catggagaac taaatctttt gtagtagctg agatctgcaa tatataacgg 2100
gacagtcaaa gggcaatgtt tttctgtaac atattggaaa aagaaaatgc agttatattc 2160 ctttttttatt tgttccttta gtttgttttg gttcagcagt cagcagttaa gtatataaca 2220

-continued

```
tggcccgcaa ggacaatgaa tccactcaca ttgcagaaca attccgaaaa tggcaaacta   2280

ctactactac tgttcagttt tttaaaagtt ttgaaatgct gcacttacat ttaaaaaaac   2340

aacaacaaca ttttttcaac aatttcaaca atgacacaaa aattcacatg gaaatgggga   2400

agatggtctg ttttgacaga aactgacagg aatcaatcaa aacaatcgaa ttttgaattg   2460

agtaaagtgc aatttcattg gatagctaaa tatctttgta agatagagat tgttgaaaat   2520

tctatttttg tttttctagt cctttcaccc caggactcta aattattggg gtaaaaaaca   2580

gccttgcaag aaaaagggga gctatttttg ctttttatgt tttttattgt taaacttgta   2640

tccctttaaa aactaaaaaa aaaaaaaaaa aaaaaaaaaa aaaa                   2684
```

<210> SEQ ID NO 4
<211> LENGTH: 3254
<212> TYPE: DNA
<213> ORGANISM: Homo sapiens

<400> SEQUENCE: 4

```
ggagcgagag cccggcgatg gcggctgcgc cggccttgaa gcactggcgc accacgctgg     60

agcgggtgga gaagttcgtg tcgccgctct actttaccga ctgtaacctc cgcggcaggc    120

tttttggggc cagctgccct gtggctgtgc tctccagctt cctgacgccg gagagacttc    180

cctaccagga ggcagtccag cgggacttcc gccccgcgca ggtcggcgac agcttcggac    240

ccacatggtg gacctgctgg ttccgggtgg agctgaccat cccagaggca tgggtgggcc    300

aggaagttca cctttgctgg gaaagtgatg gagaaggtct ggtgtggcgt gatggagaac    360

ctgtccaggg tttaaccaaa gagggtgaga agaccagcta tgtcctgact gacaggctgg    420

gggaaagaga cccccgaagc ctcactctct atgtggaagt agcctgcaat gggctcctgg    480

gggccgggaa gggaagcatg attgcagccc ctgaccctga gaagatgttc cagctgagcc    540

gggctgagct agctgtgttc caccgggatg tccacatgct cctggtggat ctggagctgc    600

tgctgggcat agccaagggc ctcgggaagg acaaccagcg cagcttccag gccctgtaca    660

cagccaatca gatggtgaac gtgtgtgacc ctgcccagcc cgagaccttc ccagtggccc    720

aggccctggc ctccaggttc tttggccaac atgggggtga aagccaacac accattcatg    780

ccacagggca ctgccacatt gatacagcct ggctttggcc cttcaaagag actgtgagga    840

aatgtgcccg gagctgggtg accgccctgc agctcatgga gcggaaccct gagttcatct    900

ttgcctgctc ccaggcgcag cagctggaat gggtgaagag ccgctaccct ggcctgtact    960

cccgcatcca ggagtttgcg tgccgtgggc agtttgtgcc tgtgggggc acctgggtgg   1020

agatggatgg gaacctgccc agtggagagg ccatggtgag gcagtttttg cagggccaga   1080

acttctttct gcaggagttt gggaagatgt gctctgagtt ctggctgccg gacacctttg   1140

gctactcagc acagctcccc cagatcatgc acggctgtgg catcaggcgc tttctcaccc   1200

agaaattgag ctggaatttg gtgaactcct tcccacacca tacatttttc tgggagggcc   1260

tggatggctc ccgtgtactg gtccacttcc cacctggcga ctcctatggg atgcagggca   1320

gcgtggagga ggtgctgaag accgtggcca acaaccggga caaggggcgg gccaaccaca   1380

gtgccttcct ctttggcttt ggggatgggg gtggtggccc cacccagacc atgctggacc   1440

gcctgaagcg cctgagcaat acggatgggc tgcccagggt gcagctatct tctccaagac   1500

agctcttctc agcactggag agtgactcag agcagctgtg cacgtgggtt ggggagctct   1560

tcttggagct gcacaatggc acatacacca cccatgccca gatcaagaag gggaaccggg   1620

aatgtgagcg gatcctgcac gacgtggagc tgctcagtag cctggccctg gcccgcagtg   1680
```

-continued cccagttcct atacccagca gcccagctgc agcacctctg gaggctcctt cttctgaacc 1740
agttccatga tgtggtgact ggaagctgca tccagatggt ggcagaggaa gccatgtgcc 1800
attatgaaga catccgttcc catggcaata cactgctcag cgctgcagcc gcagccctgt 1860
gtgctgggga gccaggtcct gagggcctcc tcatcgtcaa cacactgccc tggaagcgga 1920
tcgaagtgat ggccctgccc aaaccgggcg gggcccacag cctagccctg gtgacagtgc 1980
ccagcatggg ctatgctcct gttcctcccc ccacctcact gcagcccctg ctgccccagc 2040
agcctgtgtt cgtagtgcaa gagactgatg gctccgtgac tctggacaat ggcatcatcc 2100
gagtgaagct ggacccaact ggtcgcctga cgtccttggt cctggtggcc tctggcaggg 2160
aggccattgc tgagggcgcc gtggggaacc agtttgtgct atttgatgat gtccccttgt 2220
actgggatgc atgggacgtc atggactacc acctggagac acggaagcct gtgctgggcc 2280
aggcagggac cctggcagtg ggcaccgagg gcggcctgcg gggcagcgcc tggttcttgc 2340
tacagatcag ccccaacagt cggcttagcc aggaggttgt gctggacgtt ggctgcccct 2400
atgtccgctt ccacaccgag gtacactggc atgaggccca caagttcctg aaggtggagt 2460
tccctgctcg cgtgcggagt tcccaggcca cctatgagat ccagtttggg cacctgcagc 2520
gacctaccca ctacaatacc tcttgggact gggctcgatt tgaggtgtgg gcccatcgct 2580
ggatggatct gtcagaacac ggctttgggc tggccctgct caacgactgc aagtatggcg 2640
cgtcagtgcg aggcagcatc ctcagcctct cgctcttgcg ggcgcctaaa gccccggacg 2700
ctactgctga cacggggcgc cacgagttca cctatgcact gatgccgcac aagggctctt 2760
tccaggatgc tggcgttatc caagctgcct acagcctaaa cttccccctg ttggctctgc 2820
cagcccccag cccagcgccc gccacctcct ggagtgcgtt ttccgtgtct tcacccgcgg 2880
tcgtattgga gaccgtcaag caggcggaga gcagccccca gcgccgctcg ctggtcctga 2940
ggctgtatga ggcccacggc agccacgtgg actgctggct gcacttgtcg ctgccggttc 3000
aggaggccat cctctgcgat ctcttggagc gaccagaccc tgctggccac ttgacccttc 3060
gggacaaccg cctgaagctc accttttctc ccttccaagt gctgtccctg ttgctcgtgc 3120
ttcagcctcc gccacactga gtccctgggg ctggggtttt gtttgtagaa ggctctgggg 3180
actcctaatt tctgcttccc cagcctaaag cagggatcag tcttttcttg tggaataaat 3240
ccttggatcg ggaa 3254

<210> SEQ ID NO 5
<211> LENGTH: 3676
<212> TYPE: DNA
<213> ORGANISM: Homo sapiens

<400> SEQUENCE: 5
gagtagaagt gatttggcct cataacttca cagtggttta ccactttgtt ctatgttctg 60
gttttgtaaa ggatagtact ggaatttgcg tctgaagacc aatattggtg taactcctgt 120
cagtatattg gtaaaatgta gcagaggcag gagtttggat gtttggatgg gattccctta 180
ggattctaca gccaataaag atcctatttc ctatgcatgt cccaggaatc agtaatcctc 240
ttttactctg ttgggatgag tcttttttttg tttctgttca gagtggttac taacttcacc 300
ttctttcctc ttgctgtcat ctgcattcgt gcttccccacc tgttgttggc atgtccttta 360
ccttctcttt ccctgccaca tcaacctaca cactgactca tcattgacgt ggaagatgtg 420
gaagatgtca agtttgtgat caactatgac tatccaaaca gctcagagga ttatgtgcac 480

-continued

```
cgtattggcc gaacagcccg tagcaccaac aagggtaccg cctatacctt cttcacccca    540
gggaacctaa aacaggccag agagcttatc aaagtgctgg aagaggccaa tcaggctatc    600
aatccaaaac tgatgcagct tgtggaccac agaggaggcg gcggaggcgg gggtaagggt    660
ggtcgttctc gttaccggac cacttcttca gccaacaatc ccaatctgat gtatcaggat    720
gagtgtgacc gaaggcttcg aggagtcaag gatggtggcc ggagagactc tgcaagctat    780
cgggatcgta gtgaaaccga tagagctggt tatgctaatg gcagtggcta tggaagtcca    840
aattctgcct ttggagcaca agcaggccaa tacacctatg gtcaaggcac ctatggggca    900
gctgcttatg gcaccagtag ctatacagct caagaatatg gtgctggcac ttatggagct    960
agtagcacca cctcaactgg gagaagttca cagagctcta gccagcagtt tagtgggata   1020
ggccggtctg ggcagcagcc acagccactg atgtcacaac agtttgcaca gcctccggga   1080
gctaccaata tgataggtta catggggcag actgcctacc aataccctcc tcctcctccc   1140
cctcctcctc cttcacgtaa atgaaaccac tcaagtggta gtgactccag cagacttaat   1200
tacattttaa ggaacactgt ctttcctttt tttttcctct tcgccttttc ttttttttc   1260
ctttttttctt ttttttttt taatttttcc ccccaaccat cgtgatttgt cttttcatgc   1320
agattagtta gaattcactg ccaggtttct tctgcccacc aaaatgatcc agtctggaat   1380
aacattttgt aaaaaaaaaa aaaatatata tatatatata tagctgactg gaagagatta   1440
atttcttccc ccaacttctt gcatgttgaa gatatttgag ctatttttca tctaaaagag   1500
taaggtatta ggccctttg tgggagcccc atgttttgtt tttctgagtt ggtggggagg   1560
gagggagggg gagggctgaa ttgttttgca gaggaagatg gcatctgtgc tttaaatttc   1620
tcattactgg gttagaaaac aaagagggat tgccctgcac atttcttttt gtgcttttaa   1680
atgtttctta agttggaaca ggtttcctcg ggcctgtttt gactgattgc tggagtgcat   1740
ttgatagtta aaaattacta attggtttta tttcccttca cactctgcct ccccacttct   1800
ccccccgtta ctgaaaaata accattttag tgtcaggcta gaaattgaat tgctgagttt   1860
tgtgtatcct ttaaattaaa aaccacaagt gtttattgta gtggttaaac tgtagcatct   1920
cagcatctgg gtggaagctg cctatatttc ttcccagttt aactggggac catctgtgaa   1980
attaatttc catccagaca gctgctgtga gcaaatgaac ataaatgctc gctggaaatt   2040
tactaaccag tttttatatt gacctgcagt gtaaaaagca catttaatta taaacaatat   2100
attcaaaatg ggcaaatttt attttcaaat gcagtgtaga gctagattaa aagcaactct   2160
ttgccaccta ctctgccctt ttggcaaagt taccttgaac aaagaatctt aagggtttat   2220
taagaactct ttattttctt catacctgt tctctgcagt gctttctaac agcttctggg   2280
tgcagatttt cttcggcatc cttttgcact cagcttatta caggtaggta gtgcttaaga   2340
aaagtcatgg aggactaaag cctaagtcct tttcactttt cctccatctg aaggtaggtg   2400
agttcatcct cttcatggta atgctgtttt accaagactt tatagcagat ggacccagaa   2460
agaattttct gctattgtgt tcactacaac aggataggga catcagacag ccccagaaac   2520
cccttccaga tctgatatgg gactattaat ttttatgctg ttaattggta ttcattcaca   2580
atgcagttga agggggaagg ctccactgca ttctttggct aaggcctgaa tgcttgctca   2640
tctgtaagat ctatactcga ggttttgttt tccttttaaa attctttagg gagagaggga   2700
tggtttctga ggggttctga aagtatgatt caatgtgcaa catacaggta ggtcttcagc   2760
ataagctgaa atatatgcat gtaaaaactt tgacatcttt ttttttaatt ttccactttc   2820
ttcttaactt tacttctctt tttgtccccc ccccatctta cagaagttga ggccaaggga   2880
```

-continued gaatggtagg cacagaagaa acatggcaaa ctgctctgtg ctttcaaacc aaagtgttcc 2940
ccccaacccc aaatttgtct aagcactggc cagtctgttg tgggcattgt tttctacaac 3000
caaattctgg gttttttct tctttcttta aacatagagg taccaccaca agggatgccc 3060
tactctctcg cagctcttga aagcatctgt ttgagggaaa ggtctctggg caagcaagtg 3120
gttatttgga ttgcttgctt cccttttcc acctgggaca ttgtaatcat aaaataacag 3180
taaattccaa acctcaaaaa ctattatggc ctgagcacag ctgaaatcta gcagagttta 3240
actcttctgc ctccatgtct gtcacttata attcaggttc tgctgttggc ttcagaacat 3300
gagcagaaga atcgttttat gctagttatt gcattcatgg ttgaaactca acttagggaa 3360
agggttccaa tgtattaagc aatgggctgc ttctccccaa tcctccctaa caattcgttg 3420
tgtggacttc tcatctaaaa ggttagtggc ttttgcttgg gatcagtgct ctctattgat 3480
gttcttgctg gtctccagac acattcctgt tgcattaaga cttgaaagac ttgtagatgt 3540
gtgatgttca ggcacaggat gctgaaagct atgttactat tcttagtttg taaattgtcc 3600
ttttgatacc atcatcttgt tttcttttg taggtataaa taaaaacact gttgacaata 3660
aaaaaaaaaa aaaaaa 3676

<210> SEQ ID NO 6
<211> LENGTH: 2211
<212> TYPE: DNA
<213> ORGANISM: Homo sapiens

<400> SEQUENCE: 6
ggcgaaggct ttgtagagtt cagaaatgag gctgactata aggctgctct gtgtcgtcat 60
aaacagtaca tgggcaatcg ctttattcaa gttcatccaa ttactaagaa aggtatgcta 120
gaaaagatag atatgattcg aaaaagactg cagaacttca gctatgacca gagggaaatg 180
atactaaatc cagaggggga tgtcaactct gccaaagtct gtgcccacat aacaaatatt 240
ccattcagca ttacaaagat ggatgttctt cagttcctag aaggaatccc agtggatgaa 300
aatgctgtac atgttcttgt tgataacaat gggcaaggtc taggacaggc attggttcag 360
tttaaaaatg aagatgatgc acatggccca ctgcgtgacc ttggttcagc tgtccatttc 420
ctgtgaccat ctcattgaca aggacatcgg ctccaagtct gacccactct gcgtcctttt 480
acaggatgtg ggaggggca gctgggctga gcttggccgg actgaacggg tgcggaactg 540
ctcaagccct gagttctcca agactctaca gcttgagtac cgctttgaga cagtccagaa 600
gctacgcttt ggaatctatg acatagacaa caagacgcca gagctgaggg atgatgactt 660
cctagggggt gctgagtgtt ccctaggaca gattgtgtcc agccaggtac tgactctccc 720
cttgatgctg aagcctggaa aacctgctgg gcgggggacc atcacggtct cagctcagga 780
attaaaggac aatcgtgtag taaccatgga ggtagaggcc agaaacctag ataagaagga 840
cttcctggga aaatcagatc catttctgga gttcttccgc cagggtgatg ggaaatggca 900
cctggtgtac agatctgagg tcatcaagaa caacctgaac cctacatgga agcgtttctc 960
agtccccgtt cagcatttct gtggtgggaa ccccagcaca cccatccagg tgcaatgctc 1020
cgattatgac agtgacgggt cacatgatct catcggtacc ttccacacca gcttggccca 1080
gctgcaggca gtcccggctg agtttgaatg catccaccct gagaagcagc agaaaaagaa 1140
aagctacaag aactctggaa ctatccgtgt caagatttgt cgggtagaaa cagagtactc 1200
ctttctggac tatgtgatgg gaggctgtca gatcaacttc actgtgggcg tggacttcac 1260

```
tggctccaat ggagacccct cctcacctga ctccctacac tacctgagtc caacaggggt   1320

caatgagtac ctgatggcac tgtggagtgt gggcagcgtg gttcaggact atgactcaga   1380

caagctgttc cctgcatttg gatttggggc ccaggttccc cctgactggc aggtctcgca   1440

tgaatttgcc ttgaatttca accccagtaa cccctactgt gcaggcatcc agggcattgt   1500

ggatgcctac cgccaagccc tgccccaagt tcgcctctat ggccctacca actttgcacc   1560

catcatcaac catgtggcca ggtttgcagc ccaggctgca catcagggga ctgcctcgca   1620

atacttcatg ctgttgctgc tgactgatgg tgctgtgacg gatgtggaag ccacacgtga   1680

ggctgtggtg cgtgcctcga acctgcccat gtcagtgatc attgtgggtg tgggtggtgc   1740

tgactttgag gccatggagc agctggacgc tgatggtgga cccctgcata cacgttctgg   1800

gcaggctgct gcccgcgaca ttgtgcagtt tgtaccctac cgccggttcc agaatgcccc   1860

tcgggaggca ttggcacaga ccgtgctcgc agaagtgccc acacaactgg tctcatactt   1920

cagggcccag ggttgggccc cgctcaagcc acttccaccc tcagccaagg atcctgcaca   1980

ggccccccag gcctaggttc ccttggaggc tgtggcaagt cctcaatcct gtgtcccaga   2040

ggtccctctg ggccacaacc caacccttct cactctcctc agtgctagca ctttgtattt   2100

tttgatactt ttatacttgt ttctgctttt gctgctcttg atcccacctt tgctcctgac   2160

aaccctcatt caataaagac cagtgaagac caaaaaaaaa aaaaaaaaaa a            2211
```

<210> SEQ ID NO 7
<211> LENGTH: 8617
<212> TYPE: DNA
<213> ORGANISM: Homo sapiens

<400> SEQUENCE: 7

```
acgacggggg aggtgctgta cgtccaagat ggcggcgccc tgtaggctgg agggactgtg     60

aggtaaacag ctgaggggga ggagacggtg gtgaccatga aagacaccag gttgacagca    120

ctggaaactg aagtaccagt tgtcgctaga acagtttggt agtggcccca atgaagaacc    180

ttcagaacct gtagcacacg tcctggagcc agcacagcgc cttcgagcga gagaatggcc    240

caacaagcaa atgtcgggga gcttcttgcc atgctggact cccccatgct gggtgtgcgg    300

gacgacgtga cagctgtctt taaagagaac ctcaattctg accgtggccc tatgcttgta    360

aacaccttgg tggattatta cctggaaacc agctctcagc cggcattgca catcctgacc    420

accttgcaag agccacatga caagcacctc ttggacagga ttaacgaata tgtgggcaaa    480

gccgccactc gtttatccat cctctcgtta ctgggtcatg tcataagact gcagccatct    540

tggaagcata agctctctca agcacctctt ttgccttctt tactaaaatg tctcaagatg    600

gacactgacg tcgttgtcct cacaacaggc gtcttggtgt tgataaccat gctaccaatg    660

attccacagt ctgggaaaca gcatcttctt gatttctttg acatttttgg ccgtctgtca    720

tcatggtgcc tgaagaaacc aggccacgtg gcggaagtct atctcgtcca tctccatgcc    780

agtgtgtacg cactctttca tcgcctttat ggaatgtacc cttgcaactt cgtctccttt    840

ttgcgttctc attacagtat gaaagaaaac ctggagactt ttgaagaagt ggtcaagcca    900

atgatggagc atgtgcgaat tcatccggaa ttagtgactg gatccaagga ccatgaactg    960

gaccctcgaa ggtggaagag attagaaact catgatgttg tgatcgagtg tgccaaaatc   1020

tctctggatc ccacagaagc ctcatatgaa gatggctatt ctgtgtctca ccaaatctca   1080

gcccgctttc ctcatcgttc agccgatgtc accaccagcc cttatgctga cacacagaat   1140

agctatgggt gtgctacttc taccccttac tccacgtctc ggctgatgtt gttaaatatg   1200
```

-continued

```
ccagggcagc tacctcagac tctgagttcc ccatcgacac ggctgataac tgaaccacca   1260
caagctactc tttggagccc atctatggtt tgtggtatga ccactcctcc aacttctcct   1320
ggaaatgtcc cacctgatct gtcacaccct tacagtaaag tctttggtac aactgcaggt   1380
ggaaaaggaa ctcctctggg aaccccagca acctctcctc ctccagcccc actctgtcat   1440
tcggatgact acgtgcacat ttcactcccc caggccacag tcacaccccc caggaaggaa   1500
gagagaatgg attctgcaag accatgtcta cacagacaac accatcttct gaatgacaga   1560
ggatcagaag agccacctgg cagcaaaggt tctgtcactc taagtgatct tccagggttt   1620
ttaggtgatc tggcctctga agaagatagt attgaaaaag ataaagaaga agctgcaata   1680
tctagagaac tttctgagat caccacagca gaggcagagc ctgtggttcc tcgaggaggc   1740
tttgactctc ccttttaccg agacagtctc ccaggttctc agcggaagac ccactcggca   1800
gcctccagtt ctcagggcgc cagcgtgaac cctgagcctt tacactcctc cctggacaag   1860
cttgggcctg acacaccaaa gcaagccttt actcccatag acctgccctg cggcagtgct   1920
gatgaaagcc ctgcgggaga cagggaatgc cagacttctt tggagaccag tatcttcact   1980
cccagtcctt gtaaaattcc acctccgacg agagtgggct ttggaagcgg gcagcctccc   2040
ccgtatgatc atctttttga ggtggcattg ccaaagacag cccatcattt tgtcatcagg   2100
aagactgagg agctgttaaa gaaagcaaaa ggaaacacag aggaagatgg tgtgccctct   2160
acctccccaa tggaagtgct ggacagactg atacagcagg gagcagacgc gcacagcaag   2220
gagctgaaca agttgccttt acccagcaag tctgtcgact ggacccactt tggaggctct   2280
cctccttcag atgagatccg caccctccga gaccagttgc ttttactgca caaccagtta   2340
ctctatgagc gttttaagag gcagcagcat gccctccgga acaggcggct cctccgcaag   2400
gtgatcaaag cagcagctct ggaggaacat aatgctgcca tgaaagatca gttgaagtta   2460
caagagaagg acatccagat gtggaaggtt agtctgcaga aagaacaagc tagatacaat   2520
cagctccagg agcagcgtga cactatggta accaagctcc acagccagat cagacagctg   2580
cagcatgacc gagaggaatt ctacaaccag agccaggaat tacagacgaa gctggaggac   2640
tgcaggaaca tgattgcgga gctgcggata gaactgaaga aggccaacaa caaggtgtgt   2700
cacactgagc tgctgctcag tcaggtttcc caaaagctct caaacagtga gtcggtccag   2760
cagcagatgg agttcttgaa caggcagctg ttggttcttg gggaggtcaa cgagctctat   2820
ttggaacaac tgcagaacaa gcactcagat accacaaagg aagtagaaat gatgaaagcc   2880
gcctatcgga aagagctaga aaaaaacaga agccatgttc tccagcagac tcagaggctt   2940
gatacctccc aaaaacggat tttggaactg gaatctcacc tggccaagaa agaccacctt   3000
cttttggaac agaagaaata tctagaggat gtcaaactcc aggcaagagg acagctgcag   3060
gccgcagaga gcaggtatga ggctcagaaa aggataaccc aggtgtttga attggagatc   3120
ttagatttat atggcaggtt ggagaaagat ggcctcctga aaaaacttga agaagaaaaa   3180
gcagaagcag ctgaagcagc agaagaaagg cttgactgtt gtaatgacgg gtgctcagat   3240
tccatggtag ggcacaatga agaggcatct ggccacaacg gtgagaccaa gacccccagg   3300
cccagcagcg cccggggcag tagtggaagc agaggtggtg gaggcagcag cagcagcagc   3360
agcgagcttt ctaccccaga gaaaccccca caccagaggg caggcccatt cagcagtcgg   3420
tgggagacga ctatgggaga agcgtctgcc agcatcccca ccactgtggg ctcacttccc   3480
agttcaaaaa gcttcctggg tatgaaggct cgagagttat ttcgtaataa gagcgagagc   3540
```

-continued

```
cagtgtgatg aggacggcat gaccagtagc ctttctgaga gcctaaagac agaactgggc   3600
aaagacttgg gtgtggaagc caagattccc ctgaacctag atggccctca cccgtctccc   3660
ccgaccccgg acagtgttgg acagctacat atcatggact acaatgagac tcatcatgaa   3720
cacagctaag gaatgatggt caatcagtgt taacttgcat attgttggca cagaacagga   3780
ggtgtgaatg cacgtttcaa agctttcctg tttccagggt ctgagtgcaa gttcatgtgt   3840
ggaaatggga cggaggtcct ttggacagct gactgaatgc agaacggttt ttggatctgg   3900
cattgaaatg cctcttgacc ttcccctcca cccgccctaa ccccctctca tttacctcgc   3960
agtgtgttct aatccaaggg ccagttggtg ttcctcagta gctttacttt cttcctttcc   4020
cccccaaatg gttgcgtcct ttgaacctgt gcaatatgag gccaaattta atctttgagt   4080
ctaacacacc actttctgct ttcccgaagt tcagataact gggttggctc tcaattagac   4140
caggtagttt gttgcattgc aggtaagtct ggttttgtcc cttccaggag gacatagcct   4200
gcaaagctgg ttgtctttac atgaaagcgt ttacatgaga ctttccgact gctttttga    4260
ttctgaagtt cagcatctaa agcagcaggt ctagaagaac aacggtttat tcatacttgc   4320
attcttttgg cagttctgat aagcttccta gaaagttctg tgtaaacaga agcctgtttc   4380
agaaatctgg agctggcact gtggagacca cacacccttt gggaaagctc ttgtctcttc   4440
ttcccccact acctcttatt tatttggtgt ttgcttgaat gctggtacta ttgtgaccac   4500
aggctggtgt gtaggtggta aaacctgttc tccataggag ggaaggagca gtcactggga   4560
gaggttaccc gagaagcact tgagcatgag gaactgcacc tttaggccat ctcagcttgc   4620
tgggcctttt gttaaaccct tctgtctact ggcctccctt tgtgtgcata cgcctcttgt   4680
tcatgtcagc ttatatgtga cactgcagca gaaaggctct gaaggtccaa agagtttctg   4740
caaagtgtat gtgaccatca tttcccaggc cattagggtt gcctcactgt agcaggttct   4800
aggctaccag aagaggggca gctttttcat accaattcca actttcaggg gctgactctc   4860
cagggagctg atgtcatcac actctccatg ttagtaatgg cagagcagtc taaacagagt   4920
ccgggagaat gctggcaaag gctggctgtg tatacccact aggctgcccc acgtgctccc   4980
gagagatgac actagtcaga aaattggcag tggcagagaa tccaaactca acaagtgctc   5040
ctgaaagaaa cgctagaagc ctaagaactg tggtctggtg ttccagctga ggcaggggga   5100
tttggtagga aggagccagt gaacttggct ttcctgtttc tatctttcat taaaaagaat   5160
agaaggattc agtcataaag aggtaaaaaa ctgtcacggt acgaaatctt agtgcccacg   5220
gaggcctcga gcagagagaa tgaaagtctt tttttttttt tttttttttt agcatggcaa   5280
taaatattct agcatcccta actaaagggg actagacagt tagagactct gtcaccctag   5340
ctataccagc agaaaacctg ttcaggcagg ctttctgggt gtgactgatt cccagcctgt   5400
ggcagggcgt ggtcccaact actcagccta gcacaggctg gcagttggta ctgaattgtc   5460
agatgtggag tattagtgac accacacatt taattcagct ttgtccaaag gaaagcttaa   5520
aacccaatac agtctagttt cctggttccg ttttagaaaa ggaaaacgtg aacaaactta   5580
gaaagggaag gaaatcccat cagtgaatcc tgaaactggt tttaagtgct ttccttctcc   5640
tcatgcccaa gagatctgtg ccatagaaca agataccagg cacttaaagc cttttcctga   5700
attggaaagg aaaagaggcc caagtgcaaa agaaaaaaca ttttagaaac ggacagctta   5760
taaaaataaa gggaagaaag gaggcagcat ggagagaggc ctgtgctaga agctccatgg   5820
acgtgtctgc acagggtcct cagctcatcc atgcggcctg ggtgtccttt tactcagctt   5880
tataacaaat gtggctccaa gctcaggtgc ctttgagttc taggaggctg tgggttttat   5940
```

-continued

```
tcaactacgg ttgggagaat gagacctgga gtcatgttga aggtgcccaa cctaaaaatg   6000
taggctttca tgttgcaaag aactccagag tcagtagtta ggtttggttt ggttttggac   6060
atgataaacc tgccaagagt caacaggtca cttgatcatg ctgcagtggg tagttctaag   6120
gatggaaagg tgacagtatt actctcgaga ggcaattcag tcctgggcaa aggtattagt   6180
acaataagcg ttaagggcag agtctacctt gaaaccaatt aagcagcttg gtattcataa   6240
atattgggat tggatggcct ccatccagaa atcactatgg gtgagcatac ctgtctcagc   6300
tgtttggcca atgtgcataa cctactcgga tccccacctg acactaacca gagtcagcac   6360
aggccccgag gagcccgaag tctgctgctg tgcagcatgg aattccttta aaaaggtgca   6420
ctacagtttt agcggggagg gggataggaa gacgcagagc aaatgagctc cggagtccct   6480
gcaggtgaat aaacacacag atctgcatct gatagaactt tgatggattt tcaaaaagcc   6540
gttgacaagg ctctgctata cagtctataa aaattgttat tatgggattg gaagaaacac   6600
gtggtcatga atagaaaaaa aacaaaccca aaggtaggaa ggtcaaggtc atttcttaga   6660
tggagaagtt gtgaaagatg tccttggaga tgagttttag gaccagcatt actaaggcag   6720
gtgggcagac agtgacctct ctaggtgtgt ccacagagtt tttcaggaga gaaaactgcc   6780
tgacctttgg gactaagctg cggaatcttc ttactaagct tgaagagtgg agaggcgaga   6840
ggtgagctac tttgtgagcc aaagcttatg tgacatggtt ggggaaacag tccaaactgt   6900
tctgagaagg tgaactgtta cgacccagga caattagaaa aattcaccca ccatgccgca   6960
cattactggg taaaagcagg gcagcaggga acaaaactcc agactcttgg gccgtcccca   7020
tttgcaacag cacacatagt ttctggtata tttgttggga aagataaaac tctagcagtt   7080
gttgagggga ggatgtataa aatggtcatg gggatgaaag gatctctgag accacagagg   7140
ctcagactca ctgttaagaa tagaaaactg ggtatgcgtt tcatgtagcc agcagaactg   7200
aagtgtgctg tgacaagcca atgtgaattt ctaccaaata gtagagcata ccacttgaag   7260
aaggaaagaa ccgaagagca aacaaaagtt ctgcgtaatg agactcacct tttctcgctg   7320
aaagcactaa gaggtgggag gaggcctgca caggctggag gagggtttgg gcagagcgaa   7380
gacccggcca ggaccttggt gagatggggt gccgcccacc tcctgcggat actcttggag   7440
agttgttccc ccagggggct ctgcccccacc tggagaagga agctgcctgg tgtggagtga   7500
ctcaaatcag tatacctatc tgctgcacct tcactctcca gggtacatgc tttaaaaccg   7560
acccgcaaca agtattggaa aaatgtatcc agtctgaaga tgtttgtgta tctgtttaca   7620
tccagagttc tgtgacacat gccccccaga ttgctgcaaa gatcccaagg cattgattgc   7680
acttgattaa gcttttgtct gtaggtgaaa gaacaagttt aggtcgagga ctggccccta   7740
ggctgctgct gtgacccttg tcccatgtgg cttgtttgcc tgtccgggac tcttcgatgt   7800
gcccagggga gcgtgttcct gtctcttcca tgccgtcctg cagtccttat ctgctcgcct   7860
gagggaagag tagctgtagc tacaagggaa gcctgcctgg aagagccgag cacctgtgcc   7920
catggcttct ggtcatgaaa cgagttaatg atggcagagg agcttcctcc ccacttcgca   7980
gcgccacatt atccatcctc tgagataagt aggctggttt aaccattgga atggaccttt   8040
cagtggaaac cctgagagtc tgagaacccc cagaccaacc cttccctccc tttccccacc   8100
tcttacagtg tttggacagg agggtatggt gctgctctgt gtagcaagta ctttggctta   8160
tgaaagaggc agccacgcat tttgcactag gaagaatcag taatcacttt tcagaagact   8220
tctatggacc acaaatatat tacggaggaa cagattttgc taagacataa tctagtttta   8280
```

-continued

```
taactcaatc atgaatgaac catgtgtggc aaacttgcag tttaaagggg tcccatcagt   8340

gaaagaaact gattttttt aacggactgc ttttagttaa attgaagaaa gtcagctctt   8400

gtcaaaaggt ctaaactttc ccgcctcaat cctaaaagca tgtcaacaat ccacatcaga   8460

tgccataaat atgaactgca ggataaaatg gtacaatctt agtgaatggg aattggaatc   8520

aaaagagttt gctgtccttc ttagaatgtt ctaaaatgtc aaggcagttg cttgtgttta   8580

actgtgaaca aataaaaatt tattgttttg cactaaa                            8617
```

```
<210> SEQ ID NO 8
<211> LENGTH: 3572
<212> TYPE: DNA
<213> ORGANISM: Homo sapiens

<400> SEQUENCE: 8

acctgcactt ctgggggcgt cgagcctggc ggtagaatct tcccagtagg cggcgcggga     60

gggaaaagag gattgagggg ctaggccggg cggatcccgt cctcccccga tgtgagcagt    120

tttccgaaac cccgtcaggc gaaggctgcc cagagaggtg gagtcggtag cggggccggg    180

aacatgaggc agtctctcct attcctgacc agcgtggttc ctttcgtgct ggcgccgcga    240

cctccggatg acccgggctt cggcccccac cagagactcg agaagcttga ttctttgctc    300

tcagactacg atattctctc tttatctaat atccagcagc attcggtaag aaaaagagat    360

ctacagactt caacacatgt agaaacacta ctaacttttt cagctttgaa aaggcatttt    420

aaattatacc tgacatcaag tactgaacgt tttttcacaaa atttcaaggt cgtggtggtg    480

gatggtaaaa acgaaagcga gtacactgta aaatggcagg acttcttcac tggacacgtg    540

gttggtgagc ctgactctag ggttctagcc cacataagag atgatgatgt tataatcaga    600

atcaacacag atggggccga atataacata gagccacttt ggagatttgt taatgatacc    660

aaagacaaaa gaatgttagt ttataaatct gaagatatca agaatgtttc acgtttgcag    720

tctccaaaag tgtgtggtta tttaaaagtg gataatgaag agttgctccc aaaagggtta    780

gtagacagag aaccacctga agagcttgtt catcgagtga aaagaagagc tgacccagat    840

cccatgaaga acacgtgtaa attattggtg gtagcagatc atcgcttcta cagatacatg    900

ggcagagggg aagagagtac aactacaaat tacttaatag agctaattga cagagttgat    960

gacatctatc ggaacacttc atgggataat gcaggtttta aaggctatgg aatacagata   1020

gagcagattc gcattctcaa gtctccacaa gaggtaaaac ctggtgaaaa gcactacaac   1080

atggcaaaaa gttacccaaa tgaagaaaag gatgcttggg atgtgaagat gttgctagag   1140

caatttagct ttgatatagc tgaggaagca tctaaagttt gcttggcaca cctttttcaca   1200

taccaagatt ttgatatggg aactcttgga ttagcttatg ttggctctcc cagagcaaac   1260

agccatggag gtgtttgtcc aaaggcttat tatagcccag ttgggaagaa aaatatctat   1320

ttgaatagtg gtttgacgag cacaaagaat tatggtaaaa ccatccttac aaaggaagct   1380

gacctggtta caactcatga attgggacat aattttggag cagaacatga tccggatggt   1440

ctagcagaat gtgccccgaa tgaggaccag ggagggaaat atgtcatgta tcccatagct   1500

gtgagtggcg atcacgagaa caataagatg ttttcaaact gcagtaaaca atcaatctat   1560

aagaccattg aaagtaaggc ccaggagtgt tttcaagaac gcagcaataa agtttgtggg   1620

aactcgaggg tggatgaagg agaagagtgt gatcctggca tcatgtatct gaacaacgac   1680

acctgctgca acagcgactg cacgttgaag gaaggtgtcc agtgcagtga caggaacagt   1740

ccttgctgta aaaactgtca gtttgagact gcccagaaga agtgccagga ggcgattaat   1800
```

gctacttgca aaggcgtgtc ctactgcaca ggtaatagca gtgagtgccc gcctccagga 1860
aatgctgaag atgacactgt ttgcttggat cttggcaagt gtaaggatgg gaaatgcatc 1920
cctttctgcg agagggaaca gcagctggag tcctgtgcat gtaatgaaac tgacaactcc 1980
tgcaaggtgt gctgcaggga cctttctggc cgctgtgtgc cctatgtcga tgctgaacaa 2040
aagaacttat ttttgaggaa aggaaagccc tgtacagtag gattttgtga catgaatggc 2100
aaatgtgaga aacgagtaca ggatgtaatt gaacgatttt gggatttcat tgaccagctg 2160
agcatcaata cttttggaaa gtttttagca gacaacatcg ttgggtctgt cctggttttc 2220
tccttgatat tttggattcc tttcagcatt cttgtccatt gtgtggataa gaaattggat 2280
aaacagtatg aatctctgtc tctgtttcac cccagtaacg tcgaaatgct gagcagcatg 2340
gattctgcat cggttcgcat tatcaaaccc tttcctgcgc cccagactcc aggccgcctg 2400
cagcctgccc ctgtgatccc ttcggcgcca gcagctccaa aactggacca ccagagaatg 2460
gacaccatcc aggaagaccc cagcacagac tcacatatgg acgaggatgg gtttgagaag 2520
gaccccttcc caaatagcag cacagctgcc aagtcatttg aggatctcac ggaccatccg 2580
gtcaccagaa gtgaaaaggc tgcctccttt aaactgcagc gtcagaatcg tgttgacagc 2640
aaagaaacag agtgctaatt tagttctcag ctcttctgac ttaagtgtgc aaaatatttt 2700
tatagatttg acctacaaat caatcacagc ttgtattttg tgaagactgg gaagtgactt 2760
agcagatgct ggtcatgtgt ttgaacttcc tgcaggtaaa cagttcttgt gtggtttggc 2820
ccttctcctt ttgaaaaggt aaggtgaagg tgaatctagc ttattttgag gctttcaggt 2880
tttagttttt aaaatatctt ttgacctgtg gtgcaaaagc agaaaataca gctggattgg 2940
gttatgaata tttacgtttt tgtaaattaa tcttttatat tgataacagc actgactagg 3000
gaaatgatca gttttttttt atacactgta atgaaccgct gaatatgagg catttggcat 3060
ttatttgtga tgacaactgg aatagttttt tttttttttt tttttttttg ccttcaacta 3120
aaaacaaagg agataaatct agtatacatt gtctctaaat tgtgggtcta tttctagtta 3180
ttacccagag tttttatgta gcagggaaaa tatatatcta aatttagaaa tcatttgggt 3240
taatatggct cttcataatt ctaagactaa tgctctctag aaacctaacc acctacctta 3300
cagtgagggc tatacatggt agccagttga atttatggaa tctaccaact gtttagggcc 3360
ctgatttgct gggcagtttt tctgtatttt ataagtatct tcatgtatcc ctgttactga 3420
tagggataca tgctcttaga aaattcacta ttggctggga gtggtggctc atgcctgtaa 3480
tcccagcact tggagaggct gaggttgcgc cactacactc cagcctgggt gacagagtga 3540
gactctgcct caaaaaaaaa aaaaaaaaaa aa 3572

<210> SEQ ID NO 9
<211> LENGTH: 716
<212> TYPE: DNA
<213> ORGANISM: Homo sapiens

<400> SEQUENCE: 9
aggccgctat cgagcagggt ccgagggctg tgtcagaagg ctgggcagcc atggcgtcct 60
atttcgatga acacgactgc gagccgtcgg accctgagca ggagacgcga accaacatgc 120
tgctggagct cgcaaggtca cttttcaata ggatggactt tgaagacttg ggttggtag 180 tagattggga ccaccacctg cctccaccag ctgccaagac tgtggttgag aacctcccca 240
ggacagtcat cagaggctct caggctgagc tcaagtgccc cgtgtgtctt ttggaatttg 300

```
aggaggagga gactgccatt gagatgcctt gccatcacct tttccattcc agctgcattc    360

tgccctggct aagcaagaca aattcctgtc ccttgtgccg ctatgagctg cccactgatg    420

acgacactta tgaggagcac agacgagata aggctcgaaa acagcagcag caacaccgac    480

tggagaacct ccatggagcc atgtacacgt gaggaggttg gggctgagtg ctggccctct    540

gcgtcttcct tattaacctt gaatcctcat taaaggtttc tttacccacc ctgaggctgt    600

attgatcaca gacctggcca ggggctctgc atcctccatc aggtctctac ttctgttggg    660

gaaggtgatc ctaaatcgca gaaggcacca ggctgcggtt ttcctccctg ctggcc        716


<210> SEQ ID NO 10
<211> LENGTH: 4757
<212> TYPE: DNA
<213> ORGANISM: Homo sapiens

<400> SEQUENCE: 10

agagtgcgcc cgggccgcgg atccccaagc ccgccacgcc gcccagcccg gccccgcccg     60

cgccggaaga gccacgccgg ccctgggcag tgacggggtt cgggtgacca tggagagtgc    120

gctcaccgcc cgtgaccggg tgggggtgca ggatttcgtg ctgctggaga acttcaccag    180

cgaggccgcc ttcatcgaga acctgcggcg gcgatttcgg gagaatctca tctacaccta    240

cattggcccc gtcctggtct ctgtcaatcc ctaccgggac ctgcagatct acagccggca    300

gcatatggag cgttaccgtg gcgtcagctt ctatgaagtg ccccctcacc tgtttgccgt    360

ggcggacact gtgtaccgag cactgcgcac ggagcgtcgg gaccaggctg tgatgatctc    420

tggggagagc ggggcaggca agaccgaggc caccaagagg ctgctgcagt tctatgcaga    480

gacctgccca gcccccgagc gcggaggtgc cgtgcgggac cggctgctac agagcaaccc    540

ggtgctggag gcctttggaa atgccaagac cctccggaac gataactcca gcaggttcgg    600

gaagtacatg gatgtgcagt ttgacttcaa gggtgccccc gtgggtggcc acatcctcag    660

ttacctcctg gaaaagtcac gagtggtgca ccagaatcat ggggagcgga acttccacat    720

cttctaccag ctgctggagg ggggcgagga ggagactctt cgcaggctgg gcttggaacg    780

gaacccccag agctacctgt acctggtgaa gggccagtgt gccaaagtct cctccatcaa    840

cgacaagagt gactggaagg tcgtcaggaa ggctctgaca gtcattgatt tcaccgagga    900

tgaagtggag gacctgctga gcatcgtggc cagcgtcctt catttgggca acatccactt    960

tgctgccaac gaggagagca atgcccaggt caccaccgag aaccagctca agtatctgac   1020

caggctcctc agcgtggaag gctcgacgct gcgagaagcc ctgacacaca ggaagatcat   1080

cgccaagggg gaggagctcc tgagcccgct gaacctggag caggccgcgt acgcacgaga   1140

cgccctcgcc aaggctgtgt acagccgcac ttttacctgg ctcgtcggga agatcaacag   1200

gtcgctggcc tccaaggacg tggagagccc cagctggcgg agcaccacgg ttctcgggct   1260

cctggatatt tatggctttg aagtgtttca gcataacagc tttgagcagt tctgcatcaa   1320

ttactgcaac gagaagctgc agcagctctt catcgagctc acgctcaagt cggagcagga   1380

ggagtacgag gcagagggca tcgcgtggga gcccgtccag tatttcaaca acaaaatcat   1440

ctgtgatctg gtggaggaga agtttaaggg catcatctcg attttggatg aggagtgtct   1500

gcgccccggg gaggccacag acctgacctt cctggagaag ctggaggata ctgtcaagca   1560

ccatccacac ttcctgacgc acaagctggc tgaccagcgg accaggaaat ctctgggccg   1620

aggggaattc cgccttctgc actatgcggg ggaggtgacc tacagcgtga ccgggtttct   1680

ggacaaaaac aatgaccttc tcttccggaa ccttaaggag accatgtgta gctcaaagaa   1740
```

-continued

```
tcccattatg agccagtgct ttgaccggag cgagctcagt gacaagaagc ggccagagac   1800
ggtcgccacc cagttcaaga tgagcctcct gcagctggtg gagatcctgc agtctaagga   1860
gcccgcctac gtccgctgca tcaaacccaa tgatgccaaa cagcccggcc gctttgacga   1920
ggtgctgatc cgccaccagg tgaagtacct ggggctgttg gaaaacctgc gcgtgcgcag   1980
agccggcttt gcctatcgcc gcaaatacga agctttcctg caaaggtaca agtcactgtg   2040
cccagagacg tggcccacgt gggcaggacg gccgcaggat ggggtggctg tgctggtccg   2100
acacctgggc tacaagccag aagagtacaa gatgggcagg accaagatct tcatccgctt   2160
ccccaagacc ctgtttgcca cagaggatgc cctggaggtc cggcggcaga gcctggccac   2220
aaagatccaa gctgcctgga ggggctttca ctggcggcag aaattcctcc gggtgaagag   2280
atcagccatc tgcatccagt cgtggtggcg tggaacactg ggccggagga aggcagccaa   2340
gaggaagtgg gcggcacaga ccatccggcg gctcatccga ggcttcgtcc tgcgccacgc   2400
cccccgctgc cccgagaacg ccttcttcct ggaccatgtg cgcacctctt ttttgctaaa   2460
cctgaggcgg cagctgcccc agaatgtcct ggacacctcg tggcccacgc ccccacctgc   2520
cctgcgtgag gcctcagagc ttctgcggga gttgtgcata aagaacatgg tgtggaaata   2580
ctgccggagt atcagccctg agtggaagca gcagctgcag cagaaggccg tggctagtga   2640
gatcttcaag ggcaagaagg ataattaccc tcagagtgta cccaggctct tcatcagcac   2700
tcggcttggt acagatgaga tcagcccccg agtgctgcag gccttgggct ctgagcccat   2760
tcagtatgcg gtgcctgttg tgaaatacga ccgcaagggc tacaagcctc gctcccggca   2820
gctgctgctc acgcccaacg ccgtcgtcat cgtggaggac gccaaagtca agcagaggat   2880
tgattacgcc aacctgaccg gaatctctgt cagcagcctg agcgacagtc tttttgtgct   2940
tcatgtacag cgtgcggaca ataagcaaaa gggagatgtg gtgctgcaga gtgaccacgt   3000
gattgagacg ctgaccaaga cagccctcag tgccaaccgc gtgaacagca tcaacatcaa   3060
ccagggcagc atcacgtttg caggggggccc cggcagggat ggcaccattg acttcacacc   3120
cggctcggag ctgctcatca ccaaggccaa gaacgggcac ctggctgtgg tcgccccacg   3180
gctgaattct cggtgataaa ggcgcccact ggaccctccc aacgcccaat gctttgcttt   3240
tctcctcctc cccttcccag ttaccaaaga ctcgaacttc cagacaggga cccagggaca   3300
ccccgaagcc cacctgcaat ctcccacctc ctgcccatcc ctctcttgag ggagcagcag   3360
gggccaggag ctaccccagg agtgggccag gccgggccac agcaatagga aagccagggc   3420
cagagcgagc catgccagcc ctactgccga tgccaaatat ttgagagaag ggaacttttg   3480
ctgaggtttt ctctgaggtt tttttgatgc tttataggaa actatttttt aaaaaaagcc   3540
atttcccacc caaggacaca gtggatgtgt tttccctgac tccagcaggg caaggaatgt   3600
agccgagagg ttgtgtgggc tgggctctgg tgccctcttc cctggccagg acacctctcc   3660
tcctgattcc cttggcacct tgtctttctg tctgtttacc tgtctccctg cctgcccatc   3720
tgcatctttt gcagcccact ctgacttcca tctgggggct gagaccaccc ttgcctgccc   3780
ccttctttct gccttaagaa tgtcctttta ggctgggcat ggtggctcac gcctgtaacc   3840
ccagcacttt gggaggcgga gacgggcaga taacctgagg tcaggatttc gagaccaacc   3900
tgacctacat ggagaaactc cgcctctagt aaaaatacaa aattagccgg gcatggtggt   3960
gcacgcctct aatcccagct actcgggagg ctgaggcagg agaatcactt gaacccggga   4020
agtggaggtt gcagtgagcc aagagtacac cactgcactc cagcctgggc aacagagcga   4080
```

-continued

```
gactccgtct taaaaaaaaa aaaaaagaac gccctttac tgtcctcatc atcccagttt   4140

gaggcagtgc tggagtgggg aaggccgtct tagaccatag aggttggaag acgctgagag   4200

atcatccagc ccagcccctt gatgttacag agcagaagac agatgcccaa acaggagaag   4260

gcacttgccc acggtcatac ggcaggttgc cacaaaacca agatggcagc ccttcctcag   4320

cgtgcctcac tgccactccc agagccaggg agccccataa aacccacatc atgtcttaag   4380

agtatatctg gctccttgac cagcaatcgg ccctgggagc caccaggtgg gaaaagcgcc   4440

tctgccagag tccaggcctt gggatgacag acagcttgcc cgcacactcg ggccccactc   4500

aaggatgtag ggccttttct ggcccctgac ccctccctgg catgggagcg tggggacggg   4560

gctggccttg ggaggagcgg caggggcatc acctccttct gctgcttctc cctgctccta   4620

ccctcaaggg cctgggggct gcccagctgc ctctatgccc ttctgggggt ctcagcccac   4680

tgctgacact tctgcaatcc agagaaacac taaataaagc aatacgtgtt tgccaaaaaa   4740

aaaaaaaaaa aaaaaaa                                                 4757
```

<210> SEQ ID NO 11
<211> LENGTH: 1336
<212> TYPE: DNA
<213> ORGANISM: Homo sapiens

<400> SEQUENCE: 11

```
gcgaggtggg gtaggcgggc aaggcgggcg ccgaggtttg caaaggctcg cagcggccag     60

aaacccggct ccgagcggcg gcggcccggc ttccgctgcc cgtgagctaa ggacggtccg    120

ctccctctag ccagctccga atcctgatcc aggcgggggc caggggcccc tcgcctcccc    180

tctgaggacc gaagatgagc ttcctcttca gcagccgctc ttctaaaaca ttcaaaccaa    240

agaagaatat ccctgaagga tctcatcagt atgaactctt aaaacatgca gaagcaactc    300

taggaagtgg gaatctgaga caagctgtta tgttgcctga gggagaggat ctcaatgaat    360

ggattgctgt gaacactgtg gatttcttta accagatcaa catgttatat ggaactatta    420

cagaattctg cactgaagca agctgtccag tcatgtctgc aggtccgaga tatgaatatc    480

actgggcaga tggtactaat attaaaaagc caatcaaatg ttctgcacca aaatacattg    540

actatttgat gacttgggtt caagatcagc ttgatgatga aactcttttt ccttctaaga    600

ttggtgtccc atttcccaaa aactttatgt ctgtggcaaa gactattcta aagcgtctgt    660

tcagggttta tgcccatatt tatcaccagc actttgattc tgtgatgcag ctgcaagagg    720

aggcccacct caacacctcc tttaagcact ttattttctt tgttcaggag tttaatctga    780

ttgataggcg tgagctggca cctcttcaag aattaataga gaaacttgga tcaaaagaca    840

gataaatgtt tcttctagaa cacagttacc cccttgcttc atctattgct agaactatct    900

cattgctatc tgttatagac tagtgataca aactttaaga aaacaggata aaaagatacc    960

cattgcctgt gtctactgat aaaattatcc caaaggtagg ttggtgtgat agtttccgag   1020

taagacctta aggacacagc caaatcttaa gtactgtgtg accactcttg ttgttatcac   1080

atagtcatac ttggttgtaa tatgtgatgg ttaacctgta gcttataaat ttacttatta   1140

ttcttttact catttactca gtcatttctt tacaagaaaa tgattgaatc tgttttaggt   1200

gacagcacaa tggacattaa gaatttccat caataattta tgaataagtt tccagaacaa   1260

atttcctaat aacacaatca gattggtttt attcttttat tttacgaata aaaaatgtat   1320

ttttcagtaa aaaaaa                                                   1336
```

-continued

<210> SEQ ID NO 12
<211> LENGTH: 2324
<212> TYPE: DNA
<213> ORGANISM: Homo sapiens

<400> SEQUENCE: 12
acatcgggaa gccggaatta cttgcagggc taacctagtg cctatagcta aggcaggtac 60
ctgcatcctt gtttttgttt agtggatcct ctatccttca gagactctgg aacccctgtg 120
gtcttctctt catctaatga ccctgagggg atggagtttt caagtccttc cagagaggaa 180
tgtcccaagc ctttgagtag ggtaagcatc atggctggca gcctcacagg attgcttcta 240
cttcaggcag tgtcgtgggc atcaggtgcc cgcccctgca tccctaaaag cttcggctac 300
agctcggtgg tgtgtgtctg caatgccaca tactgtgact cctttgaccc cccgaccttt 360
cctgcccttg gtaccttcag ccgctatgag agtacacgca gtgggcgacg gatggagctg 420
agtatggggc ccatccaggc taatcacacg ggcacaggcc tgctactgac cctgcagcca 480
gaacagaagt tccagaaagt gaagggattt ggaggggcca tgacagatgc tgctgctctc 540
aacatccttg ccctgtcacc ccctgcccaa aatttgctac ttaaatcgta cttctctgaa 600
gaaggaatcg gatataacat catccgggta cccatggcca gctgtgactt ctccatccgc 660
acctacacct atgcagacac ccctgatgat ttccagttgc acaacttcag cctcccagag 720
gaagatacca agctcaagat acccctgatt caccgagccc tgcagttggc ccagcgtccc 780
gtttcactcc ttgccagccc ctggacatca cccacttggc tcaagaccaa tggagcggtg 840
aatgggaagg ggtcactcaa gggacagccc ggagacatct accaccagac ctgggccaga 900
tactttgtga agttcctgga tgcctatgct gagcacaagt tacagttctg ggcagtgaca 960
gctgaaaatg agccttctgc tgggctgttg agtggatacc ccttccagtg cctgggcttc 1020
acccctgaac atcagcgaga cttcattgcc cgtgacctag gtcctaccct cgccaacagt 1080
actcaccaca atgtccgcct actcatgctg gatgaccaac gcttgctgct gccccactgg 1140
gcaaaggtgg tactgacaga cccagaagca gctaaatatg ttcatggcat tgctgtacat 1200
tggtacctgg actttctggc tccagccaaa gccaccctag gggagacaca ccgcctgttc 1260
cccaacacca tgctctttgc ctcagaggcc tgtgtgggct ccaagttctg ggagcagagt 1320
gtgcggctag gctcctggga tcgagggatg cagtacagcc acagcatcat cacgaacctc 1380
ctgtaccatg tggtcggctg gaccgactgg aaccttgccc tgaaccccga aggaggaccc 1440
aattgggtgc gtaactttgt cgacagtccc atcattgtag acatcaccaa ggacacgttt 1500
tacaaacagc ccatgttcta ccaccttggc cacttcagca agttcattcc tgagggctcc 1560
cagagagtgg ggctggttgc cagtcagaag aacgacctgg acgcagtggc actgatgcat 1620
cccgatggct ctgctgttgt ggtcgtgcta aaccgctcct ctaaggatgt gcctcttacc 1680
atcaaggatc ctgctgtggg cttcctggag acaatctcac ctggctactc cattcacacc 1740
tacctgtggc gtcgccagtg atggagcaga tactcaagga ggcactgggc tcagcctggg 1800
cattaaaggg acagagtcag ctcacacgct gtctgtgact aaagagggca cagcagggcc 1860
agtgtgagct tacagcgacg taagcccagg ggcaatggtt tgggtgactc actttcccct 1920
ctaggtggtg ccaggggctg gaggccccta gaaaaagatc agtaagcccc agtgtccccc 1980
cagcccccat gcttatgtga acatgcgctg tgtgctgctt gctttggaaa ctgggcctgg 2040
gtccaggcct agggtgagct cactgtccgt acaaacacaa gatcagggct gagggtaagg 2100
aaaagaagag actaggaaag ctgggcccaa aactggagac tgtttgtctt tcctggagat 2160

-continued

```
gcagaactgg gcccgtggag cagcagtgtc agcatcaggg cggaagcctt aaagcagcag   2220

cgggtgtgcc caggcaccca gatgattcct atggcaccag ccaggaaaaa tggcagctct   2280

taaaggagaa aatgtttgag cccaaaaaaa aaaaaaaaaa aaaa                    2324
```

<210> SEQ ID NO 13
<211> LENGTH: 1611
<212> TYPE: DNA
<213> ORGANISM: Homo sapiens

<400> SEQUENCE: 13

```
gagggtgccg ggcgtcacag gtcctgacag ggaagaagtt ggcaggtcct ggcaggggac     60

gagctgcggc ggtggcacct ccgggtgtgg aaggctccag tgagatggag tcgcgagtcg    120

cggacgctgg gaccggcgag accgcgcgag cagcgggcgg gagtccggca gttggctgca    180

ccactcgggg gcccgtagtc tcggcgcccc tgggagccgc ccggtggaag ctcctgcggc    240

aggttctgaa gcaaaaacac ctggatgatt gcctgcgaca tgtatctgta agaagatttg    300

aatcatttaa tctgttttca gtaacagaag gcaaagaaag ggaaactgaa gaggaggttg    360

gtgcatgggt ccaatataca agcatcttct gtcctgaata cagtatctcc ttaaggcata    420

atagtggatc cttgaatgtt gaagatgtcc ttaccagctt tgacaataca ggaaatgttt    480

gcatctggcc atctgaagag gttttggctt actactgcct caagcacaat aatatattca    540

gggcccttgc tgtgtgtgag ctagggggtg gcatgacatg cttggctggg ctcatggttg    600

ctatttctgc agatgtcaaa gaagttctgt taactgatgg gaatgaaaag gccatcagaa    660

atgtgcaaga catcatcaca aggaatcaga aggctggtgt gtttaagacc cagaaaatat    720

caagctgcgt tttacgatgg gataatgaga cagatgtctc tcaactggaa ggacattttg    780

acattgttat gtgtgctgac tgcctgtttc tggaccagta cagagccagc cttgttgatg    840

caataaagag attactccag cccaggggga aagcgatggt atttgcccca cgccgaggga    900

atactttaaa ccagttttgc aatctagctg aaaaagctgg tttctgtatc caaagacatg    960

aaaattatga tgaacacatt tcaaacttcc actccaagtt gaaaaaggaa aacccggaca   1020

tatatgaaga aaaccttcat tacccgcttc tgcttatttt gaccaaacat ggatagaaga   1080

ttaagcttct caaagacgaa gaaacgtatc aagtgcatag ggaatatttt tacaaaaacg   1140

gaaatctgta aggggtataa tcgcctgcct gcgccctttg cagcatttca cgtgtgggct   1200

atggactcca cctgtcctca cccacgttat tccccagctg ccctctccag ctccctcccc   1260

gcctcttttt acactctgct tgttgctcgt cctgccctaa acctttgttt gtctttaaat   1320

gtgtataagc tgcctgtctg tgacttgaat ttgactggtg aacaaactaa atatttttcc   1380

ctgtaattga gacagaattt cttttgatga tacccatccc tccttcattt tttttttttt   1440

tttggtcttt gttctgtttt ggtggtggta gtttttaatc agtaaaccca gcaaatatca   1500

tgattctttc ctggttagaa aaataaataa agtgtatctt tttatctccc tcccaaaaaa   1560

aaaaaaaaaa aaaaaaaaaa aaaaaaaaaa aaaaaaaaaa aaaaaaaaaa a            1611
```

<210> SEQ ID NO 14
<211> LENGTH: 1202
<212> TYPE: DNA
<213> ORGANISM: Homo sapiens

<400> SEQUENCE: 14

```
ggaagggtga tgtggctgcg gcatcgccgg cctcgctatg tctgccattt tcaattttca     60

gagtctattg actgtaatct tgctgcttat atgtacctgt gcttatattc gatccttggc    120
```

```
acccagcctc ctggacagaa ataaaactgg attgttgggt atattttgga agtgtgccag    180
aattggtgaa cggaagagtc cttatgttgc agtatgctgt atagtaatgg ccttcagcat    240
cctcttcata cagtagctgg ggaaaatgcc agaatgtagt tgccatcaga tttgattgtg    300
aacaaggact gactgcagaa aataatggaa aggatgttta actcttttat ctccgaacat    360
tgaatgagat aaatttccag atgctgttct ctattttaat gttattggac caatgttctg    420
tataaacaat taagatgtaa ccatttaata gtctgtaaca atcaacctca gtactgtcac    480
tacaatatta cattctgcaa atgttattct gttgtatcag atacaaaatt ttagtgaggt    540
atctctaagg cacatagtag aaaacaaaat tggttaatta ctcaagttcc tttcactgtg    600
atttggaaat gatttaatct ttatagaatg agaacctttt ttggactagc tttttttatta    660
aaatggctca atttgtgttg ataaggattg cattaatatt taatagtgct tgcttttcct    720
ctgggcacac cattttgatc attaaccaga gtacctctac tcttagcaaa ctctagttta    780
tgacaagtat ttaaaatatt taaaacaagc ttatgcagtt cttaaggacg aaggtaaatg    840
agatgtaact taaaaatagt attgggaaaa tgttgatagt taacattagt ggatttagac    900
tagccaaatg acatagtagg ctctgaaaca tcttgtcaag tatatgtatt ttgtgcatga    960
atttttgctg gaaagctgtc tttctctgaa aaacacaacg ttcttagaat gaaaagaaca   1020
attataaaat aattatccta tatgtgtttt tcattctttt tagtgtcatg gcttcaaaaa   1080
tgaaacattt attttaattg ccgtaaagga actgtatttt tgttttgttt tttaacacag   1140
cactttaaat ccagtttgtg ttttgtcaac ttgcaaaaaa aaaaaaaaaa aaaaaaaaaa   1200
aa                                                                  1202
```

```
<210> SEQ ID NO 15
<211> LENGTH: 7586
<212> TYPE: DNA
<213> ORGANISM: Homo sapiens

<400> SEQUENCE: 15
```

```
gtgctgaagt agaggtagta cagcatggct agactgttgt gagaggctca gagaaagcag     60
agggtgagat ggatgagtcc agcattctaa gacgaagagg gctccagaag gagctgagtc    120
tccccagaag aggaagtttg atagattccc agaagtggaa ttgcttggtc aaacgttgcc    180
gaacaagcaa ccggaaaagc ttaataggca atgggcagtc accagcattg cctcgaccac    240
actcacctct ctctgctcat gcaggaaata gccctcaaga tagtccaaga aatttctccc    300
ccagtgcctc agcccatttt tcatttgcac ggaggactga tggacgccgc tggtcgttgg    360
cttctctccc ttcctctggc tatgggacaa acacacccag ctctacggtc tcttcatcct    420
gttcctccca ggagaagttg catcagttac cataccaacc aacaccagac gagttacact    480
tcttatcaaa acatttctgt accaccgaaa gcatcgccac tgagaacaga tgcaggaaca    540
cgccgatgcg cccccgttcc cgaagtctga gccctggacg ttctcccgcc tgctgtgacc    600
atgaaataat tatgatgaac catgtctaca aagaaaggtt cccaaaggct acagctcaga    660
tggaagaacg tctaaaggaa attatcacca gctactctcc tgacaacgtt ctacccttag    720
cagatggagt gcttagtttc actcaccacc agattattga actggctcga gattgcttgg    780
ataaatccca ccagggcctc atcacctcac gatacttcct tgaattacag cacaaattag    840
ataagttgct acaggaggct catgatcgtt cagaaagtgg agaattggca tttattaaac    900
aactagttcg aaagatccta attgttattg cccgccctgc tcggttatta gagtgcctgg    960
```

-continued aatttgatcc ggaagaattt tactacctat tggaagcagc agaaggccat gccaaagaag 1020
gacagggtat taaaaccgac attcccaggt acatcattag ccaactggga ctcaataagg 1080
atcccttgga agaaatggct catttgggaa actacgatag tgggacagca gaaacaccag 1140
aaacagatga atcagtgagt agctctaatg cctccctgaa acttcgaagg aaacctcggg 1200
aaagtgattt tgaaacgatt aaattgatta gcaatggagc ctatggggca gtctactttg 1260
ttcggcataa agaatcccgg cagaggtttg ccatgaagaa gattaataaa cagaacctca 1320
tccttcgaaa ccagatccag caggcctttg tggagcggga tatcctgact tttgcagaaa 1380
accccttgt tgtcagcatg tattgctcct ttgaaacaag gcgccacttg tgcatggtca 1440
tggaatatgt ggaaggggga gactgtgcta ctttaatgaa aaacatgggt cctctccctg 1500
ttgatatggc cagaatgtac tttgctgaga cggtcttggc cttggaatat ttacataatt 1560
atggaattgt acacagggat ttgaaaccag acaacttgtt ggttacctcc atggggcaca 1620
taaagctgac agattttgga ttatctaagg tgggactaat gagcatgact accaaccttt 1680
acgagggtca tattgagaag gatgctagag agttcctgga taaacaggtc tgtggcacac 1740
ctgaatacat tgcaccagaa gtgattctga ggcagggtta tggaaagccg gtggactggt 1800
gggccatggg gattatcctc tatgaatttc tggttggatg cgtgccattc tttggggata 1860
ctccagagga gctatttgga caagtcatca gtgatgagat caactggcct gagaaggatg 1920
aggcaccccc acctgatgcc caggatctga ttaccttact cctcaggcag aatcccctgg 1980
agaggctggg aacaggtggt gcatatgaag tcaaacagca tcgattcttc cgttctttag 2040
actggaacag tttgctgaga cagaaggcag aatttattcc ccaactggaa tctgaggatg 2100
acacaagtta ttttgatact cggtctgaga agtatcatca tatggaaacg gaggaagaag 2160
atgacacaaa tgatgaagac tttaatgtgg aaataaggca gttttcttca tgttcacaca 2220
ggttttcaaa agttttcagc agtatagatc gaatcactca gaattcagca gaagagaagg 2280
aagactctgt ggacaaaacc aaaagcacca ccttgccatc cacagaaaca ctgagctgga 2340
gttcagaata ttctgaaatg caacagctat caacatccaa ctcttcagat actgaaagca 2400
acagacataa actcagttct ggcctacttc ccaaactggc tatttcaaca gagggagagc 2460
aagatgaagc tgcctcctgc cctggagacc cccatgagga gccaggaaag ccagcccttc 2520
ctcctgaaga gtgtgcccag gaggagcctg aggtcaccac cccagccagc accatcagca 2580
gctccaccct gtcagttggc agtttttcag agcacttgga tcagataaat ggacgaagcg 2640
agtgtgtgga cagtacagat aattcctcaa agccatccag tgaacccgct tctcacatgg 2700
ctcggcagcg attagaaagc acagaaaaaa agaaaatctc ggggaaagtc acaaagtccc 2760
tctctgccag tgctctttcc ctcatgatcc caggagatat gtttgctgtt tcccctctgg 2820
gaagtccaat gtctccccat tccctgtcct cggacccttc ttcttcacga gattcctctc 2880
ccagccgaga ttcctcagca gcttctgcca gtccacatca gccgattgtg atccacagtt 2940
cggggaagaa ctacggcttt accatccgag ccatccgggt gtatgtggga gacagtgaca 3000
tctatacagt gcaccatatc gtctggaatg tagaagaagg aagtccggca tgccaggcag 3060
gactgaaggc tggagatctt atcactcaca tcaatggaga accagtgcat ggacttgtcc 3120
acacagaagt tatagaactc ctactgaaga gtgggaataa ggtgtcaatc actactaccc 3180
catttgaaaa cacatcaatc aaaactggac cagccaggag aaacagctat aagagccgga 3240
tggtgaggcg gagcaagaaa tccaagaaga aagaaagtct cgaaaggagg agatctcttt 3300
tcaaaaagct agccaagcag ccttctcctt tactccacac cagccgaagt ttctcctgct 3360

-continued

```
tgaacagatc cctgtcatcg ggtgagagcc tcccaggttc ccccactcat agcttgtctc   3420
cccggtctcc aacaccaagc taccgctcca cccctgactt cccatctggt actaattcct   3480
cccagagcag ctcccctagt tctagtgccc ccaattcccc agcagggtcc gggcacatcc   3540
ggcccagcac tctccacggt cttgcaccca aactcggcgg gcagcggtac cggtccggaa   3600
ggcgaaagtc cgccggcaac atcccactgt ccccgctggc ccggacgccc tctccaaccc   3660
cgcaacccac ctccccgcag cggtcaccat cccctcttct gggacactca ctgggcaatt   3720
ccaagatcgc gcaagccttt cccagcaaga tgcactcccc gcccaccatc gtcagacaca   3780
tcgtgaggcc caagagtgcg gagcccccca ggtccccgct gctcaagcgc gtgcagtccg   3840
aggagaagct gtcgccctct tacggcagtg acaagaagca cctgtgctcc cgcaagcaca   3900
gcctggaggt gacccaagag gaggtgcagc gggagcagtc ccagcgggag gcgccgctgc   3960
agagcctgga tgagaacgtg tgcgacgtgc cgccgctcag ccgcgcccgg ccagtggagc   4020
aaggctgcct gaaacgccca gtctcccgga aggtgggccg ccaggagtct gtggacgacc   4080
tggaccgcga caagctgaag gccaaggtgg tggtgaagaa agcagacggc ttcccagaga   4140
aacaggaatc ccaccagaaa tcccatggac ccgggagtga tttggaaaac tttgctctgt   4200
ttaagctgga agagagagag aagaaagtct atccgaaggc tgtggaaagg tcaagtactt   4260
ttgaaaacaa agcgtctatg caggaggcgc caccgctggg cagcctgctg aaggatgctc   4320
ttcacaagca ggccagcgtg cgcgccagcg agggtgcgat gtcggatggc cgggtgcctg   4380
cggagcaccg ccagggtggc ggggacttca gacgggcccc cgctcctggc accctccagg   4440
atggtctctg ccactccctc gacaggggca tctctgggaa gggggaaggc acggagaagt   4500
cctcccaggc caaggagctt ctccgatgtg aaaagttaga cagcaagctg gccaacatcg   4560
attacctccg aaagaaaatg tcacttgagg acaaagagga caacctctgc cctgtgctga   4620
agcccaagat gacagctggc tcccacgaat gcctgccagg gaacccagtc cgacccacgg   4680
gtgggcagca ggagcccccg ccggcttctg agagccgagc ttttgtcagc agcacccatg   4740
cagctcagat gagtgccgtc tcttttgttc ccctcaaggc cttaacaggc cgggtggaca   4800
gtggaacgga gaagcctggc ttggttgctc ctgagtcccc tgttaggaag agcccctccg   4860
agtataagct ggaaggtagg tctgtctcat gcctgaagcc gatcgagggc actctggaca   4920
ttgctctcct gtccggacct caggcctcca agacagaact gccttcccca gagtctgcac   4980
agagccccag cccaagtggt gacgtgaggg cctctgtgcc accagttctc cccagcagca   5040
gtgggaaaaa gaacgatacc accagtgcaa gagagctttc tccttccagc ttaaagatga   5100
ataaatccta cctgctggag ccttggttcc tgcccccag ccgaggtctc cagaattcac   5160
cagcagtttc cctgcctgac ccagagttca agagggacag gaaaggtccc catcctactg   5220
ccaggagccc tggaacagtc atggaaagca atccccaaca gagagagggc agctccccta   5280
aacaccaaga ccacaccact gaccccaagc ttctgacctg cctggggcag aacctccaca   5340
gccctgacct ggccaggcca cgctgcccgc tcccacctga agcttccccc tcaagggaga   5400
agccaggcct gagggaatcg tctgaaagag gccctcccac agccagaagc gagcgctctg   5460
ctgcgagggc tgacacatgc agagagccct ccatggaact gtgctttcca gaaactgcga   5520
aaaccagtga caactccaaa aatctcctct ctgtgggaag gacccaccca gatttctata   5580
cacagaccca ggccatggag aaagcatggg cgccgggtgg gaaaacgaac cacaaagatg   5640
gcccaggtga ggcgaggccc ccgcccagag acaactcctc tctgcactca gctggaattc   5700
```

-continued cctgtgagaa ggagctgggc aaggtgaggc gtggcgtgga acccaagccc gaagcgcttc 5760
ttgccaggcg gtctctgcag ccacctggaa ttgagagtga gaagagtgaa aagctctcca 5820
gtttcccatc tttgcagaaa gatggtgcca aggaacctga aaggaaggag cagcctctac 5880
aaaggcatcc cagcagcatc cctccgcccc ctctgacggc caaagacctg tccagcccgg 5940
ctgccaggca gcattgcagt tccccaagcc acgcttctgg cagagagccg ggggccaagc 6000
ccagcactgc agagcccagc tcgagccccc aggaccctcc caagcctgtt gctgcgcaca 6060
gtgaaagcag cagccacaag ccccggcctg gccctgaccc gggccctcca aagactaagc 6120
accccgaccg gtccctctcc tctcagaaac caagtgtcgg ggccacaaag ggcaaagagc 6180
ctgccactca gtccctcggt ggctctagca gagaggggaa gggccacagt aagagtgggc 6240
cggatgtgtt tcctgctacc ccaggctccc agaacaaagc cagcgatggg attggccagg 6300
gagaaggtgg gccctctgtc ccactgcaca ctgacagggc tcctctagac gccaagccac 6360
aacccaccag tggtgggcgg cccctggagg tgctggagaa gcctgtgcat ttgccaaggc 6420
cgggacaccc agggcctagt gagccagcgg accagaaact gtccgctgtt ggtgaaaagc 6480
aaaccctgtc tccaaagcac cccaaaccat ccactgtgaa agattgcccc accctgtgca 6540
aacagacaga caacagacag acagacaaaa gcccgagtca gccggccgcc aacaccgaca 6600
gaagggcgga agggaagaaa tgcactgaag cactttatgc tccagcagag ggcgacaagc 6660
tcgaggccgg cctttccttt gtgcatagcg agaaccggtt gaaaggcgcg gagcggccag 6720
ccgcgggggt ggggaagggc ttccctgagg ccagagggaa agggcccggt ccccagaagc 6780
caccgacgga ggcagacaag cccaatggca tgaaacggtc cccctcagcc actgggcaga 6840
gttctttccg atccacggcc ctcccggaaa agtctctgag ctgctcctcc agcttccctg 6900
aaaccagggc cggagttaga gaggcctctg cagccagcag cgacacctct tctgccaagg 6960
ccgccggggg catgctggag cttccagccc ccagcaacag ggaccatagg aaggctcagc 7020
ctgccgggga gggccgaacc cacatgacaa agagtgactc cctgccctcc ttccgggtct 7080
ccaccctgcc tctggagtca caccaccccg acccaaacac catgggcggg gccagccacc 7140
gggacagggc tctctcggtg actgccaccg taggggaaac caaagggaag gaccctgccc 7200
cagcccagcc tcccccagct aggaaacaga acgtgggcag agacgtgacc aagccatccc 7260
cagccccaaa cactgaccgc cccatctctc tttctaatga gaaggacttt gtggtacggc 7320
agaggcgggg gaaagagagt ttgcgtagca gccctcacaa aaaggccttg taacggggag 7380
ggcccagggg caggactgtg gagacccgtc ctgaacgggc gactgtgtct tgactacctt 7440
tcaaaaccag cactgtgtgg gaatgtccgc caggcagagc tcggagcctc attgagacag 7500
gggagagaga aagacaaaga ggggaccttc ttccagatgc cttcccagtt gtaaccggta 7560
aaactgttac cagatagtgt ttgtac 7586

<210> SEQ ID NO 16
<211> LENGTH: 1137
<212> TYPE: DNA
<213> ORGANISM: Homo sapiens

<400> SEQUENCE: 16
caaggagaag ccgcagtacc cgcggctcgg gtgcagcgcg ggagcacagt ggagcgcaga 60
tcgcggaccc gagcgggcat gtccccgcgc gcgggagcct ccgtttgcgg ccgggcccgg 120
gcggctgtga acttagcagc gggctcctgc ggccccgtca ctgccatgta gtcgctggcg 180
gggctccctg cagcccggga gcggcagtgc cagtgagcct gagcccagga gcccgcgtct 240

```
tccccgggag gcgctgagtg cgcgccgcgc ccccgccgct cgggaggcac tttgggccag    300

acagggaaat gggggagaaa gtttcggagg cgccagagcc ggtgccccgc ggctgcagtg    360

gccacggcag ccggactcca gcctctgcgc tggtcgccgc gtcctctccg ggtgcttcct    420

cggccgagtc ctcctcgggc tcagaaactc tgtcggagga aggggagccc ggcggcttct    480

ccagagagca tcagccgccg ccgccgccgc cgttgggagg caccctgggc gcccgggcgc    540

ccgccgcgtg ggctccggca agcgtgctgc tggagcgcgg agtccttgcg ctgccgccgc    600

cgcttcccgg aggagctgtg ccgcccgcgc cccggggcag cagcgcgtcc caggaggagc    660

aggacgagga gcttgaccac atattatccc ctccacccat gccgtttcgg aaatgcagca    720

acccagatgt ggcttctggc cctggaaaat cactgaagta taaaagacag ctgagtgagg    780

atggaagaca gctaaggcga gggagcctgg gaggagccct gactgggagg taccttcttc    840

caaacccggt ggcgggacag gcctggccgg cctctgcaga gacgtccaac ctcgtgcgca    900

tgcgcagcca ggccctgggc cagtcggcgc cctcgctcac cgccagcctg aaggagctga    960

gtctccccag aagaggaagt ttgatagatt cccagaagtg gaattgcttg gtcaaacgcc   1020

ctgtgtgtcc aaatgctggg agaacatcac cccttggatg aattgccacc acattaaata   1080

aaacatatcc aaagctcaaa aaaaaaaaaa aaaaaaaaaa aaaaaaaaaa aaaaaaa      1137
```

<210> SEQ ID NO 17
<211> LENGTH: 2618
<212> TYPE: DNA
<213> ORGANISM: Homo sapiens

<400> SEQUENCE: 17

```
ggctcggtcc gactattgcc cgcggtgggg gagggggatg gatcacgcca cgcgccaaag     60

gcgatcgcga ctctccttct gcaggtagcc tggaaggctc tctctctttc tctacgccac    120

ccttttcgtg gcactgaaaa gccccgtcct ctcctcccag tcccgcctcc tccgagcgtt    180

cccccactg cctggaatgg tgcggtccca ggtcgcgggt cacgcggcgg agggggcgtg     240

gcctgccccc ggcccagccg gctcttcttt gcctctgctg gagtccgggg agtggcgttg    300

gctgctagag cgatgccggg ccggagttgc gtcgccttag tcctcctggc tgccgccgtc    360

agctgtgccg tcgcgcagca cgcgccgccg tggacagagg actgcagaaa atcaacctat    420

cctccttcag gaccaacgta cagaggtgca gttccatggt acaccataaa tcttgactta    480

ccaccctaca aaagatggca tgaattgatg cttgacaagg caccagtgct aaaggttata    540

gtgaattctc tgaagaatat gataaataca ttcgtgccaa gtggaaaaat tatgcaggtg    600

gtggatgaaa aattgcctgg cctacttggc aactttcctg gcccttttga agaggaaatg    660

aagggtattg ccgctgttac tgatatacct ttaggagaga ttatttcatt caatattttt    720

tatgaattat ttaccatttg tacttcaata gtagcagaag acaaaaaagg tcatctaata    780

catgggagaa acatggattt tggagtattt cttgggtgga acataaataa tgatacctgg    840

gtcataactg agcaactaaa acctttaaca gtgaatttgg atttccaaag aaacaacaaa    900

actgtcttca aggcttcaag ctttgctggc tatgtgggca tgttaacagg attcaaacca    960

ggactgttca gtcttacact gaatgaacgt ttcagtataa atggtggtta tctgggtatt   1020

ctagaatgga ttctgggaaa gaaagatgtc atgtggatag ggttcctcac tagaacagtt   1080

ctggaaaata gcacaagtta tgaagaagcc aagaatttat tgaccaagac caagatattg   1140

gccccagcct actttatcct gggaggcaac cagtctgggg aaggttgtgt gattacacga   1200
```

```
gacagaaagg aatcattgga tgtatatgaa ctcgatgcta agcagggtag atggtatgtg   1260
gtacaaacaa attatgaccg ttggaaacat cccttcttcc ttgatgatcg cagaacgcct   1320
gcaaagatgt gtctgaaccg caccagccaa gagaatatct catttgaaac catgtatgat   1380
gtcctgtcaa caaaacctgt cctcaacaag ctgaccgtat acacaacctt gatagatgtt   1440
accaaaggtc aattcgaaac ttacctgcgg gactgccctg acccttgtat aggttggtga   1500
gcacacgtct ggcctacaga atgcggcctc tgagacatga agacaccatc tccatgtgac   1560
cgaacactgc agctgtctga ccttccaaag actaagactc gcggcaggtt ctctttgagt   1620
caatagcttg tcttcgtcca tctgttgaca aatgacagat cttttttttt tccccctatc   1680
agttgatttt tcttatttac agataacttc tttaggggaa gtaaaacagt catctagaat   1740
tcactgagtt ttgtttcact ttgacatttg gggatctggt gggcagtcga accatggtga   1800
actccacctc cgtggaataa atggagattc agcgtgggtg ttgaatccag cacgtctgtg   1860
tgagtaacgg gacagtaaac actccacatt cttcagtttt tcacttctac ctacatattt   1920
gtatgttttt ctgtataaca gccttttcct tctggttcta actgctgtta aaattaatat   1980
atcattatct ttgctgttat tgacagcgat ataattttat tacatatgat tagagggatg   2040
agacagacat tcacctgtat atttctttta atgggcacaa aatgggccct tgcctctaaa   2100
tagcactttt tggggttcaa gaagtaatca gtatgcaaag caatctttta tacaataatt   2160
gaagtgttcc ctttttcata attactctac ttcccagtaa ccctaaggaa gttgctaact   2220
taaaaaactg catcccacgt tctgttaatt tagtaaataa acaagtcaaa gacttgtgga   2280
aaataggaag tgaacccata ttttaaattc tcataagtag cattcatgta ataaacaggt   2340
ttttagtttg ttcttcagat tgatagggag ttttaaagaa attttagtag ttactaaaat   2400
tatgttactg tatttttcag aaatcaaact gcttatgaaa agtactaata gaacttgtta   2460
acctttctaa ccttcacgat taactgtgaa atgtacgtca tttgtgcaag accgtttgtc   2520
cacttcattt tgtataatca cagttgtgtt cctgacactc aataaacagt cactggaaag   2580
agtgccagtc agcagtcatg cacgctgatt gggtgtgt                           2618
```

<210> SEQ ID NO 18
<211> LENGTH: 4608
<212> TYPE: DNA
<213> ORGANISM: Homo sapiens

<400> SEQUENCE: 18

```
gcaggcggac ggggcgcggc gggggacacg gcggccgccg cggggctcga tcgggcaacg     60
gcggcgacgg cggcagcgac ggatcctcct cctcccttat tcccttgctc ctctttcttc    120
cttttctttt cctttccggc cggcctcgt ccactttccc taacggcggc ctcgatccta    180
cgtaaaggca tgacttcctg gcaccacagg gaaaatcggg tgcaagccca gaaactattt    240
ccccaccacc acttgttgaa aaactgattt gaaggcatct ccggggttga acaaacggaa    300
agtgccagga tttgatgcgt ctctggtttc gctctggaga ccattccctg ctaagtatca    360
agacgaaaaa aactggaaac taatccgaat ttctgtggaa tgtttaatct tctggatcca    420
tgactgtctg atacgttggc aatttaaagt ccttttgaaa gagagttcat gttacccagc    480
tattctctaa accatattta tttagagtca gaatggagcg atttgtagta acagcaccac    540
ctgctcgaaa ccgttctaag actgctttgt atgtgactcc cctggatcga gtcactgagt    600
ttggaggtga gctgcatgaa gatggaggaa aactcttctg cacttcttgc aatgtggttc    660
tgaatcatgt tcgcaagtct gccattagtg accacctcaa gtcaaagact cataccaaga    720
```

```
ggaaggcaga atttgaagag cagaatgtga gaaagaagca gaggccccta actgcatctc    780
ttcagtgcaa cagtactgcg caaacagaga aagtcagtgt tatccaggac tttgtgaaaa    840
tgtgcctgga agccaacatc ccacttgaga aggctgatca cccagcagtc cgtgctttcc    900
tatctcgcca tgtgaagaat ggaggctcca tacctaagtc agaccagcta cggagggcat    960
atcttcctga tggatatgag aatgagaatc aactcctcaa ctcacaagat tgttgactag   1020
gaggttacca ccattgtgat caagataaat gtggagtatt aaagttatgt gttgattgtg   1080
tggttcattt ttgtatttat ttcatttaaa atcatgtgac gcagaatagt tttgcaatgt   1140
gtatatagtt gcaggcaaaa aaaaaaccac ctcactgcaa aacttattgt taattttagt   1200
caccaatggt ataaagcaaa acctaggttt agagtgtgct aggatacctg aaacctgatg   1260
gttatcttta aaattaatgg tttttctcct gaaatgtttg tgcatggaag aactgccctg   1320
ctttttttacc ctgttgccat gtatgattat tccttgtgag attacttaat tacttggatt   1380
gaagactagc ctattgaagc tgctgccagg caacaccact taacagtaac ttaaaggaat   1440
tattttcttt agaggatcct cttcaaaaag gaagggagat agtggaaaac tgttcttata   1500
tcttcagatc cctagcagaa atgactgttt atttcaaact atgttttact tgtatatgat   1560
gtagtcacct taactatctt tcaattccat acttcccccg cccccatttt aaaggcttat   1620
tgttgtattt tgtagcagct tcaagtgacc aaaagactaa aatctttcaa cgtcaatgcc   1680
aaaagccaag gggaattttg cagtgacagg attttagtct cttactatga atactaattt   1740
cgaaccatag ctttcatttt aagcatcatc ttgaatttct aaactttttt ctatgtcttg   1800
gtgttaaaag atttcaagat tggcattttt acttaaacag acattttatg gttgagtttt   1860
ctctttatta tagagaatta gtaatttttt tttggctgac agatcagata aaattacttt   1920
ctattcatta atttttctct acaactttat gagtttattt aggtgaatag tctagactag   1980
aaacaagttt actttatctg ctttgcctct ggtggtacaa ggtttttaac atggatggta   2040
aacaattgtc tagaaattct ggcaggtttt ttgtattgga gatctggcag tatcctgcat   2100
aactttgggt gaggaaattg ttctcttaaa gatcagccat gttcaggaaa tgatctctgt   2160
ttgaacctca ctatcctgta aggttatcca agtagcttag cccagctaag ttctatcaga   2220
gacccaaatt atatttttta aaaatttaac agctggaaac ttggactaga gctttaataa   2280
aaaatcttaa attctttgaa attcaagtta aaaatactta tatatttcta ttacaaagca   2340
gtgacaaatg atgccctgtg tgacttggag ttatctttga cttttaccac aaatcttcat   2400
ttataaaaga aaaagccaaa gtgaaaaaaa gttagattgt gtatttttca gtaacagctt   2460
tccatgtctt aagatttttt tacagactta agtttctaat tcaggttgtc aaactggcca   2520
tttgacttca gagatttgtt ttcattaaaa aataagcctg ccgccaaaat aaatcactta   2580
tcaaaatgtg aactgttttc ctcatgttca gttatgttaa agtagtatga taaatgcatg   2640
cctagagtag tgctctcgtt gatgaagcac atgtatgagg agaccagcag caaaacataa   2700
ccatatgtgt tttgcgttta cttcctctag aaaagaattt gcaggcaacc atgtttaatt   2760
tgaactatct aagatggtag attttagaag ctaggaataa ttgagtttta tagcactatt   2820
ttcagaatac gaaaagatac acaatcattc tgttttttga aattccatgt gattcaaact   2880
gctccctatt atttgggtat taatttgcac taatagcaaa atgtaatggc agatcagctt   2940
tgagagtggt cctaagcagt aaactggatg atgttgcatt agaaaaacat caataattca   3000
tatttaagtt ttagtagtta ctactgattt gataatcact taaattttat atatcttaat   3060
```

gtatttttttc agactcctaa ttaattccca cattcactgt aactaggggc atagtccatt 3120
ctgttaggat tatatcctct ccttagaaat gttttccatc ctgttgtggg gatttggtat 3180
taatgtttct tcattgatta tggaactttt gttccctgaa gctagttaac tgtgtctaaa 3240
gttaaataaa tacagcagaa tgattgtttt agcctgctcg aactgataca aatccctgaa 3300
accatgattg gcatatgtta gataacaaat gaggatgtct aagaggcata tgctgctttg 3360
gaggtgtagt gaacgtgtgt acagaagttt tcaatcttaa ctatatagtg ttagtgtgat 3420
gctatactat tggaaaaata gcagcttttt tctattttat aagttgtatg cataaacata 3480
agatttgtaa tgtttcattt ataaactgcc ttcttcaaca catgttaata gtgttttctc 3540
aaagtattga tagtatgtct tccagaattt cacaatatgc ttacagtaaa tatttcctag 3600
cttgttgaaa tgttcaattc tttgttggct ttcttcttga ttctgtgggg gtgtataaca 3660
agcctgaagg acattgtaat catttcttac aaggtgaaaa ttaagaaaga ttgtgtatga 3720
gagcctatat agttgtttta tccattatca tctttgatta agactttaaa aaaatgctat 3780
ttccagttaa tgcatttggc cctattgaat tttcagggac cagaaaacat taaaaagttc 3840
tgcatcttat aatggtaacc aattaagctt gagattgttc tgaaagtatc aattgcttta 3900
aaactgttgt aagtacagtt ggcaagatct ccaagctgaa acttccacgt taaaactttt 3960
gcctgtaaga atttgcacat gaatgttaat ggaaaacaca aaacttaaga tggcccaaaa 4020
caaaagccac aaacagttca tcatttggtg cttagtcttt gtaagggctc tctgtggttt 4080
gacttacccc agctaccgtt aaatgaggac aaatcacctt aaaacatgtt catttgattc 4140
ataacaagga aaattgggtc tatgattttt tgccaatctt agcctaaaag aaattgcttt 4200
agcttctggt cagcactgat taaaatgtga atagtgaagt ggctatccta aactggttta 4260
tctccaccca cactatcata gatttcttag gtaaatacaa ttcttatcta gtggtattct 4320
acttgtattc agaatactgt attaaaattt tactatttca tttttgtatt ctgtgcttat 4380 ttttttgct cacgcatgta tgcttagtat aaatgtgtca cttctaaagt tttgtctctg 4440
acttttagaa ataaatttca gaaaaattgt ttcaaaagat tttgaaagca cattttgttt 4500
tgtgagtcaa tgacaaatat atttcctgat tacaaaacaa aaaaaaaaaa aaaaaaaaaa 4560
aaaaaaaaaa aaaaaaaaaa aaaaaaaaaa aaaaaaaaaa aaaaaaaa 4608

<210> SEQ ID NO 19
<211> LENGTH: 3008
<212> TYPE: DNA
<213> ORGANISM: Homo sapiens

<400> SEQUENCE: 19
gtgtgccctc cgcggggcat gatggggtag ctggagattt ccatcatggc ggcgtccatt 60
tcgggctaca ccttcagtgc tgtgtgtttc cacagcgcca acagcaacgc ggaccacgaa 120
ggatttttac tgggagaggt aagacaagag gaaacgttta gcatcagtga ctcacaaatc 180
agcaacacag aatttctgca agtaattgaa atccataacc atcagccttg ttcaaaactt 240
tttagttttt atgactacgc aagcaaagtg aatgaggaga gtttggacag gattcttaaa 300
gatcggagaa agaaagtcat tgggtggtac agattccggc gcaatacgca gcagcagatg 360
tcctacagag agcaggttct tcacaagcag ctcacccgca tcctcggcgt gcccgacctc 420
gtctttcttc tcttcagctt catctccact gccaacaatt ccactcacgc tttagaatat 480
gtgctcttca gaccaaatag aaggtataat cagaggatat cactcgctat tcccaatcta 540
ggaaatacta gccagcaaga gtacaaagtg tcttcagtgc caaatacttc tcagagttat 600

-continued

```
gccaaagtga ttaaagaaca tggtactgac ttttttgaca aggatggagt gatgaaagac    660
atcagggcga tttatcaggt ttataatgca cttcaggaga aagttcaggc agtgtgtgca    720
gatgttgaaa agagtgagcg agttgttgaa tcttgtcagg cagaagtgaa caaattaaga    780
agacaaatca ctcagaggaa aaatgaaaag gaacaagaaa gaagattgca gcaggcagtg    840
ttaagcagac agatgccgtc tgaaagcttg gacccagcgt tcagtcctcg gatgccgtcc    900
tctgggtttg cagctgaagg cagaagtaca cttggagatg cagaggcctc ggatcctcct    960
ccccccttact ctgattttca cccaaacaat caagaaagta ctttgagcca ctctcgcatg   1020
gaaaggagtg tctttatgcc tcgacctcaa gctgtgggct cttccaatta tgcttccacc   1080
agtgccggac tgaagtatcc tggaagtggg gctgaccttc ctcctcccca aagagcagct   1140
ggagacagtg gtgaggattc agacgacagt gattatgaaa atttgattga ccctacagag   1200
ccttctaata gtgaatactc acattcaaag gattctcgac ccatggcaca tcccgacgag   1260
gaccccagga acactcagac ctcccagatt taactaaaca aaagaaactc tccacctagc   1320
actgtttttc ttcattgctt actgagaggg tttttgagaa cttaatctgg ggggagaact   1380
gctttctcag ataccttaac tcccgagaag agagtccttg tgcacagaac ttgtgggagc   1440
ctccatccgc tgctctttac ctttggatac agtgtgcaag tttcatgaca gaatcattaa   1500
gataatcaaa ttgtcctaat tctggtgcga ttcatggata tactggtaaa tttaggcaaa   1560
gtgaaactta tcagcgtagt ttctgttctt taaaataaat tggaaattag agactaagca   1620
caattagtct ataaatgttc tataaatcaa aaacttacct cttgcactat catgccttga   1680
aatttacttt ttcaaaggga aacaagttta gcagcagcct tcaaagaact tctttctatg   1740
atgagccaaa ttcatctttg ccagaaaaga aattttgata attccaagaa gcctgattag   1800
aacaaatcag atataccttc tcttgtctgc atgactttgt gagataaaag agagggcttc   1860
caactttttt ctactagctt gatatgtatt atcacttaaa atggttgcct ttaaaaaaaa   1920
aaagtagaga tactaattac cagtaagtaa tcatccaaat aaatacgtca taaaataaat   1980
taattatttt ttctttgatg gattacagtg actactgtgt tgcactggca catttatggt   2040
ctctgttctg gaatcttgga ggacacacag cagtggagaa cagaaggagt gagttttata   2100
atgaacagat tccagacacg gtaggtttag ctgagttcat acagaggaga tataactcat   2160
ttagatcttc tgacaaatcc tagtgttagt tttatctgtg gaggaaagac atttaataat   2220
aaactgtttg ggaatcttgg tgaataaaga ttcattttca agctgaataa ccatacttat   2280
tttattttaa gttgccattt ggggaataat tgcagtatgt gtagagactc tcttgggatg   2340
cacttatatt tttatttaat gactacttgt tttctagttt tgcccacaac gtctgaaacc   2400
actaagacat tcaggagcat gttgagcttc tggtttggaa acagcaagac ccaccattta   2460
tgacaaggac agccatgagg ttaatacttg gagtttaact gccttccctt tgaactagtt   2520
aaaatctgta agaataagga agttgttgaa ggcttaaaat ctgggttctg aaaaagtagt   2580
ttcagtttat aggatacaca tttactcact gagctccagt tccaatacta aattagacag   2640
tatcatatag acggaaaatg aaatgctaga actgccgttc tttggatcgc cactctatgg   2700
gggtctgtct tttaactact ctcctggtta tgttggcctt acaccactgc catttgattt   2760
aaaacgctgc agacacttta tctgcaaatg tgttccagtt gttatcagct acctactacg   2820
cagcttcagc gccagtgtga atttattttt ttttaagtgc cattaccgtc tcctctgttc   2880
agattttgac attcaggaaa atatttttat tttgatgcca tactgaaatc tacaatgtat   2940
```

-continued

```
atctgacaaa gcagttaaat gtgacaataa aaaacttatt taatcatggt aaaaaaaaaa   3000

aaaaaaaa                                                            3008


<210> SEQ ID NO 20
<211> LENGTH: 2289
<212> TYPE: DNA
<213> ORGANISM: Homo sapiens

<400> SEQUENCE: 20

cgcgcccctc cctcctcgcg gacctggcgg tgccggcgcc cggagtggcc ctttaaaagg     60

cagcttattg tccggagggg gcgggcgggg ggcgccgacc gcggcctgag gcccggcccc    120

tcccctctcc ctccctctgt ccccgcgtcg ctcgctggct agctcgctgg ctcgctcgcc    180

cgtccggcgc acgctccgcc tccgtcagtt ggctccgctg tcgggtgcgc ggcgtggagc    240

ggcagccggt ctggacgcgc ggccggggct gggggctggg agcgcggcgc gcaagatctc    300

cccgcgcgag agcggcccct gccaccgggc gaggcctgcg ccgcgatggc agagatgggc    360

agtaaagggg tgacggcggg aaagatcgcc agcaacgtgc agaagaagct cacccgcgcg    420

caggagaagg ttctccagaa gctggggaag gcagatgaga ccaaggatga gcagtttgag    480

cagtgcgtcc agaatttcaa caagcagctg acggagggca cccggctgca gaaggatctc    540

cggacctacc tggcctccgt caaagccatg cacgaggctt ccaagaagct gaatgagtgt    600

ctgcaggagg tgtatgagcc cgattggccc ggcagggatg aggcaaacaa gatcgcagag    660

aacaacgacc tgctgtggat ggattaccac cagaagctgg tggaccaggc gctgctgacc    720

atggacacgt acctgggcca gttccccgac atcaagtcac gcattgccaa gcgggggcgc    780

aagctggtgg actacgacag tgcccggcac cactacgagt cccttcaaac tgccaaaaag    840

aaggatgaag ccaaaattgc caaggccgag gaggagctca tcaaagccca gaaggtgttt    900

gaggagatga atgtggatct gcaggaggag ctgccgtccc tgtggaacag ccgcgtaggt    960

ttctacgtca acacgttcca gagcatcgcg ggcctggagg aaaacttcca caaggagatg   1020

agcaagctca accagaacct caatgatgtg ctggtcggcc tggagaagca acacgggagc   1080

aacaccttca cggtcaaggc ccagcccagt gacaacgcgc ctgcaaaagg gaacaagagc   1140

ccttcgcctc cagatggctc ccctgccgcc acccccgaga tcagagtcaa ccacgagcca   1200

gagccggccg gcggggccac gcccggggcc accctcccca agtccccatc tcagctccgg   1260

aaaggcccac cagtccctcc gcctcccaaa cacaccccgt ccaaggaagt caagcaggag   1320

cagatcctca gcctgtttga ggacacgttt gtccctgaga tcagcgtgac caccccctcc   1380

cagccagcag aggcctcgga ggtggcgggt gggacccaac ctgcggctgg agcccaggag   1440

ccaggggaga cggcggcaag tgaagcagcc tccagctctc ttcctgctgt cgtggtggag   1500

accttcccag caactgtgaa tggcaccgtg gagggcggca gtggggccgg gcgcttggac   1560

ctgcccccag gtttcatgtt caaggtacag gcccagcacg actacacggc cactgacaca   1620

gacgagctgc agctcaaggc tggtgatgtg gtgctggtga tccccttcca gaaccctgaa   1680

gagcaggatg aaggctggct catgggcgtg aaggagagcg actggaacca gcacaaggag   1740

ctggagaagt gccgtggcgt cttccccgag aacttcactg agagggtccc atgacggcgg   1800

ggcccaggca gcctccgggc gtgtgaagaa cacctcctcc cgaaaaatgt gtggttcttt   1860

tttttgtttt gttttcgttt ttcatctttt gaagagcaaa gggaaatcaa gaggagaccc   1920

ccaggcagag gggcgttctc ccaaagatta ggtcgttttc caaagagccg cgtcccggca   1980

agtccggcgg aattcaccag tgttcctgaa gctgctgtgt cctctagttg agtttctggc   2040
```

-continued

```
gcccctgcct gtgcccgcat gtgtgcctgg ccgcagggcg gggctggggg ctgccgagcc   2100

accatgcttg cctgaagctt cggccgcgcc acccgggcaa gggtcctctt ttcctggcag   2160

ctgctgtggg tggggcccag acaccagcct agcctggctc tgccccgcag acggtctgtg   2220

tgctgtttga aaataaatct tagtgttcaa aacaaaatga aacaaaaaaa aaatgataaa   2280

aactctcag                                                           2289
```

<210> SEQ ID NO 21
<211> LENGTH: 10923
<212> TYPE: DNA
<213> ORGANISM: Homo sapiens

<400> SEQUENCE: 21

```
attcatttcc tgagaactgc agagagccgc tgagaggctc tgcgtgtgcg tgtgcgcggg     60

tgacgccgtg tgtgtgcgag tgtgtgtgtg tgtgtgcgcg cgcgcgtgtg agagagagaa    120

agggagagag agagggggac tctgtgtgag ggaaagaaaa caatttctcc tgctctgcag    180

cttctgttca ggatcaatgt gactctaaga acaaatggat gaatgaatat ccatatgaag    240

agaaaaacaa taaagaatat caacaccttt gagaacagaa tgttaatgct tgatgggatg    300

ccggcagtca gagtcaaaac agagcttttg gaatctgaac aagggtctcc aaacgtccac    360

aactatcccg atatggaagc cgttcccctg ttgctaaata atgtgaaagg ggagcccccg    420

gaggactcgt tatctgtaga tcacttccaa acacaaactg agccagtgga cttgtcaata    480

aacaaagcca ggacgtcccc tactgccgtt tcatcctccc cagtttccat gacagcatct    540

gcctcctcac cttcttcaac ttcaacctct tcatcgtctt ctagtcgtct agcctcatcc    600

ccaactgtta tcacatcagt atcttcagcg tcatcttcgt caacagtatt aactccaggg    660

ccccttgtgg cctctgcatc tggtgttgga ggccagcagt tttgcacat tatccatccc    720

gtaccgcctt caagtcccat gaatttacag tctaacaaac tgagtcatgt tcaccgcatc    780

cccgtggtgg tacagtcggt gcctgttgtc tacacagctg taaggtcacc tggaaatgtg    840

aacaacacta ttgtcgtgcc gcttttggag gatgggagag gccatggcaa agcacaaatg    900

gacccccgag gcctatctcc cagacaaagt aaaagtgaca gtgatgatga tgacctgcca    960

aatgtgacct tagatagcgt taatgaaact ggatctacgg ccctttccat agccagagca   1020

gtacaagagg tacatccgtc cccagtatca agggtccggg gcaatcgaat gaataatcaa   1080

aagtttcctt gttcaatttc accatttagt attgagagca caagacgcca gagacggtct   1140

gaatccccag actccagaaa acggcgtatc cacagatgtg attttgaggg atgcaacaaa   1200

gtgtacacaa aaagttctca cctgaaggct caccggagga cacatacagg agagaaacct   1260

tacaagtgta cctgggaagg ctgcacctgg aagttcgctc gttcagatga actgacgagg   1320

cattaccgca aacatacggg agtgaagcca ttcaagtgcg cggactgtga tcgcagcttt   1380

tcccggtcag atcatttggc cctgcaccgc cggaggcata tgttggtgtg aggaatgcta   1440

cctgtccagc tgagcgtaag agctggatct cttagcggca cccaattcag cagggctgaa   1500

tccccttcac agtgttaaca caaaagggca tcaccatccc acgatgtctg aaaccagagc   1560

aggaaaaaga aggcacactt cttttggtct gaaggtaacc cccatcatga ctagacgaga   1620

accgtcttta cccgggcctg ggagctcagt gacataaatg ctgaagagac aggcattgtt   1680

ttccgtgctg tgtcctctgc catttaaaga tgtttgtagc ttgtacattt tctgagctgt   1740

cagacatttt gttattgata ccttaaaggt cacctaccac aaattgatgg ctagagcaag   1800
```

-continued

```
accttttaaa tttggatgaa tctcccatca tcccatccct taacccottt ttacagaaat   1860
tttagttaca atctgagtaa gctagaacac acatccaatc tgttaccagc aagcagcatg   1920
aaagtagaaa cgaagaagca gatggagagg tcccattacc tgcaaagaaa gggcactcag   1980
gcagcccttt gcaatcgcga tggcagccac tagatatcac tctcaacttg tcattctgcc   2040
atgccctgaa gaaaaccaac attgaatctt tcatttgttt gtcgttgatt gtttttgttt   2100
tgtttcgatt ctgttttgtt catctgttcg agcagagggg cagttgaagt ctcgtcctgg   2160
tctctgccct ggcatggact ggcacagagg tgttctgtag ttgaatagga agagcctgtc   2220
taaaaaacta ctgccccact tcaaattgca gtgttctgtc acctaggcat catctcttcc   2280
tgcccctagt atttgattac aaggaaccag gggaaaaaaa ctttcttaga cacactggca   2340
ccaaggtaag aggtggggct gcccaggcaa agtcagtgaa catgaaaact cagacaaagc   2400
agagatggaa ataatgcgcc tcttgaggag aaaagcaata atgaataaaa ggactttcct   2460
acaataactt cactgaggac tcacgttacc aattttcata cttactaaag ggattgtaaa   2520
aaacacccca gcattttagg tgtcttggtt ccatttacag cactgaggta atctttctgc   2580
tgtttgttgt cctgcttggt tgagtaccac aattaaagat tatgctcccc ttttcttgtt   2640
tgaaaacagt tatttggtga ctagaaaggc aagggaggca tagccgggaa ttaactcttc   2700
ggttaatggg tcagttctcc ttggaactga atcagtggaa agagaatgct tcccatagaa   2760
agcccgacat ggtgctagtt tcctctcttg gagagccaag gataagtgac tctccaatag   2820
gttcttctat accgatttca ttttctaaac tgtatcagga cccaggtgtc ctgcattggc   2880
atctgcaggg atattgaacc cactcatcct gtgcagagga tgagaggaag gtgttagttc   2940
catcagcccc ataaaattat gaaccttttt gcaactagga acatatacag taaacaagca   3000
atacatcacc aacgagcatt ctttcagaaa aattaccata tttttgtccc caccacaagc   3060
tgggtttttt tccagctttc tgtggctgag ggctggtga gatttttgt tgttattgtt   3120
gttgttgcta gaattttta tagcttagat ataaaaggtc tccaacaaag acctttgcaa   3180
tatattttaa ttacaaacac ttgattttgg gaattgcaca tattaacctc acaatattac   3240
tagctcattt ttaaatgtct ggacattctg aaataatttc cggttacaga attacccttt   3300
ttaggatcat cttctaattc agataatctt attctgatga agcgagaact atgaacgttg   3360
aaacaaggac aatttgtgtt ggatggtatt caaaaggaat tttttaaaac attaagcaac   3420
agtgtaatga ttttcaggtc aaattatggc ttcacaaata tgtgctctat attgtctgcc   3480
aggtctcaaa aattcatcaa gcaatttccc tccaacaagg gctgcagttc tagtgataaa   3540
tagcatcttt agctgcacag tctactactc atcaaccagt gggtttttt tagcacctgg   3600
aaagtttttt tgtactatat gcaactccta cttcacattg cctgtgacca ttcagaatag   3660
aaaaaggtct gttgatgcat gccagtgctg gttactagtc agtgacagag aacacagaga   3720
gggacaaaca cagccatgaa ccccctggca ctagtaccag cacctagttg gcaagtagtg   3780
ggtgcatctc tcaagtgaag tgtagatttg tatttagtcc tgcttgctct cataaaaaga   3840
gccagttctt ttctctgctg aaagatgtct tgagagtatt acaggtagac ttggttttta   3900
gaattcataa aactgacagg caggggaatc ttcctgagtg acagcttggt ttaaatttag   3960
cacagaacta gatgagttgc acttttctaa taacatagga tggatttggg gaagggaaca   4020
ttttccctca tcctctgaaa gtggaaacca gactgagatg gtaagttaac tgataaaacc   4080
tgtcagcatt ccatcatttt ccccttttga cgtatcagta cttctaagaa gggatctaag   4140
cacaattaag tgaattgagt ccctggtcta gcctcaggaa ctgaaacttc tttggggctt   4200
```

```
gtcttgagac gtggcaaatt ctccttggtg agttttctaa aagtatttcc ccatggaaag   4260
gagaaagtgg tttgggacag aaagaaatgg aatgtcttca gtcatggaag agcctccatt   4320
tcatctcatg tccatttcta gcctctttca aaaagcacag tgcatcatga gcaacagaaa   4380
agcagtagaa tcctaaagga cataacagtt gttccgtaac tagaagcatt ctttgatttt   4440
aaatttgaag ctgttcagtt tgcagctggg gatatgtgca tggttgggaa cttatacaca   4500
tagagccatt aactacttaa gcagctgcag tagacctgat tttctgtttg cagtatagag   4560
attgatttca agggagttac attatttgaa aagttatgac tttcagcctt tgaggtttta   4620
agaatccctt ttcatggtct gatcttaagt tgtttgaaaa aagattcacg cttctgcatc   4680
cacctctgcc ctcattctgt caattgtgtg tggactctga gaagcctgct tgataacttg   4740
tcttaagttc tattaaggca gttagactga gatttctaat gacttcacca taaagattat   4800
acttctgcct ggcgtcgttt ctataaaaca ctataggaca tttgttttca aaagcagttg   4860
agtaacagca acataaacca catttttttaa aaaaatgagc acttttcatt cacttgaaag   4920
cttaagtggg aaaaaggaag atgattgtca ggggaaaaac ttacaaaatg ctacagtgtt   4980
tacaaatgcc agttccaggt gattagaaag gccgttttca ttatggttca gatttggaat   5040
agcttatgca aagattgtgt tcatttttat acaattcttt ttaactttaa attgccatct   5100
gtgttttaaa cataattctg cactttggaa tcagttcatt agaatgataa catttatatg   5160
gataaagatg cagtattcct tattctgtac ttgatttatt atacttacca aagctgcaac   5220
tgaataaatc tggtgaggtg aggccttcaa aatgtattaa tacgcctttg ttatgttgtt   5280
atgactgctt agaaatgtag ccatgatgtt gttctaaaga tgtcttaaca tttatagtga   5340
ggattgacag aaattaagca gtgttaagaa taccagcatc catgttacag tctgcgtata   5400
agggactgaa tgtgaggtaa ctcttatgaa tcataatagg cccagaaagc cttaatattc   5460
atagttcata atccagtctc agattttgct cttcaatgtt gcctgtaaac ttagcaggta   5520
aatgtattct agtataaaac atcattgacc aaatctcttc ctttagtttt tctgaggtag   5580
tgcatcccat taaaaaagtc tcttcaatta gatttggctt tagtttagaa aggggtttgg   5640
taagtcatgt cttccatatg acatttctac tcatccccac actgccttcc acttaacctg   5700
tacagacagc cccaacacat gcacatgtgt gtacacaact gtatatgcag cagccagtgg   5760
gctaacaaat atcagcaaag aacttttttta aaaagaattt gtaataatcc gtgctgtcta   5820
gaaatgtgag ttacttacct tattaggaaa ccggcttata atactatata tgactctgcc   5880
tgcattttat agttaagaaa tgtacataaa aattgctata ttttcacagt ttcattataa   5940
tgtctgttta gtaacccatg tccactgata ctttaaatat gctaattact gagcaattgc   6000
aatagaaatc cagattttca taagaaaatg aaatagaagg atactgcatc tttaaaaaat   6060
agagtgaaga tattttactg tattcgtaac atatgtgata gtggaaaaag tattttcaaa   6120
ctcacaaatt ttacagaggt tgtaaatagt ttgatgaagt atgttgggaa agagagcttc   6180
tagttttcat cacaataaaa agaaaaaact tgttcagata tgccttgtat atcttacaca   6240
caatgagtga aattgccatg ggaactctgt ccaactttgt cagagcatgc tcttcgtgtt   6300
ctgttcaaaa tagagtggcc acttgtcatg gtttagccag gatggtttaa aatataatga   6360
agtcatttta agttgcagac aactgattcc aaactagtaa tgtcttttcc tgaaaagggc   6420
aaaacagctg cacaggattt tgcttgtact aaagaggagc atcttacaat tgttctcttt   6480
tctcagttat ctccctcctc aacagagtgt gaacaaccat acaggtgttt attcttgttt   6540
```

-continued

```
tattccaggg agactgcttt taggtataac tacatgttga caagattaag tgctgtggat   6600
atggccacgt gttaaaggaa tctatactcg caataggaat aagctaatgc ccattttcag   6660
aaataaatta aatgctgaaa gtgcctgtca gtaaacctta tgaccaatga gatattccta   6720
tacttttaca cagcaataat tcttaataag actgggtttt ttcctgcaca tgtgaacaca   6780
cacacacata cacacagaga gagtaaatac atacacatag taaatcaaat ctgttcacat   6840
gcccacaaaa aacgctttta tagctttcaa atatacctaa tcttgtttac attaacattt   6900
cttaatttga tctttctaac ttgcagaacg ttaagaacac aaatctgaac attaagttta   6960
tcttcagtga acactattgc atatggtaat tataatttcc agataaaaag ttgactgtca   7020
tttgccccaa acttatgaaa cagtatgtat gattcaaaaa gttttgctca gttaaaaaca   7080
ccaatttatt tggcgcaaaa gactgaagga tatttgtttg cttgttcatt ttatccactc   7140
atatcaaacg cacaaattca tctttacatt tcttcattcc cctttcccct aatatttcct   7200
attatcatct taagaatcat tttggaatga atattgacag aatcatttct ccccaaaaag   7260
tctgttgaag taccactgac acttagtaag cctagccttt aaccatcttt gcagttagtc   7320
ctaaaaatta ccagatgcac attcagaagc tcacaggttt tttcctgtaa ttactgtact   7380
gctaaaagtg gagtcatgga tagaaatata caatgagact atatgaatag acatgaaccc   7440
tggaaattct ccaaccctgc catctcagag cacaaattca cccaaacaag ctactgaggc   7500
tatcagtaaa attatactca tggagagtca cacatcgggt aagggcaatt ttaaaagtag   7560
gactgtgatt aaacattcag gctttagact tccatgatgg actcagacca caggcctcaa   7620
aaaaacatcc actgttttct cctcccaatg ttagaaagaa gaaaagggag acggaaatgt   7680
accaggataa gggggtaaaa taaccaatta agtgtcaaag gaaagctgct gggttcctta   7740
atctcactga agtcaagtct tctgactggg cttcttacca tgtgttgtct gaaaaaacta   7800
aagtaccttg aaaggttaca cattcagcaa accatgaaga taatagctat tctttattaa   7860
acactgtgtg ccaagcaata gactaggcaa tttttagata cgttacctgc aacctgtaca   7920
acatttctac actttatgga tgggaaacgg agacatggga agtgtggctg agttgttcat   7980
ggatgtagaa atagtaaacg gcagagtagg aaagtgaaac cgcctatctc tgacctggag   8040
gtctgcctgt atctttccca ctccaccaca ctgcacgtgg gtgtcccgaa accaccttcc   8100
cagattcctg actctcagta attttattat ggacaacatg catgagtagt catcatattt   8160
ttcaagtgaa atatcgggac atgatataac acatgactta acaatggtac tgaatatttg   8220
aaatcaggcc tttcccggaa aatcatgcat gaaggatcat tataaacaaa caatagcaac   8280
cagttgtctc cccgaacttg tcacttttct cataaatgtc tggcctggag ctccaaaatc   8340
atccaaatac ttagtagcat tttagcctga gtacactttc tcagttcctc aactctttgt   8400
ataccttttcc accaatatag acattctaga atctgcttca gatgcatttg aaattttcac   8460
ccccatggaa ctagtgatta atatcagagc ccactcttgc agttggtaat ggggtggcaa   8520
tcaaacgttc agatgatgat aaaggagaga taatggataa ttctttttca gagttctcac   8580
ttaacagctc tgttgtggaa tgttttaaat agtcttataa ataatttgtt tatagtattg   8640
ttgttagttt aattgaattt tatgtaagaa gctgtccaac atcagagaaa tgaaattcct   8700
cccactttct gtgtagaaca aggtctctga cagtattgat tcatggaagt actaatggac   8760
ttagaaaaca ttaagagaat gtcatttctc atagtgtttc tgtttctgaa aatgaatctc   8820
ctgaattatt atctttctcc ctgttacttg gctggggaaa gagatagaag ctgtataaac   8880
aaattctctt ccatgctcaa agcaagtgtt ccatgtgcac aacctgctgc agactggggc   8940
```

```
ccttctcagt taattgggtt tcacaagcaa taatttctcc acaacaaaaa ccacaacttg   9000
aagtgagttg aaaagagatc aatagtggaa acagtcgcct cagtactttt tctttctgga   9060
tttcatctct agaaatttga agtgtttgag acagagtcca ccctttgtgc aaggcgagaa   9120
ccaatgaatg gactccttgt gtgaattatt gcatcttctt ccaaagcagg ttcatcaaga   9180
ctttcacaga gattcatttt tgttgagaag taagggttaa taggaggata gaatttggat   9240
ccaaatctag tgataaaagt gtccaagcaa tcaaaaagta agatatttta gggacatacc   9300
aacatcttcc ctttctgcta atttcatgct ccaaagatat ggcaaaaaaa aaaatcataa   9360
aaagtgcttt tgccctactt gtgttctagt tttcccatgg cagaattttg taattacatc   9420
cagaatatag tgtatatttt gttcctcaaa ctttattaca ttggatggat attgttgaac   9480
tggggcactg gtgcctatat tcaaggctct ttcctatcaa cgtgtctgtc cacgatttgt   9540
tgtgtttaaa gcttcatttt gaaaaatcac tgtccccctg tggggtagtg actgtattgt   9600
tttgttcatg tctatgtggg acacattgca tcacatggca aaccaactct ctgtggatgt   9660
gagataagta cttataaaac cagcttgaaa acatcgtctt atgtattatg tcatcctgca   9720
tcataatgca attatgtgta tcataacatg ctcatttaaa aaaagagaaa ccagcaaatt   9780
catgtttgtc catagaagaa tgtactcaga actttgtgtt gtgaaacgat gagaacagac   9840
cacctttaag atacccacct gccacttaaa atgacttagt tataattagt agtagtctag   9900
acgttgttct tggtgtgtgg gggtcaattc taacgtcatg ttcttttgaa taaatctctc   9960
agtcatattt gaaaaaaaaa tacatgggaa taaagaaaaa tatcatcttt ggccaaatca  10020
agcaggcatc tttttctttt tccttgacgt ttagctcatt atacgtggtg attggatcac  10080
gagatctgtc cgtgtgaaaa tacagaaaca tcctttagtt tacaaaacag ttattctagg  10140
cttgaagcct ctgaacagca aattgaatag atgggctgca tctgatttgc tttatggatg  10200
taattttaca aaacactctt gggtctctga ccccagggag ttaagagtgc ccagaggagg  10260
tcctacacat taaaggataa agccccccag tgatgctggc aagcaaatgt gttgagttct  10320
taaatcttca tttggttttc tgttcaggat tttaattgca aatgaattta tttctccagt  10380
ttatctaaag acctaatttc ccaatagttt cctctgcatt tatatactct gtagtgttta  10440
ggcaaccctg ttataagttt attaatatta tgtaagtgtt gttcttgtat ttatgtatag  10500
tgtatgtatt gtaaatatac tcagagcttt tttcctttta ctgtaaaatg gtgatttttt  10560
tgccctatga taatgtaaag ggagaccctc ctaatgagat tctctcagag gatgattatt  10620
ccagtctatt ctcagagatt taaatgaaca agtgttattg tttttaatgg tgtctcagac  10680
atattctgtt ggtgcattgc ttttctgtat tcaactttcc tatgaattga gctgtgaact  10740
gaaatagagt ttaaaccttt aactgtatgc atttgtataa ttatctgaat gaaggcatga  10800
aggttaaata aagcattttg tatggaacaa aactccctaa ctgactcaga cactttggaa  10860
atcatagtta ttaaccattc taattaaacc tttgttatga aaagttttaa aaaaaaaaaa  10920
aaa                                                                10923
```

<210> SEQ ID NO 22
<211> LENGTH: 3390
<212> TYPE: DNA
<213> ORGANISM: Homo sapiens

<400> SEQUENCE: 22

```
agaaggggaa acaggaatcg attaggaata aaggattata atccactttc cttctgagga     60
```

-continued

```
aaagctggga accttctcat tttgccttat gaaaactaag ctgaatcgac tgctgccaaa    120
catctattag gcaaaattgg cctcttgccc atgatttgac tttccagcac agccagttct    180
ttttctcctc tgcagctgat tggctctgga gtgtggccag aagcctctct cctgcaatta    240
aaggagtcgg gtctctaact gttgatctgt ttttttccct tctgagcaat ggagcttacc    300
atctttatcc tgagactggc catttacatc ctgacatttc ccttgtacct gctgaacttt    360
ctgggcttgt ggagctggat atgcaaaaaa tggttcccct acttcttggt gaggttcact    420
gtgatataca acgaacagat ggcaagcaag aagcgggagc tcttcagtaa cctgcaggag    480
tttgcgggcc cctccgggaa actctccctg ctggaagtgg gctgtggcac gggggccaac    540
ttcaagttct acccacctgg gtgcagggtg acctgtattg accccaaccc caactttgag    600
aagtttttga tcaagagcat tgcagagaac cgacacctgc agtttgagcg ctttgtggta    660
gctgccgggg agaacatgca ccaggtggct gatggctctg tggatgtggt ggtctgcacc    720
ctggtgctgt gctctgtgaa gaaccaggag cggattctcc gcgaggtgtg cagagtgctg    780
agaccgggag ggcctttcta tttcatggag catgtggcag ctgagtgttc gacttggaat    840
tacttctggc aacaagtcct ggatcctgcc tggcaccttc tgtttgatgg gtgcaacctg    900
accagagaga gctggaaggc cctggagcgg gccagcttct ctaagctgaa gctgcagcac    960
atccaggccc cactgtcctg ggagttggtg cgccctcata tctatggata tgctgtgaaa   1020
tagtgtgagc tggcagttaa gagctgaatg gctcaaagaa tttaaagctt cagttttaca   1080
tttaaaatgc taagtgggag aagagaaacc ttttttttgg ggggcggttt ttttggtttg   1140
ttgttggttt tttttttttt tttggcggga agaaagagtt ttgctcttgt tgcccaggct   1200
ggagtgcaat gacgtgatct ccgctcactg caacctccac ctcgcgggtt taagcgattc   1260
ttctgcctca gcctccctag tagctgggat tacaggtgcc caccaccatg cccagctaat   1320
ttgtattttt agttgagaca gggtttcact acgttggcca ggctggtctt gaactcctga   1380
tctcaggcaa tccacccacc tcagcctccc aaagtgctgg gatgacaggc gtgagcaacc   1440
gcacccagct taaggttttt ttgttttgtt ttgagacgga gttttcgctc ttgttgccca   1500
ggctggagtg caatgctgtg atctcagctt accacaacct ccacctcccg ggttcaagtg   1560
attcacctgc ctcagcctcc tgagtagctg gtattacagg catgcgtcac cacgccggct   1620
aattttgtac ttttagtaga gatggtgttt ccccacgttg gtcagtctgg tctcaaattc   1680
ctgacctcag gtgatctgcc tgcctcggcc tcccaaagtg ctgtgattac agacgtcagc   1740
caccatgcct ggcctgaaac ctttttttagg taaagttgaa ttccatcctt aaaagtttct   1800
gttatatcct atttagccat tttctattgt ctcccaaaga attcacatca aaaaaacagc   1860
tttgaactcc cccttcaaag gaaacagtcg actttcataa ttagcatcta ccattatccc   1920
caaatcttat tttattcatt gacttgaaat tttttccaat tgcttttttt tttttttttt   1980
taaggttaag agcagaggtt tactaggcca aagaaagaga atagctctct gttgcagaga   2040
ggggtcctgg agaaatgggt taccccagtt gtcttattta aatggttacc catcagattt   2100
taattttatc ttctctttga gagcttggta ataagaagca cttaaatcac tccaaagaag   2160
actttaaaaa gggagcagtg aaaaggtctt aataatttat tgattgaatt aagaaatact   2220
agctaattaa gaatctgagt ctaaacagca cagatttttt ctttctgctt ttaaattgtg   2280
ttttaaaaaa agagacaggg ggctgggcgt ggtggctcac gcctgtaatc ctagcacttt   2340
gggaggccga ggcgggtgga tcacgaggta ggagttaaag accagcctgg ccaacatggc   2400
aaaaccctac taaagataca aaaaaaaaaa aaaattagcc aggcgtggtg gtgggtgcct   2460
```

gtaatcccag gtacttggaa ggctgaggca ggagaatctc ttgaacccag aaggcgaagg 2520
ttgcagtgaa ccgagatcat gccattgtac tctagcctgg gtgacaagag caagactccg 2580
tctcaaaaaa aaaaaaaaaa aaaaaaagaa gtagagacag ggagacaggg tctcactgtg 2640
ttgcctaggc cggtcttgaa ctcctgggct caagtgattc tcccaccttg acctcctaaa 2700
ttgttgggat tacaggtgtg agacagtgca cctggccgaa atagctcaag tttctgaaaa 2760
acaaatctga atctatttgt tattcttagc gtcactggtc tggctttcag aattaacata 2820
caaggttgcc acacctagtt ctgcccagct ttatgtcttt tattccagta ttccaccaaa 2880
gtttgttttc ctgcattcca gttctcaagt cttaagataa agattgtact tgacagttta 2940
gtatatccat aaaactattt gaggtggtta aggttcttgg gttcattttc cttaatactt 3000
tgctgaatat tgtagattgt aggcaatgaa aaagtctact aaattaggaa aaccttgaat 3060
aattaggtat cctaggtaag agcccctaaa catcaagcaa tctgtgagtc tgtaaagaaa 3120
taaatatttt ttggattatt cttatctaat tccacccctg ttggaagatg atttctttgt 3180
tctttgcaac tatggaagct gtgaaaatca tcacaagtgc ctctgaaagc gagtgttagg 3240
ttggttagag ggtttaatat tttctgcaat ggtttgtagg aattttaata aatgtagtat 3300
attttctgag atgattttgt aaaagtacta ttttaaatat caaatcaacc aataaattca 3360
catttgtgtt aggaacagaa atatggttta 3390

<210> SEQ ID NO 23
<211> LENGTH: 2197
<212> TYPE: DNA
<213> ORGANISM: Homo sapiens

<400> SEQUENCE: 23
attcttcctc ttgccacacc cacagggccc gcactaagag cctaactgaa atcccgcgag 60
gatcaaccga gctcgccgaa aggagggagg aacgtatccc ttctggaggc tgtctcaggg 120
ggcagaggga ccggaccgga agtgacgtga gcgggttccg gttgtctgga gcccagcggc 180
gggtgtgaga gtccgtaagg agcagcttcc aggatcctga gatccggagc agccggggtc 240
ggagcggctc ctcaagagtt actgatctat gaaatggcag agaatggaaa aaattgtgac 300
cagagacgtg tagcaatgaa caaggaacat cataatggaa atttcacaga cccctcttca 360
gtgaatgaaa agaagaggag ggagcgggaa gaaaggcaga atattgtcct gtggagacag 420
ccgctcatta ccttgcagta tttttctctg gaaatccttg taatcttgaa ggaatggacc 480
tcaaaattat ggcatcgtca aagcattgtg gtgtcttttt tactgctgct tgctgtgctt 540
atagctacgt attatgttga aggagtgcat caacagtatg tgcaacgtat agagaaacag 600
tttcttttgt atgcctactg gataggctta ggaattttgt cttctgttgg gcttggaaca 660
gggctgcaca cctttctgct ttatctgggt ccacatatag cctcagttac attagctgct 720
tatgaatgca attcagttaa ttttcccgaa ccaccctatc ctgatcagat tatttgtcca 780
gatgaagagg gcactgaagg aaccatttct ttgtggagta tcatctcaaa agttaggatt 840
gaagcctgca tgtggggtat cggtacagca atcggagagc tgcctccata tttcatggcc 900
agagcagctc gcctctcagg tgctgaacca gatgatgaag agtatcagga atttgaagag 960
atgctggaac atgcagagtc tgcacaagac tttgcctccc gggccaaact ggcagttcaa 1020
aaactagtac agaaagttgg attttttgga attttggcct gtgcttcaat tccaaatcct 1080
ttatttgatc tggctggaat aacgtgtgga cactttctgg taccttttg gaccttcttt 1140

-continued

```
ggtgcaaccc taattggaaa agcaataata aaaatgcata tccagaaaat ttttgttata   1200

ataacattca gcaagcacat agtggagcaa atggtggctt tcattggtgc tgtccccggc   1260

ataggtccat ctctgcagaa gccatttcag gagtacctgg aggctcaacg gcagaagctt   1320

caccacaaaa gcgaaatggg cacaccacag ggagaaaact ggttgtcctg gatgtttgaa   1380

aagttggtcg ttgtcatggt gtgttacttc atcctatcta tcattaactc catggcacaa   1440

agttatgcca aacgaatcca gcagcggttg aactcagagg agaaaactaa ataagtagag   1500

aaagttttaa actgcagaaa ttggagtgga tgggttctgc cttaaattgg gaggactcca   1560

agccgggaag gaaaattccc ttttccaacc tgtatcaatt tttacaactt ttttcctgaa   1620

agcagtttag tccatacttt gcactgacat actttttcct tctgtgctaa ggtaaggtat   1680

ccaccctcga tgcaatccac cttgtgtttt cttagggtgg aatgtgatgt tcagcagcaa   1740

acttgcaaca gactggcctt ctgtttgtta ctttcaaaag gcccacatga tacaattaga   1800

gaattcccac cgcacaaaaa aagttcctaa gtatgttaaa tatgtcaagc tttttaggct   1860

tgtcacaaat gattgctttg ttttcctaag tcatcaaaat gtatataaat tatctagatt   1920

ggataacagt cttgcatgtt tatcatgtta caatttaata ttccatcctg cccaaccctt   1980

cctctcccat cctcaaaaaa gggccatttt atgatgcatt gcacaccctc tggggaaatt   2040

gatctttaaa ttttgagaca gtataaggaa aatctggttg gtgtcttaca agtgagctga   2100

caccattttt tattctgtgt atttagaatg aagtcttgaa aaaaacttta taaagacatc   2160

tttaatcatt ccaaaaaaaa aaaaaaaaaa aaaaaaa                            2197
```

<210> SEQ ID NO 24
<211> LENGTH: 3883
<212> TYPE: DNA
<213> ORGANISM: Homo sapiens

<400> SEQUENCE: 24

```
ttggttgcgc ggtactagcg gtgcccgccg aagggggagg aggcgaggag cgagccgtgc     60

ggccagagcg ggaaagagac tcgtctttgc gtccgagttc tggagccgcc gcaccccgac    120

tcctggggcc gcggcagcgg ctgcgagggg acgggcgtcc gctgtctcct gggttcccct    180

cgtagcgacc cgcgggatcg gaaaaaaagg agaagatgga ggaggagggt ggcagcagcg    240

gcggcgccgc ggggaccagc gcggacggcg gcgacggagg agagcagctc ctcactgtca    300

agcacgagct gcggactgct aatttgacag gacatgctga gaaggtggga atagaaaatt    360

ttgagctcct gaaggtccta ggaactggag cttatggaaa agtatttcta gttcgtaaaa    420

taagtggcca tgatactgga aagctgtatg ccatgaaagt tttgaaaaag gcaacaatcg    480

ttcaaaaggc caaaaccaca gagcatacaa ggacagaacg acaagtcctg gaacacatta    540

ggcagtcgcc atttttggta acattacatt atgctttcca gacagaaacc aaacttcatc    600

tcattttaga ttatataaat ggtggtgaac tttttactca tctttctcaa agagagcgtt    660

tcacagagca tgaggtgcag atttatgttg gagagattgt gcttgccctc gaacatctcc    720

acaagttggg gattatatat cgtgatatta agcttgagaa tattctactt gattctaatg    780

gccatgtggt gctgacagat tttggtctga gtaaggagtt tgtggctgat gaaactgaaa    840

gagcatattc cttttgtgga actattgaat acatggcacc agatattgtc agagggggag    900

attcaggaca tgacaaggca gttgactggt ggagtttggg tgttctaatg tatgaattac    960

taactggagc atctcctttc actgttgatg gagaaaaaaa ttcccaagct gagatatcta   1020

ggagaatatt aaaaagtgag cctccatatc cccaagaaat gagtgcttta gcgaaagacc   1080
```

```
taattcagcg tcttttgatg aaagatccca agaagagatt gggatgtggt ccacgtgatg   1140
cagatgaaat caaagaacat ctcttctttc agaaaataaa ttgggatgat ttagccgcca   1200
aaaaagtgcc tgcaccattt aagccagtca ttcgagatga attagatgtg agtaactttg   1260
cagaagagtt cacagaaatg gatcccactt attctcccgc agccctgccc cagagttctg   1320
agaagctgtt tcagggctat tcctttgttg ctccttccat cctattcaag cgtaatgcag   1380
ctgtcataga ccctcttcag tttcacatgg gagttgaacg tcctggagtg acaaatgttg   1440
ccaggagtgc aatgatgaag gactctccat tctatcaaca ctatgaccta gatttgaagg   1500
acaaacccct gggagaaggt agtttttcaa tttgtcgaaa gtgtgtgcat aaaaaaagta   1560
accaagcttt tgcagtcaaa ataatcagca aaaggatgga agccaatact caaaaggaaa   1620
taacagctct gaaactctgt gaaggacacc ccaatattgt gaagttgcat gaagtttttc   1680
atgatcagct tcacacgttt ctagtgatgg aacttctgaa tggaggagaa ctgtttgagc   1740
gcattaagaa aaagaagcac ttcagtgaga cggaagccag ctacatcatg aggaagcttg   1800
tttcagctgt aagccacatg catgatgttg gagtggtgca cagggatctg aaacctgaga   1860
atttattgtt caccgatgaa aatgacaatt tggaaattaa aataattgat tttggatttg   1920
cacggctaaa gccaccggat aatcagcccc tgaagactcc atgcttcacc cttcattatg   1980
ccgccccaga gctcttgaat cagaacggct acgatgagtc ctgtgacctg tggagcttgg   2040
gcgtcatttt gtacacaatg ttgtcaggac aggttccctt ccaatctcat gaccgaagtt   2100
tgacgtgtac cagcgcggtg gaaatcatga agaaaattaa aaagggagat ttctcctttg   2160
aaggagaagc ctggaagaat gtatcccaag aggctaaaga tttgatccaa ggacttctca   2220
cagtagatcc aaacaaaagg cttaaaatgt ctggcttgag gtacaatgaa tggctacaag   2280
atggaagtca gctgtcctcc aatcctctga tgactccgga tattctagga tcttccggag   2340
ctgccgtgca tacctgtgtg aaagcaacct tccacgcctt taacaaatac aagagagagg   2400
ggttttgcct tcagaatgtt gataaggccc ctttggctaa gagaagaaaa atgaaaaaga   2460
ctagcaccag taccgagacg cgcagcagtt ccagtgagag ttcccattct tcttcctctc   2520
attctcacgg taaaactaca cccaccaaga cactgcagcc cagcaatcct gccgacagca   2580
ataacccgga gaccctcttc cagttctcgg actcagtagc ttaggcatgg taggagtgta   2640
tcagtgatcc attgcacctt tattccctca gcatatgcct gaggcgatct tttatgcttt   2700
taaaaatgtt tcccgttggt ctcattggaa tctgcctcct aatgattttt ttcaggaaaa   2760
cctgtttggt tatcctcatt caaaagcact ggacagagaa tgttactgtg aatagagcac   2820
atattactct ttttagcaac ctagcatgat gccaacaaga ctattcttga aagagcaaag   2880
gttcctgtaa atttaattag ggctagattt gagctgcttg taagtcacag gttttccaga   2940
tgtctgccaa caagaaatga ctcatactgt gatgatacct tttgctttgc cttgtggaca   3000
atgtgggttt ttgaaatttg cacccttcaa acaatgattt atcagagaaa ggggtctgtt   3060
ttcaaaaaag attctgtaat gaattttatg tgtggcatat acttatttct tgagagaaga   3120
ttttaactta ttgtttttat tttatggtta catatgatga taacctgcta ttattaaact   3180
ttttctaaaa agtgaaaaaa aaaaaaaaag atataagaac tcaaggtccc atactctgta   3240
ttcgggatcc atctgagatg catgctaagc tatgtgtatg tttttaattt tgcactgctc   3300
tttcctggca atttgtttta atggttattg cagaatatta aggtacatgt ctctctgttt   3360
taagtaatat tgcactttat aaaaaagtat gaataaagca aactatttta taaagtgcac   3420
```

-continued

```
tgtttaaagc atttgcactg tatttttgcc atttattttc attttctact ttaaatttgt   3480

cctcacattc ctcttctact ttgtatgcaa caagtagaat ggggcatgtt gtgtcatgta   3540

gtcagccact tatgcaccaa tgtgaggaaa acctaaaggg aaattaaact aaacactgtg   3600

cttcatattt gtacactgtg ttgtactaca gtgaggaatt tcctcctgta gtcatatatt   3660

atgtacataa tattttagaa tcatacctat gacttgtttg gaaatttttc tgttaaattt   3720

taaatccaga aagcatattt tataaactta tgcagagcac ttttattgct caaaagttct   3780

gaattcatac agaaaacaag tactatgtga tgaaaacatt tcattaaaag attgctgcat   3840

ttaaaaatac aattaattcg ttccctatgc aaaaaaaaaa aaa                     3883


<210> SEQ ID NO 25
<211> LENGTH: 1229
<212> TYPE: DNA
<213> ORGANISM: Homo sapiens

<400> SEQUENCE: 25

cttgcctgct tctctggccc ctggtcctgt cctgttctcc agcatggtgt gtctgaagct     60

ccctggaggc tcctgcatga cagcgctgac agtgacactg atggtgctga gctccccact    120

ggctttgtct ggggacaccc gaccacgttt cctgtggcag cctaagaggg agtgtcattt    180

cttcaatggg acggagcggg tgcggttcct ggacagatac ttctataacc aggaggagtc    240

cgtgcgcttc gacagcgacg tgggggagtt ccgggcggtg acggagctgg ggcggcctga    300

cgctgagtac tggaacagcc agaaggacat cctggagcag gcgcgggccg cggtggacac    360

ctactgcaga cacaactacg gggttgtgga gagcttcaca gtgcagcggc gagtccaacc    420

taaggtgact gtatatcctt caaagaccca gcccctgcag caccacaacc tcctggtctg    480

ctctgtgagt ggtttctatc caggcagcat tgaagtcagg tggttcctga acggccagga    540

agagaaggct gggatggtgt ccacaggcct gatccagaat ggagactgga ccttccagac    600

cctggtgatg ctggaaacag ttcctcgaag tggagaggtt tacacctgcc aagtggagca    660

cccaagcgtg acaagccctc tcacagtgga atggagagca cggtctgaat ctgcacagag    720

caagatgctg agtggagtcg gggctttgt gctgggcctg ctcttccttg gggccgggct    780

gttcatctac ttcaggaatc agaaaggaca ctctggactt cagccaacag gattcctgag    840

ctgaaatgca gatgaccaca ttcaaggaag aactttctgc cccggctttg caggatgaaa    900

agctttcctg cttggcagtt attcttccac aagagagggc tttctcagga cctggttgct    960

actggttcgg caactgcaga aaatgtcctc ccttgtggct tcctcagctc ctgcccttgg   1020

cctgaagtcc cagcattgat ggcagcgcct catcttcaac ttttgtgctc ccctttgcct   1080

aaaccgtatg gcctcccgtg catctgtatt caccctgtat gacaaacaca ttacattatt   1140

aaatgtttct caaagatgga gttaaaaaaa aaaaaaaaaa aaaaaaaaaa aaaaaaaaaa   1200

aaaaaaaaaa aaaaaaaaaa aaaaaaaaa                                     1229
```

GENES ASSOCIATED WITH POSTTRAUMATIC-STRESS DISORDER (PTSD)

RELATED APPLICATION

This application claims the benefit of and priority to European application serial number 08016126.8 (EP) filed on 12 Sep. 2008 and International application serial number PCT/EP2009/061890 filed on 14 Sep. 2009 the contents of which are herein incorporated by reference in their entirety for any and all purposes.

SEQUENCE LISTING

The instant application contains a Sequence Listing that has been submitted via EFS-Web and is hereby incorporated by reference in its entirety. Said ASCII copy, created on Oct. 2, 2009, is named VOS0001US.txt, and is 114,310 bytes in size.

The present invention relates to a method of identifying a predisposition for developing posttraumatic stress disorder (PTSD) in a subject comprising assessing in a sample obtained from said subject the expression level of one or more genes selected from the FK506 binding protein 5 (FKBP5) gene, the signal transducer and activator of transcription (STAT5B) gene and the nuclear factor I/A (NFIA) gene, wherein a decrease in the expression level of said one or more genes as compared to the expression level of the corresponding gene(s) of a control is indicative of a predisposition for developing PTSD. Further, the invention relates to a method of identifying a compound capable of preventing or treating PTSD or capable of serving as a lead compound for developing a compound capable of preventing or treating PTSD and also to a method of selecting a therapy to prevent or treat PTSD.

In this specification, a number of documents including patent applications and manufacturer's manuals are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

The risk for the individual to get exposed by life-threatening events like natural disasters, accidents, attacks, assaults and other acts of violence, not to mention terrorist attacks, has considerably increased during the past decades. All these incidents can trigger the development of stress-related disorders. This includes the so called posttraumatic-stress disorder (PTSD), which is characterized by persistent and frightening re-experiencing of the traumatic event, accompanied by severely impairing sleep disturbances and avoidance behaviour. Besides PTSD, which is directly linked to a specific traumatic experience, also anxiety disorders and depression can be triggered by adverse events.

Posttraumatic stress disorder (PTSD) occurs in only a small proportion of those exposed to traumatic events. Several risk factors have been implicated in the development of PTSD. These include age at traumatization, gender, earlier childhood exposures (i.e., "pre-traumatic") to adversity, personality characteristics, and familial psychopathology, including PTSD (Yehuda R, LeDoux J, Neuron 2007; 56: 19-32). There is evidence from twin studies that genetic factors contribute to the risk for PTSD (Stein et al., Am J Psychiatry 2002; 159: 1675-81; True et al., Arch Gen Psychiatry 1993; 50: 257-264; Xian et al., Drug Alcohol Depend 2000;

61: 95-102). However, susceptibility genes have not been confirmed in PTSD (Broekman et al., Neurosci Biobehav Rev 2007; 31: 348-62).

PTSD is on the molecular level characterized by a disturbed regulation of the primary stress-hormone system, the so-called HPA (hypothalamic-pituitary-adrenal) axis. The hypothalamic-pituitary-adrenal (HPA) axis is the major constituent of the neuroendocrine response to acute and chronic stress, resulting in the release of corticotropin releasing hormone (CRH) and vasopressin (AVP) from the parvocellular neurons of the hypothalamus into the portal vessels system to activate the synthesis and release of ACTH from the anterior pituitary. In turn, ACTH stimulates the adrenal cortex to synthesize and release glucocorticoids, in particular cortisol (de Kloet et al., Nat Rev Neurosci 2005; 6: 463-75). In PTSD, the fine-tuned regulation of this HPA axis is disturbed, which is indicated by reduced levels and an exaggerated responsiveness of ACTH and cortisol in these patients. Enhanced responsiveness of the glucocorticoid receptor (GR) appears to underlie these disturbances. These findings contrast with observations of greater cortisol levels and reduced GR responsiveness associated with major depression (Ribeiro et al., Am J Psychiatry 1993; 150: 1618-29; Holsboer F, Neuropsychopharmacology 2000; 23: 477-501).

Though initially interpreted as reflecting enduring consequences of trauma exposure, there has been reason to suspect that HPA axis alterations in PTSD reflect pre-traumatic risk factors. In several longitudinal studies, lower cortisol levels in the acute aftermath of trauma were associated with either the subsequent development of PTSD, or with the well-established risk factor of prior trauma exposure (e.g., childhood traumatisation) (Yehuda et al., Am J Psychiatry 2005; 162: 998-1000; Neylan et al., Psychoneuroendocrinology 2005; 30: 373-8; Oquendo et al., Neuropsychopharmacology 2003; 28: 591-8; King et al., Psychiatry Clin Neurosci 2001; 55: 71-4; Heim et al., Psychoneuroendocrinology 2000; 25: 1-35; Yehuda et al., Biol Psychiatry 1996; 40: 79-88; Lemieux A M, Coe C L, Psychosom Med 1995; 57: 105-15; Glover D A, Poland R E, Psychoneuroendocrinology 2002; 27: 805-19; Young E A, Breslau N, Arch Gen Psychiatry 2004; 61: 394-401; Pitman R K, Orr S P, Biol Psychiatry. 1990; 27: 245-7; Baker et al., Am J Psychiatry 2005; 162: 992-4). Recent studies of infant and adult children of parents with PTSD also support the idea that both low cortisol levels, and glucocorticoid responsiveness are risk factors for PTSD (Yehuda et al., J Clin Endocrinol Metab 2005; 90: 4115-8; Yehuda R, Bierer L M, Prog Brain Res 2008; 167: 121-35). These findings raised the possibility that reduced cortisol levels at the time of a traumatic exposure may compromise the inhibition of stress-induced biologic responses (e.g., during and following a traumatic event), resulting in prolonged physiological/emotional distress which would then facilitate the development of PTSD (Yehuda R, N Engl J Med 2002; 346: 108-14). Accordingly, the identification of biological processes that underpin enhanced GR responsiveness and/or lower cortisol levels are of particular interest. Indeed, it was recently observed that adults who experienced child abuse and have genetic variations in the FKBP5 gene (involved in the regulation of the GR) appear to be at greater risk of PTSD symptoms as adults (Binder et al., JAMA 2008; 299: 1291-305).

There have been two other studies examining gene expression following trauma exposure. In a study of persons exposed to severe trauma encountered in the emergency room who either did (n=8), or did not (n=6) meet criteria for PTSD at both a 1 month and 4 month follow-up, gene expression changes associated with several interesting molecular categories related to the stress response (Segman et al., Mol Psychiatry 2005; 10: 500-13, 425). Interestingly, the expression of FKBP5 was shown to be upregulated in this study. Given the proximity to trauma exposure, however, the findings may have reflected biological changes associated with recovering from the effects of trauma exposure, rather than with the development or persistence of chronic PTSD. A whole blood gene expression profiling study of 16 subjects (n=8 with PTSD) exposed to the Ramstein Airshow tragedy (16 years ago) attempted to examine processes associated with very chronic PTSD. This study used a special microarray chip modified to specifically detect genes associated with the immune and stress responses (Zieker et al., Mol Psychiatry 2007; 12: 116-8). Interestingly, little overlap in gene expression was reported in the two studies. Both studies reported on very few subjects, and neither study examined risk factors other than exposure to the focal trauma.

Even though effective psychopharmacological treatments and psychotherapeutic programs are available for PTSD, their efficiency is limited by the fact that they will not be initiated until the full-blown symptoms of the stress-related disorder-have occurred. At this stage of the disorder, the patients are already severely impaired, and it takes long time until full remission of the symptoms can be achieved.

The technical problem underlying the present invention was to identify improved means and methods for diagnosing PTSD.

The solution to this technical problem is achieved by providing the embodiments characterized in the claims.

Accordingly, the present invention relates in a first embodiment to a method of identifying a predisposition for developing posttraumatic stress disorder (PTSD) in a subject comprising assessing in a sample obtained from said subject the expression level of one or more genes selected from the FK506 binding protein 5 (FKBP5) gene, the signal transducer and activator of transcription (STAT5B) gene and the nuclear factor I/A (NFIA) gene, wherein a decrease in the expression level of said one or more genes as compared to the expression level of the corresponding gene(s) of a control is indicative of a predisposition for developing PTSD.

The term "predisposition for a disease" is established in the art and used herein analogously. The term "predisposition for developing posttraumatic stress disorder (PTSD)" as used in accordance with the present invention describes the status of a patient at risk to develop said disease once exposed to a trauma. A predisposition may be based on environmental, genetic and/or epigenetic factors. As used herein, the predisposition to develop PTSD is based on epigenetic factors affecting the expression of genes. Said predisposition to develop PTSD may be diagnosed according to the method of the invention upon exposure to a traumatic event as well as prior to exposure to said event.

"Posttraumatic stress disorder" as used herein relates to a condition characterized by the development of characteristic symptoms following exposure to a traumatic stressor such as direct personal experience of an event that involves actual or threatened death or serious injury, or other threat to one's physical integrity; or witnessing an event that involves death, injury, or a threat to the physical integrity of another person; or learning about unexpected or violent death, serious harm, or threat of death or injury experienced by a family member or other close associate. The person's response to the event generally involves intense fear, helplessness, or horror. In children, the response generally involves disorganized or agitated behavior. The characteristic symptoms resulting from the exposure to the extreme trauma include persistent reexperiencing of the traumatic event, persistent avoidance of stimuli associated with the trauma and numbing of general responsiveness, and persistent symptoms of increased arousal. In Posttraumatic Stress Disorder, the stressor is generally of extreme nature (c.f. above). In contrast, in Adjustment Disorder, the stressor can be of any severity. The diagnosis of Adjustment Disorder is appropriate both for situations in which the response to an extreme stressor does not meet the criteria for Posttraumatic Stress Disorder (or another specific mental disorder) and for situations in which the symptom pattern of Posttraumatic Stress Disorder occurs in response to a stressor that is not extreme (e.g., spouse leaving, being fired). Symptoms of avoidance, numbing, and increased arousal that are present before exposure to the stressor do not meet criteria for the diagnosis of Posttraumatic Stress Disorder and require consideration of other diagnoses (e.g., Brief Psychotic Disorder, Conversion Disorder, Major Depressive Disorder), these diagnoses should be given instead of, or in addition to, Posttraumatic Stress Disorder. Acute Stress Disorder is distinguished from Posttraumatic Stress Disorder because the symptom pattern in Acute Stress Disorder must occur within 4 weeks of the traumatic event and resolve within that 4-week period. If the symptoms persist for more than 1 month and meet criteria for Posttraumatic Stress Disorder, the diagnosis is changed from Acute Stress Disorder to Posttraumatic Stress Disorder. For example, severity of PTSD symptoms can be evaluated by using the Modified PTSD Symptom Scale (PSS) (Coffey et al., *J Trauma Stress* (1998), 11: 393-399; Falsetti et al., *Behav Therapist* (1993), 16: 161-162).

The term "expression level of one or more genes" as used in accordance with the method of the invention relates to the degree of gene expression of one or more genes. The term "gene expression" relates to a process by which information from a nucleic acid (e.g., DNA or RNA) sequence such as, e.g., a gene, is processed into a gene product (e.g., RNA or peptide/protein). Said process can be subdivided into a transcriptional and a translational process. Transcription describes in the context of gene expression the process of transcribing DNA into mRNA, whereas translation describes the process of translating mRNA into a peptide or protein. The term "peptide" as used herein describes a group of molecules consisting of up to 30 amino acids, whereas "proteins" consist of more than 30 amino acids. Peptides and proteins may further form dimers, trimers and higher oligomers, i.e. consisting of more than one molecule which may be identical or non-identical. The corresponding higher order structures are, consequently, termed homo- or heterodimers, homo- or heterotrimers etc. The terms "peptide" and "protein" (wherein "protein" is interchangeably used with "polypeptide") also refer to naturally modified peptides/proteins wherein the modification is effected e.g. by glycosylation, acetylation, phosphorylation and the like. Such modifications are well-known in the art. In accordance with the invention, the expression level of one or more of the genes selected from FKBP5, STAT5B and NFIA and combinations thereof such as FKBP5, STAT5B and NFIA; FKBP5 and STAT5B; FKBP5 and NFIA; or STAT5B and NFIA can be assessed.

The assessment of "expression levels", i.e. of the degree of expression, is the decisive factor in the process of diagnosing a risk to develop PTSD in accordance with method of the present invention. The term "level" as used in connection with gene expression in accordance with the present invention relates to the readout of any quantitative measure of gene expression. Said measure is dependent on, preferably at least roughly proportional to the number of mRNA molecules or peptide or protein molecules, hence allowing a quantitative assessment of gene expression. Depending on the means and methods employed for said quantitative measure the determined level of gene expression may be in the form of a variety of readout parameters, e.g., the intensity of a radioactivity signal (e.g., Northern blot with a radioactive probe), of a fluorescent signal (e.g., DNA microarray) or the mass-to-charge ratio (e.g., mass spectrometry). Means and methods that allow to quantitatively determine gene expression levels are well known in the art and non-limiting examples are further detailed herein below. The expression levels of genes generally and normally vary from subject to subject depending on age, sex and/or condition, inter alia, to a certain extent. Variations to be considered not normal, e.g. variations linked to a disease, have to be statistically significant when compared to a suitable control population.

Generally speaking, in healthy subjects expression levels are expressed at certain ratios contributing in concerted action to normal body functions. Disturbances, such as an upregulation and/or downregulation of one or more genes, in gene expression levels may lead to a medical condition if endogenous rescue mechanisms do not exist that can compensate for said disturbances. Several steps in the gene expression process may be modulated to regulate the expression level of a gene such as, e.g. the step of initiating the transcription process involving the amount of transcription factors, the presence of so called operons (e.g. lac operon) or enhancer/inhibitory sequences, the step of translation involving the half-life of the mRNA to be translated, the posttranslational modification of a protein having an effect on the half-life, the secretion, the folding of the latter. Gene regulation gives cells control over structure and function and is the basis for events like differentiation, morphogenesis or adaptability of a cell or a multicellular organism. In summary, the assessment of expression levels may prove in some cases to be a suitable tool for diagnosing or predicting a medical condition.

In the present case, the expression level of the genes FKBP5, STAT5B and NFIA were surprisingly found to be disturbed, i.e. downregulated, in subjects having PTSD.

The skilled person is well aware of the molecular details involved in gene expression and there exists ample literature in said field (cf., e.g., Lodish et al., Molecular Cell Biology; W.H. Freeman & Co, New York; Alberts et al., Molecular Biology of the Cell, Garland Science, New York and London; G. M. Cooper, The Cell—A Molecular Approach, Sinauer Associates, Inc. Sunderland (Ma); Griffiths et al., Modern Genetic Analysis, W.H. Freeman, New York). Methods for "assessing" gene expression are also well-known to the person skilled in the art and part of the latter referenced textbooks.

The human FK506 binding protein 5 (FKBP5) gene located on chromosome 6 (6p21.3-p21.2) encodes the FK505 binding protein 5. This protein is a member of the immunophilin protein family, which play a role in basic cellular processes involving protein folding and trafficking. FK506-binding protein 5 is a so-called co-chaperone molecule interacting with the heat-shock protein 90 in an inactive glucocorticoid receptor complex. It is a negative regulator of glucocorticoid action by reducing the binding affinity of glucocorticoid receptors (Denny et al., *Endocrinology* 2000; 141: 4107-113). Preferably, the FKBP5 gene has a coding sequence as shown in SEQ ID NO: 1. However, as also variant or homologous alleles of the FKBP5 gene may exist the gene can also have a coding sequence being at least 95% identical to the sequence of SEQ ID NO:1 such as, being at least 96%, or preferably 97%, more preferred 98% and most preferred at least 99% identical.

The signal transducer and activator of transcription (STAT5B) gene located on chromosome 17 (17q11.2) encodes the STAT5B protein. This protein is a member of the STAT family of transcription factors and mediates the signal transduction triggered by various cell ligands, such as IL2, IL4, CSF1, and different growth hormones. This protein acts as a direct inhibitor of the nuclear translocation of activated glucocorticoid receptors (Goleva et al., *J Immunol* 2002; 169: 5934-40; Biola et al., *Mol Endocrinol* 2001; 15: 1062-76) thus reducing the effects of activated glucocorticoid receptors. Preferably, the STAT5B gene has a coding sequence as shown in SEQ ID NO: 2. However, as also variant or homologous alleles of the STAT5B gene may exist the gene can also have a coding sequence being at least 95% identical to the sequence of SEQ ID NO:2 such as, being at least 96%, or preferably 97%, more preferred 98% and most preferred at least 99% identical.

The nuclear factor I/A (NFIA) gene located on chromosome 1 (1p31.3-2) encodes the NFIA protein. This protein is a member of the Nuclear factor I (NFI) protein family, which are dimeric DNA-binding proteins with similar, and possibly identical, DNA-binding specificity. They function as cellular transcription factors and as replication factors for adenovirus DNA replication. The NFIA protein modulates the effects of activated glucocorticoid receptors at their target structures (Hebbar, Archer, *J Biol Chem* 2007; 282: 8284-91). Preferably, the NFIA gene has a coding sequence as shown in SEQ ID NO: 3. However, as also variant or homologous alleles of the NFIA gene may exist the gene can also have a coding sequence being at least 95% identical to the sequence of SEQ ID NO:3 such as, being at least 796%, or preferably 97%, more preferred 98% and most preferred at least 99% identical.

The designation of the genes when written out is interchangeable with the term in parentheses which is used as an abbreviation herein. For example, the FK506 binding protein 5 gene may also be described by using the term "FKBP5" or "FKBP5 gene", the meaning is identical.

The term "sample" as used herein refers to a biological sample, such as, for example, cells, tissues (from any organ including post-mortem brain tissue), or fluids (including serum, whole blood, cerebrospinal fluid, lymph, saliva, milk, pus, urine, faeces), which has been isolated or obtained from an individual or from cell culture constituents of a cell culture comprising a subject's cells. Any tissue or liquid sample obtained from a patient and/or subject that comprises cells can be used for the assessment of expression levels of the one or more genes according to the method of the invention. It is well known in the art that nucleic acids such as, e.g., mRNA, and proteins of individuals can easily be obtained from blood samples. Thus, a preferred sample to assess gene expression levels in accordance with the method of the invention is blood. Methods for preparing the sample for nucleic acid and protein extraction are well known in the art, and can be carried out using commercially available kits such as, for example, the PAXgene™ RNA Systems (Qiagen), RNeasy™ Kits (Qiagen) or protocols using TRIzol® reagent (Invitrogen).

In order to identify a predisposition for developing PTSD, the gene expression level(s) in a sample of a subject suspected to be predispositioned to develop PTSD are compared to the expression level(s) of the corresponding gene(s) in a control. Preferably a control is selected from i) a control subject that has been exposed to a trauma, but did not develop PTSD, ii) a group of subjects negative for PTSD and representative for the investigated population and iii) database entries. As mentioned above, a control subject has been exposed to a trauma, but did not develop PTSD. Preferred control subjects did not develop PTSD within 6 months from the exposure to trauma. Alternatively, the range of expression levels obtained from a group of subjects negative for PTSD and representative for the investigated population can be used as normal values. A "trauma" as referred to herein is the direct personal experience of an event that involves actual or threatened death or serious injury, or other threat to one's physical integrity; or witnessing an event that involves death, injury, or a threat to the physical integrity of another person; or learning about unexpected or violent death, serious harm, or threat of death or injury experienced by a family member or other close associate. Preferred is that a sample of a control subject is assessed more than once or that several samples of said control subject are obtained in order to increase the reliability of the data relating to the expression level. The data may further be pooled to calculate the mean or median and optionally the variance for each control subject. Furthermore preferred is that the expression level(s) are compared to the expression level(s) of corresponding gene(s) in samples of more than one control subject such as at least 2, 10, 20 or more preferred 50, and most preferred 100 and more control subjects. Furthermore also preferred is that the expression levels of the samples of the control subjects are pooled and the mean or median and optionally the variance is calculated. These values may, e.g., be deposited into a database as a standardized value for each gene and if required retrieved from a database, hence making the need to also experimentally assess the expression levels in a control sample every time the expression level in a patient sample is assessed dispensable. Accordingly a control may also be a database entry. Moreover, by using the variance of the expression level of the control sample, the statistical significance of deviations from the mean of controls in the sample to be assessed may be determined. Finally, and where deemed appropriate, age- or gender-specific controls may be used.

In accordance with the present invention, for the first time an association of gene expression and a predisposition to PTSD is demonstrated, wherein the genes are involved in the regulation of the HPA axis. In brief, 20 participants meeting criteria for lifetime PTSD, assessed five years after the attack on the World Trade Center (WTC), i.e. after "9/11", and 20 participants matched with respect to severity of exposure to 9/11, age, gender, and race were recruited for the purpose of performing whole blood genome-wide expression analysis to identify altered gene activity patterns as risk factors for PTSD. Also, interactions between gene expression and PTSD severity were evaluated.

It could be demonstrated that the expression of genes encoding for FKBP5, STAT5B and NFIA proteins is differentially regulated in individuals diagnosed with PTSD in comparison to control individuals. Without being bound by a specific theory, it is considered that in response to stress, glucocorticoids are secreted from the cortex of the adrenal glands and subsequently exert diverse activities by binding at glucocorticoid receptors (GRs), which in turn are also the key regulatory element of the HPA axis. Briefly and in accordance with the description in the background section above, the hypothalamic-pituitary-adrenal (HPA) axis is involved in the neuroendocrine response to stress by triggering the release of corticotrophin releasing hormone (CRH) and vasopressin (AVP). Via a signal cascade involving, inter alia, ACTH glucocorticoids, in particular cortisol, are synthesized and released subsequently interacting with glucocorticoidreceptors (GRs). FKBP5 codes for a protein that modulates GR function by decreasing GR binding affinity for glucocorticoids, and thus reduces the sensitivity of this receptor. STAT5B and NFIA modulate the effects of GR by inhibiting their translocation to the target structure (STAT5B) or alter the effects of GR at their target structure (NFIA). In other words, FKBP5, STAT5B and NFIA are functionally related in that they modulate the activity of the HPA axis. Moreover, they act on a common pathway in that they control the sensitivity of the glucocorticoid receptors. On the molecular level, the reduced expression levels of FKBP5 and STAT5B lead to hypersensitive and hyperactive GR, which in turn results in a severe imbalance of the stress-hormone regulation. Reduced NFIA expression acts as a counterregulator of the increased GR activity by reducing GR binding at specific transcription factor sites. These findings match abnormal glucocorticoid levels frequently observed in PTSD. In this context, it is interesting to note that genetic polymorphisms in the FKBP5 gene, but not expression level alterations, have been previously identified as risk factors for the development of PTSD symptoms in children who were victims of severe accidents as well as in adults who were exposed to traumatic experiences at young age. Thus, with FKBP5, STAT5, and NFIA three genes directly involved in the actions of GR could be identified.

With the diagnostic method of the invention, an imminent risk for the development of PTSD can be identified, and medical interventions can be initiated at a very early stage of the disease process. Such a diagnostic method can be applied to individuals, who, for instance, just recently experienced a traumatic event like a natural disaster, an accident, attacks, assaults or other acts of violence. Individuals with a diminished expression level of these genes should receive immediate preventive medical attention to avoid the development of PTSD. Such a procedure will help to maintain health in many traumatized subjects who otherwise would be at risk to develop overt symptoms. Assessment of FKBP5, STAT5B, and/or NFIA gene expression levels will identify subjects who will benefit from preventive medical intervention, thus saving the health of the individual and reduce costs for the health-care system.

In a preferred embodiment of the method of the invention, additionally the expression level of one or both genes selected from the mannosidase, alpha, class 2C, member 1 (MAN2C1) gene; and DEAD box polypeptide 17 (DDX17) gene is assessed, wherein an increase in expression level said gene(s) as compared to the expression level of the corresponding gene(s) of a control is indicative of a predisposition for developing PTSD.

In a further preferred embodiment of the method of the invention, additionally the expression level of one or more further genes selected from the copine I (CPNE1) gene; tuberous sclerosis 1 (TSC1) gene; ADAM metallopeptidase domain 17 (ADAM17) gene; ring finger protein 181 (RNF181) gene; myosin IC (MYO1C) gene; MOB1, Mps One Binder kinase activator-like 1B (MOBKL1B) gene; glucosidase, beta, acid (GBA) gene; chromosome 2 open reading frame 34 (C2orf34) gene; transmembrane protein 167A (TMEM167A) gene; microtubule associated serine/threonine kinase family member 4 (MAST4) gene; N-acylsphingosine amidohydrolase (ASAH1) gene; CGG triplet repeat binding protein 1 (CGGBP1) gene; family with sequence similarity 175, member B (FAM175B) gene; bridging integrator 1 (BIN1) gene; kruppel-like factor 12 (KLF12) gene; methyltransferase like 7A (METTL7A) gene; transmembrane protein 49 (TMEM49) gene; ribosomal protein S6 kinase, 90 kDa, polypeptide (RPS6KA5) gene; and major histocompatibility complex, class II, DR beta (DR HLA-DRB1) gene; is assessed, wherein a decrease of the expression level of any one of said genes as compared to the expression level of the corresponding gene(s) of a control is indicative of a predisposition for developing PTSD.

Also in accordance with the invention, each of the above recited genes associated with the risk of developing PTSD is, when assessed on its own, i.e. without a second gene, suitable for predicting the risk of developing PTSD.

Preferably, the MAN2C1 gene has a coding sequence as shown in SEQ ID NO: 4; the DDX17 gene has a coding sequence as shown in SEQ ID NO: 5; the CPNE1 gene has a coding sequence as shown in SEQ ID NO: 6; the TSC1 gene has a coding sequence as shown in SEQ ID NO: 7; the ADAM17 gene has a coding sequence as shown in SEQ ID NO: 8; the RNF181 gene has a coding sequence as shown in SEQ ID NO: 9; the MYO1C gene has a coding sequence as shown in SEQ ID NO: 10; the MOBKL1B gene has a coding sequence as shown in SEQ ID NO: 11; the GBA gene has a coding sequence as shown in SEQ ID NO: 12; the C2orf34 gene has a coding sequence as shown in SEQ ID NO: 13; the TMEM167A gene has a coding sequence as shown in SEQ ID NO: 14; the MAST4 gene has a coding sequence as shown in SEQ ID NO: 15 or 16; the ASAH1 gene has a coding sequence as shown in SEQ ID NO: 17; the CGGBP1 gene has a coding sequence as shown in SEQ ID NO: 18, the FAM175B gene has a coding sequence as shown in SEQ ID NO: 19; the BIN1 gene has a coding sequence as shown in SEQ ID NO: 20; the KLF12 gene has a coding sequence as shown in SEQ ID NO: 21; the METTL7A gene has a coding sequence as shown in SEQ ID NO: 22; the TMEM49 gene has a coding sequence as shown in SEQ ID NO: 23; the RPS6KA5 gene has a coding sequence as shown in SEQ ID NO: 24; and the DR HLA-DRB1 gene has a coding sequence as shown in SEQ ID NO: 25. However, as also variant or homologous alleles of any of the above described genes may exist the latter gene(s) can also have a coding sequence being at least 95% identical to the sequence as depicted in the SEQ ID NO assigned to the gene such as, being at least 96%, or preferably 97%, more preferred 98% and most preferred at least 99% identical.

Besides assessing one or more of the genes selected from FKBP5, STAT5B and NFIA and combinations thereof in this embodiment it is preferred that the predictive power of the method of the invention is further increased by additionally assessing the expression levels of any one of the above-recited genes. Said genes have been demonstrated to also be significantly associated with the risk to develop PTSD and are hence suitable as molecular predictors of said risk to develop PTSD. In accordance with the method of the invention, any combination of genes may be chosen for identifying a predisposition to develop PTSD as long as at least one of FKBP5, STAT5B or NFIA is also assessed in accordance with the method of the invention. It is preferred that more than one additional gene is assessed, such as at least 2, 3, 4, 5, 6, 7, 8, more preferred at least 9, most preferred at least 10. Also, envisaged is the assessment of more than 10 additional genes such as at least 11, 12, 13, 14, 15, 16, 17, 18, 19, 20 or at least 21 genes. The selection of additional genes to be assessed is preferably based on the significance of association of the single genes as experimentally shown herein (cf. Table 1). A selection is advantageously based upon the reasoning that the lesser the association significance of a gene is, the more genes have to be assessed in order to be able to make a more substantiated diagnosis. The assessment of further genes that have been previously identified or will in the future be identified to be associated with PTSD which are not recited in this specification can be additionally assessed.

The same applies mutatis mutandis for other embodiments recited herein below.

In another preferred embodiment of the method of the invention, additionally the expression level of the MAN2C1 gene is assessed, wherein an increase of the expression level of the MAN2C1 gene as compared to the expression level of the corresponding gene of a control is indicative of a predisposition for developing PTSD.

In a further preferred embodiment of the method of the invention, additionally the expression level of one or more genes selected from CPNE1; ADAM17; and METTL7A is assessed, wherein a decrease of the expression level of any one of said genes as compared to the expression level of the corresponding gene(s) of a control is indicative of a predisposition for developing PTSD.

In another aspect of the studies performed by the present inventors they were able to establish a link between differential gene expression and symptom severity. Besides showing that differential expression of the genes identified herein above is associated with PTSD they could also demonstrate which of the identified differentially expressed genes correlates with the severity of PTSD. It was shown by regression analysis that the expression level of each of the genes MAN2C1, CPNE1, ADAM17 and METTL7A was significantly associated with PTSD symptom severity. In particular, an increased expression level of MAN2C1 or a decreased expression level of CPNE1, ADAM17 or METTL7A is indicative of the severity of the PTSD symptoms. Said association means that a weak dysregulation of expression is indicative of weak symptoms, while a strong dysregulation is indicative of strong symptoms. The severity of symptoms can be determined by standardized clinical rating procedures that are well-known in the art such as, e.g., the Clinician-Administered PTSD Scale (CAPS), which is a structured interview for assessing frequency and severity of the core and associated symptoms of PTSD using standard prompt questions and behaviourally-anchored rating scales (Blake D D et al. J Trauma Stress 1995; 8: 75-90). From the obtained responses, a general severity score can be calculated. Hence, when assessing the expression levels of the latter genes, the diagnostic conclusion may be twofold, i.e. (i) the patient is at risk for developing PTSD or not and (ii) if at risk the symptoms will be severe. The same applies—correspondingly adapted—to other embodiments recited herein below.

In a further embodiment the invention relates to a method of identifying a compound capable of preventing or treating PTSD or capable of serving as a lead compound for developing a compound capable of preventing or treating PTSD, the method comprising the steps of: (a) assessing the expression level of one or more genes selected from the FK506 binding protein 5 (FKBP5) gene, the signal transducer and activator of transcription (STAT5B) gene and the nuclear factor I/A (NFIA) gene in a cell contacted with a test compound or in a sample obtained from a subject and contacted with said test compound; and (b) assessing the expression level of said one or more gene(s) in a cell or a sample obtained from a subject, wherein said cell or sample was i) not contacted with said test compound; ii) contacted with a compound known to not affect the expression levels of said gene(s) of step (a), wherein an increase of the expression level of the gene(s) in step (a) as compared to step (b) i) or (b) ii) is indicative of said test compound being capable of preventing or treating PTSD or serving as a lead compound for developing a compound capable of preventing or treating PTSD; or iii) contacted with a compound known to enhance the expression level of said gene(s) of step (a), wherein an essentially equal level of expression or an increase of the expression level of the gene(s) in step (a) as compared to step (b) iii) is indicative of the compound being capable of preventing or treating PTSD or serving as a lead compound for developing a compound capable of preventing or treating PTSD.

Methods for the assessment of expression levels are well-known in the art and some are exemplarily described herein.

The expression level of the one or more genes is to be assessed in a cell or in a sample obtained from a subject contacted with the test compound. Said cell may be part of a cell culture colony derived from an established cell line. Also, the cell may be part of a primary cell culture established from a sample of a subject contacted with the test compound. Suitable samples obtained from subjects for the assessment of expression levels are described herein elsewhere and may also be processed without prior steps, such as establishing a primary cell culture, in order to assess expression levels.

The term "compound" as used herein relates to a substance that may be solid, semisolid, semifluid, fluid or gaseous. Said compound may, however, also be comprised in a mixture, extract or composition.

The compound that is identified according to the method of the invention to be capable of preventing or treating PTSD or capable of serving as a lead compound for developing a compound capable of preventing or treating PTSD increases the gene expression levels of said one or more genes selected from FKBP5, STAT5B and NFIA which may, for example, be based on its inhibitory, promoting, agonistic or antagonistic activity in a direct or indirect interaction with the gene or any intermediate or final gene product(s). Said compound(s) may be chemically synthesized or produced via microbial fermentation but can also be comprised in, for example, samples, e.g., cell extracts from, e.g., plants, animals or microorganisms. Furthermore, said compound to be identified by the method of the invention may be known in the art but hitherto not known to be useful as a compound capable of preventing or treating PTSD.

The term "contacting a cell" with a compound in accordance with the method of the invention relates to the process of exposing the cell to a compound to be tested and allowing interaction of said compound with the cell. Depending on the potential mode of action of the compound to be tested the interaction may take place extracellularly and/or intracellularly resulting in the increase of the expression level of the genes FKBP5, STAT5B and/or NFIA—provided the compound is capable thereof. For example, a compound may bind to the cell surface and trigger a signal cascade resulting in increased expression of said target gene(s). However, preferably the compound is exposed to the cell under conditions allowing both extracellular interaction and the uptake into the cell, in particular the cytoplasma or nucleus, to exert its potential activity on regulatory events in the gene expression process of the target gene(s). The person skilled in the art is aware of conditions generally suitable for uptake of compounds such as, e.g., proteins or nucleic acid molecules, into cells and methods to enhance said uptake as regards rate and amount wherein said enhancement may include artificially modifying, e.g, proteins (see, for example, Patsch et Edenhofer, (2007), Handb. Exp. Pharmacol., 178, 203-232) or nucleic acids. Furthermore, he is also aware of cell lines naturally exhibiting the capacity of increased uptake capabilities relative to other cells. Such cells are, for example, cells like mucosal cells or intestinal cells. A number of mechanisms exist for the passage of various compounds across the plasma membrane, including passive diffusion, facilitated diffusion, and active transport systems. Passive diffusion of proteins through the bilayer lipid structure of the plasma membrane is a function of the size, lipid solubility, and charge of the protein molecule. A further uptake mechanism is endocytosis. Endocytosis is a process whereby cells absorb material from the outside by engulfing it with their cell membrane. Endocytosis works with macromolecules or particulate matter beyond a certain size threshold and also with fluids (pinocytosis). Correspondingly, the test compound should be contacted with the subject in a way that allows for the interaction of the test compound with cells that are part of the sample to be subsequently obtained from said subject and assessed in accordance with the method of the invention. For example, if blood is intended to be obtained as sample from the subject, intravenous administration of the test compound—if necessary as part of a therapeutically acceptable composition—will be suitable to allow for an interaction of cells of the sample with the test compound. Accordingly, said test compound may be, e.g., added to the culture medium or injected into a cell or administered to an individual prior to the assessment of the expression level in step (a). Moreover, the compound to be identified can be contained in libraries of small molecules, such as organic or inorganic small molecules which may be commercially available. In addition, libraries comprising antibodies or functional fragments or derivatives thereof (i.e. fragments or derivatives maintaining the binding specificity of the original antibody) may be used as a starting point in the identifying process. Suitable libraries are commercially available, for example from ChemBridge Corp., San Diego, USA. Also, libraries of aptamers such as peptide aptamers might be employed. The skilled person is of course free to use any other starting point of desired compounds for use in the method of the invention.

IF a composition containing (a) compound(s) is identified to be capable of preventing or treating PTSD or serving as a lead compound for developing a compound capable of preventing or treating PTSD in the method of the invention, then it is either possible to isolate the active compound(s) from the original composition identified as containing the compound(s) in question or one can further subdivide the original composition, for example, if it consists of a plurality of different test compounds, so as to reduce the number of different substances per sample and repeat the method with the subdivisions of the original composition. It can then be determined whether said subdivided composition or resulting compound displays the desired properties, for example, by the methods described herein or in the literature ("Cells: A laboratory manual", v. 1-3, edited by Spector et al., Cold Spring Harbour Laboratory Press (1997); ISBN 10: 0879695218). Depending on the complexity of the compositions, the steps described above can be performed several times, preferably until the composition identified according to the method of the invention only comprises a limited number of or only one substance(s). Preferably said composition comprises substances of similar chemical and/or physical properties. The method of the present invention can be easily performed and the experimental setup without further ado designed by the person skilled in the art, for example, in accordance with other cell based screening assays described in the prior art. Such adaptation of the method of the invention is well within the skill of the person skilled in the art and can be performed without undue experimentation.

Compounds which can be tested in accordance with the present invention include peptides, proteins, nucleic acids, antibodies, small organic compounds, ligands, peptidomimetics, PNAs and the like. Said compounds may act as agonists or antagonists. Said compounds can also be functional derivatives or analogues of known drugs. Methods for the preparation of chemical derivatives and analogues are well known to those skilled in the art and are described in, for example, Beilstein, Handbook of Organic Chemistry, Springer edition New York Inc., 175 Fifth Avenue, New York, N.Y. 10010 U.S.A. and Organic Synthesis, Wiley, New York, USA. Also, peptide mimetics and/or computer-aided design of appropriate drug derivatives and analogues can be used.

Appropriate computer programs can be used for the identification of interactive sites of a compound putatively capable of preventing and/or treating PTSD by computer assisted searches for complementary structural motifs (Fassina, Immunomethods 5 (1994), 114-120). Further appropriate computer systems for the computer aided design of protein and peptides are described in the prior art, for example, in Berry, Biochem. Soc. Trans. 22 (1994), 1033-1036; Wodak, Ann. N. Y. Acad. Sci. 501 (1987), 1-13; Pabo, Biochemistry 25 (1986), 5987-5991. The results obtained from the above-described computer analysis can be used in combination with the method of the invention for, e.g., optimizing known inhibitors, analogs, antagonists or agonists. Appropriate peptidomimetics can also be identified by the synthesis of peptidomimetic combinatorial libraries through successive chemical modification and testing the resulting compounds, e.g., according to the methods described herein. Methods for the generation and use of peptidomimetic combinatorial libraries are described in the prior art, for example in Ostresh, Methods in Enzymology 267 (1996), 220-234 and Dorner, Bioorg. Med. Chem. 4 (1996), 709-715. Furthermore, the three-dimensional and/or crystallographic structure of said compounds can be used for the design of peptidomimetic drugs (Rose, Biochemistry 35 (1996), 12933-12944; Rutenber, Bioorg. Med. Chem. 4 (1996), 1545-1558). It is very well known how to obtain compounds to be tested in the method of the invention, e.g. by chemical or biochemical standard techniques. Thus, also comprised by the method of the invention are means of making or producing said compounds. In summary, the present invention provides a method for identifying compounds which can be used in specific doses for the prevention or treatment of PTSD.

Also, the method of the invention may be useful in identifying lead compounds. The term "lead compound" in accordance with the present invention refers to a compound discovered by the method of the invention which will be e.g. further optimized, in particular to be pharmaceutically more acceptable. The identified lead compounds may be optimized to arrive at a compound which may be, for example, used in a pharmaceutical composition for preventing or treating PTSD. Methods for the optimization of the pharmacological properties of compounds identified in screens, the lead compounds, are known in the art and comprise a method of modifying a compound identified as a lead compound to achieve: (i) modified site of action, spectrum of activity, organ specificity, and/or (ii) improved potency, and/or (iii) decreased toxicity (improved therapeutic index), and/or (iv) decreased side effects, and/or (v) modified onset of therapeutic action, duration of effect, and/or (vi) modified pharmacokinetic parameters (resorption, distribution, metabolism and excretion), and/or (vii) modified physico-chemical parameters (solubility, hygroscopicity, color, taste, odor, stability, state), and/or (viii) improved general specificity, organ/tissue specificity, and/or (ix) optimized application form and route by (i) esterification of carboxyl groups, or (ii) esterification of hydroxyl groups with carboxylic acids, or (iii) esterification of hydroxyl groups to, e.g. phosphates, pyrophosphates or sulfates or hemi-succinates, or (iv) formation of pharmaceutically acceptable salts, or (v) formation of pharmaceutically acceptable complexes, or (vi) synthesis of pharmacologically active polymers, or (vii) introduction of hydrophilic moieties, or (viii) introduction/exchange of substituents on aromates or side chains, change of substituent pattern, or (ix) modification by introduction of isosteric or bioisosteric moieties, or (x) synthesis of homologous compounds, or (xi) introduction of branched side chains, or (xii) conversion of alkyl substituents to cyclic analogues, or (xiii) derivatisation of hydroxyl group to ketales, acetales, or (xiv) N-acetylation to amides, phenylcarbamates, or (xv) synthesis of Mannich bases, imines, or (xvi) transformation of ketones or aldehydes to Schiff's bases, oximes, acetales, ketales, enolesters, oxazolidines, thiazolidines or combinations thereof.

The various steps recited above are generally known in the art. They include or rely on quantitative structure-activity relationship (QSAR) analyses (Kubinyi (1992) "Hausch-Analysis and Related Approaches", VCH Verlag, Weinheim), combinatorial biochemistry, classical chemistry and others (see, for example, Holzgrabe and Bechtold (2000) Deutsche Apotheker Zeitung 140(8), 813).

The therapeutically useful compounds identified according to the method of the invention can be formulated and administered to a patient by methods well known in the art. Drugs or pro-drugs after their in vivo administration are metabolized in order to be eliminated either by excretion or by metabolism to one or more active or inactive metabolites (Meyer, J. Pharmacokinet. Biopharm. 24 (1996), 449-459). More specifically, a "prodrug" is a compound that is generally not biologically and/or pharmacologically active. After administration, the prodrug is activated, typically in vivo by enzymatic or hydrolytic cleavage and converted to a biologically and/or pharmacologically compound which has the intended medical effect. Prodrugs are typically formed by chemical modification of biologically and/or pharmacologically compounds. Conventional procedures for the selection and preparation of suitable prodrugs are described, for example, in Design of Prodrugs, ed. H. Bundgaard, Elsevier, 1985. Thus, rather than using the actual compound identified in accordance with the method of the present invention a corresponding formulation as a pro-drug can be used which is converted into its active in the patient. Precautionary measures that may be taken for the application of pro-drugs and drugs are described in the literature; see, for review, Ozama, J. Toxicol. Sci. 21 (1996), 323-329.

Preferably, said method is effected in high-throughput format. High-throughput assays, independently of being biochemical, cellular or other assays, generally may be performed in wells of microtiter plates, wherein each plate may contain 96, 384 or 1536 wells. Handling of the plates, including incubation at temperatures other than ambient temperature, and bringing into contact of test compounds with the assay mixture is preferably effected by one or more computer-controlled robotic systems including pipetting devices. In case large libraries of test compounds are to be screened and/or screening is to be effected within short time, mixtures of, for example 10, 20, 30, 40, 50 or 100 test compounds may be added to each well. In case a well exhibits biological activity, said mixture of test compounds may be de-convoluted to identify the one or more test compounds in said mixture giving rise to said activity.

The above definitions apply mutatis mutandis to the methods described in the following.

The method of the invention is based upon the presumption that an increase in expression levels of genes that are identified herein as being associated with the risk of developing PTSD and whose expression is downregulated in PTSD patients is suitable to prevent the onset of or to treat acute PTSD in a subject. The increase in expression levels is determined vis-à-vis the expression levels of a control sample or cell in step (b). Step (b) serving as control, it is self-evident that the control samples of step (b) i), ii) or iii) are not to be contacted with the test compound referred to in step (a). Said control sample or cell may be a sample or cell that has not been contacted with the compound to be tested. Additionally or alternatively the expression levels of the sample or cell may be compared to the expression levels of a sample or cell that has been contacted with a compound known to not affect the expression levels of the target genes. It is also envisaged that in addition to the comparison of the expression levels of the cells or the sample of step (a) against the one or both latter negative controls a comparison against a sample or cell contacted with a compound known to increase the expression level of the genes is effected. A corresponding method provides a qualitative assessment of the compound to be tested. It is alternatively possible to exclusively compare expression levels of the cell or sample of step (a) against the expression levels of a cell or sample that has been contacted with a compound known to increase the expression of the target genes, if it is desired to screen for compounds that have a similar or superior effect on the expression levels as the latter control. A corresponding experimental setup would hence allow identifying compounds that are similar or superior to existing compounds that are capable of increasing the expression levels of the target genes. In other words, corresponding compounds may be capable of effecting an essentially equal increase of the expression level or an higher increase of the expression levels as compared to the compound known to enhance the expression level of the target gene(s). The term “essentially equal” refers to an expression level that is at least 90% such as at least 91%, 92%, 93%, 94%, 95%, or preferably at least 96% or 97%, more preferred 98% or 99% and most preferred at least 100% as high as the expression level of the target gene(s) of the cell or sample that has been contacted with the compound known to enhance the expression level of said gene(s). Also, the expression level could be greater than 100% such as, e.g., at least 101%, 102%, 103%, 104%, 105%, or preferably at least 106% or 107%, more preferred at least 110% or 120% and most preferred at least 200% or more. Depending on the potency of the compound known to increase the expression level of the target genes, it may not be possible to further increase the expression levels and accordingly, suitable compounds to be identified by the method of the invention may in comparison only achieve a fraction of the increase in expression of the positive control. Hence, compounds that only result in expression level of the target gene(s) of at least 5% such as at least 10%, 20%, 30%, 40%, 50%, or preferably at least 60% or 70% and most preferred at least 80% or at least 89% as high as the expression level of the target gene(s) of the cell or sample that has been contacted with the compound known to enhance the expression level of said gene(s) can also be identified in accordance with the method of the invention. Accordingly, the identification of compounds that are capable of adjusting the expression level of the risk gene(s) as described herein towards the expression level of the corresponding gene(s) in a person not at risk for PTSD, preferably selectively and in a dose-dependent fashion, provides the means for a drug-based therapeutic intervention. The above applies mutatis mutandis to other embodiments recited herein.

In a preferred embodiment, the method of the invention further comprises synthesizing said compound being capable of preventing or treating PTSD or serving as a lead compound for developing a compound capable of preventing or treating PTSD.

As outlined above, it is well-known in the art how to obtain, produce and modulate the test compounds, e.g. by chemical or biochemical standard techniques. Thus, having identified a compound that is capable of preventing or treating PTSD or serving as a lead compound for developing a compound capable of preventing or treating PTSD the skilled person is in the position by employing said chemical or biochemical standard techniques to synthesize said identified compound in desired amounts.

In another preferred embodiment of the method of the invention, the method further comprises in step (a) additionally assessing the expression level of one or both further genes selected from MAN2C1 or DDX17 in a cell contacted with a test compound or in a sample obtained from a subject and contacted with said test compound; and in step (b) additionally assessing the expression level of MAN2C1 or DDX17 in a cell or a sample obtained from a subject, wherein said cell or sample was i) not contacted with the test compound; ii) contacted with a compound known to not affect the expression levels of MAN2C1 or DDX17 of step (a), wherein a decrease of the expression level of MAN2C1 or DDX17 in step (a) as compared to step (b) i) or (b) ii) is indicative of said test compound being capable or preventing or treating PTSD or serving as a lead compound for developing a compound capable of preventing or treating PTSD; or iii) contacted with a compound known to enhance the expression level of MAN2C1 or DDX17 of step (a), wherein an essentially equal level of expression or a decrease of the expression level of MAN2C1 or DDX17 in step (a) as compared to step (b) iii) is indicative of the compound being capable of preventing or treating PTSD or serving as a lead compound for developing a compound capable of preventing or treating PTSD.

In a different preferred embodiment of the method of the invention, the method further comprises in step (a) additionally assessing the expression level of one or more further genes selected from CPNE1, TSC1, ADAM17, RNF181, MYO1C, MOBKL1B, GBA, C2orf34, TMEM167A, MAST4, ASAH1, CGGBP1, FAM175B, BIN1, KLF12, METTL7A, TMEM49, RPS6KA5 and DR HLA-DRB1 in a cell contacted with a test compound or in a sample obtained from a subject and contacted with said test compound; and in step (b) additionally assessing the expression level of said one or more further genes selected from CPNE1, TSC1, ADAM17, RNF181, MYO1C, MOBKL1B, GBA, C2orf34, TMEM167A, MAST4, ASAH1, CGGBP1, FAM175B, BIN1, KLF12, METTL7A, TMEM49, RPS6KA5 and DR HLA-DRB1 in a cell or a sample obtained from a subject, wherein said cell or sample was i) not contacted with the test compound; ii) contacted with a compound known to not affect the expression levels of said one or more further genes selected from CPNE1, TSC1, ADAM17, RNF181, MYO1C, MOBKL1B, GBA, C2orf34, TMEM167A, MAST4, ASAH1, CGGBP1, FAM175B, BIN1, KLF12, METTL7A, TMEM49, RPS6KA5 and DR HLA-DRB1 of step (a), wherein an increase of the expression level of said one or more further genes selected from CPNE1, TSC1, ADAM17, RNF181, MYO1C, MOBKL1B, GBA, C2orf34, TMEM167A, MAST4, ASAH1, CGGBP1, FAM175B, BIN1, KLF12, METTL7A, TMEM49, RPS6KA5 and DR HLA-DRB1 in step (a) as compared to step (b) i) or (b) ii) is indicative of said test compound being capable or preventing or treating PTSD or serving as a lead compound for developing a compound capable of preventing or treating PTSD; or iii) contacted with a compound known to enhance the expression level of said one or more further genes selected from CPNE1, TSC1, ADAM17, RNF181, MYO1C, MOBKL1B, GBA, C2orf34, TMEM167A, MAST4, ASAH1, CGGBP1, FAM175B, BIN1, KLF12, METTL7A, TMEM49, RPS6KA5 and DR HLA-DRB1 of step (a), wherein an essentially equal level of expression or an increase of the expression level of said one or more further genes selected from CPNE1, TSC1, ADAM17, RNF181, MYO1C, MOBKL1B, GBA, C2orf34, TMEM167A, MAST4, ASAH1, CGGBP1, FAM175B, BIN1, KLF12, METTL7A, TMEM49, RPS6KA5 and DR HLA-DRB1 in step (a) as compared to step (b) iii) is indicative of the compound being capable of preventing or treating PTSD or serving as a lead compound for developing a compound capable of preventing or treating PTSD.

In step (b) ii) it is envisaged that a compound be used for contacting that is known not to affect the expression level(s) of any one of the additional gene(s) to be assessed in step (a). For example, if the expression level of KLF12 is additionally assessed, then the cell or sample of step (b) ii) was not contacted with a compound affecting expression of KLF12. The same applies mutatis mutandis to other embodiments herein.

As outlined supra, each of the recited genes is linked to the risk to develop PTSD also when assessed on its own, hence identifying a compound that alters the expression level of only one of said genes may be a suitable drug candidate.

In this embodiment, advantageously one or more of the above-recited genes is additionally assessed in order to identify a compound that alters the expression level of, e.g., more than one gene associated with the risk to develop PTSD or of one of said other (additional) gene(s) associated with the risk to develop PTSD, hence being a compound potentially more potent in preventing or treating PTSD or a more promising lead compound for developing a compound capable of preventing or treating PTSD.

In another preferred embodiment of the method of the invention, the method further comprises in step (a) additionally assessing the expression level of MAN2C1 in a cell contacted with a test compound or in a sample obtained from a subject and contacted with said test compound; and in step (b) additionally assessing the expression level of MAN2C1 in a cell or a sample obtained from a subject, wherein said cell or sample was i) not contacted with the test compound; ii) contacted with a compound known to not affect the expression levels of MAN2C1 of step (a), wherein a decrease of the expression level of MAN2C1 in step (a) as compared to step (b) i) or (b) ii) is indicative of said test compound being capable or preventing or treating PTSD or serving as a lead compound for developing a compound capable of preventing or treating PTSD; or iii) contacted with a compound known to decrease the expression level of MAN2C1 of step (a), wherein an essentially equal level of expression or a decrease of the expression level of MAN2C1 in step (a) as compared to step (b) iii) is indicative of the compound being capable of preventing or treating PTSD or serving as a lead compound for developing a compound capable of preventing or treating PTSD.

In a different preferred embodiment of the method of the invention, the method further comprises in step (a) additionally assessing the expression level of one or more further genes selected from CPNE1, ADAM17, and METTL7A in a cell contacted with a test compound or in a sample obtained from a subject and contacted with said test compound; and in step (b) additionally assessing the expression level of said one or more further genes selected from CPNE1, ADAM17, and METTL7A in a cell or a sample obtained from a subject, wherein said cell or sample was i) not contacted with the test compound; ii) contacted with a compound known to not affect the expression levels of said one or more further genes selected from CPNE1, ADAM17 and METTL7A of step (a), wherein an increase of the expression level of said one or more further genes selected from CPNE1, ADAM17 and METTL7A in step (a) as compared to step (b) i) or (b) ii) is indicative of said test compound being capable or preventing or treating PTSD or serving as a lead compound for developing a compound capable of preventing or treating PTSD; or iii) contacted with a compound known to enhance the expression level of said one or more further genes selected from CPNE1, ADAM17 and METTL7A of step (a), wherein an essentially equal level of expression or an increase of the expression level of said one or more further genes selected from CPNE1, ADAM17 and METTL7A in step (a) as compared to step (b) iii) is indicative of the compound being capable of preventing or treating PTSD or serving as a lead compound for developing a compound capable of preventing or treating PTSD.

Based on the foregoing, it is especially advantageous to identify compounds that are capable of adjusting the expression levels of MAN2C1, CPNE1, ADAM17 and METTL7A, i.e. decreasing the expression level of MAN2C1 and increasing the expression levels of CPNE1, ADAM17 and/or METTL7A, to a normal level when compared to controls as this may on the one hand prevent PTSD or on the other hand in a treatment regimen at least reduce the severity of symptoms in particularly severely affected PTSD patients. These results underscore the relevance of risk factors in association with gene expression in predicting PTSD severity, which may lead to new effective personalized treatment approaches, considering both genotype and biomarkers (Holsboer F. Challenges and opportunities for the development of personalized antidepressant medicines. *Nat Rev Neurosci*, in press 2008).

In a preferred embodiment of the method of the invention, the expression level of at least two of the genes selected from the FKBP5 gene, STAT5B gene and NFIA gene is assessed.

In order to increase the predictive power and reliability of the method of the invention the expression levels of at least two of the genes associated with PTSD are assessed. Accordingly, in a more preferred embodiment of the method, the expression levels of the FKBP5 gene and the STAT5B gene are assessed. Also preferred and in accordance with the foregoing is the assessment of the expression level of the FKBP5 gene and the NFIA gene or the STAT5B gene and the NFIA gene. Most preferred is that the expression level of all three genes is assessed.

In a preferred embodiment of the method of the invention, the sample is selected from blood, saliva and buccal smear.

A preferred sample to be used in the method of the invention is blood (cf. also supra) due to the ease of accessibility and clinical routine of blood collection as well as the standardized protocols to extract and purify nucleic acids and/or proteins from blood constituents. Preferred in accordance with the method of the invention are peripheral blood mononuclear cells as blood constituent that is to be further processed for extraction of nucleic acids and/or proteins. Suitable methods for extraction and purification of nucleic acids and/or proteins form blood are well-known to the person skilled in the art and have been described herein above. Also preferred as sample in accordance with the method of the invention are saliva and buccal smear samples that are equally conveniently accessible for collection, however, without having to injure a subject in order to get to the sample as compared to blood collection. Preferred are buccal mucosa epithelial cells that can be isolated from buccal swabs for further processing to extract and purify nucleic acids and/or proteins in order to determine expression levels of genes associated with the risk to develop PTSD.

In a further preferred embodiment of the method of the invention, said test compound is selected from a small molecule, an antisense nucleic acid molecule, a siRNA, a shRNA, a miRNA, a ribozyme, a peptide aptamer, a nucleic acid based aptamer, an antibody or a combination thereof.

The term "small chemical molecule" as used herein may describe, for example, a small organic molecule. Organic molecules relate or belong to the class of chemical compounds having a carbon basis, the carbon atoms linked together by carbon-carbon bonds. The original definition of the term organic related to the source of chemical compounds, with organic compounds being those carbon-containing compounds obtained from plant or animal or microbial sources, whereas inorganic compounds were obtained from mineral sources. Organic compounds can be natural or synthetic. Alternatively the compound may be an inorganic compound. Inorganic compounds are derived from mineral sources and include all compounds without carbon atoms (except carbon dioxide, carbon monoxide and carbonates). Preferably, the small molecule has a molecular weight of less than about 2000 amu, or less than about 1000 amu such as 500 amu, and even less than about 250 amu. The size of a small molecule can be determined by methods well-known in the art, e.g., mass spectrometry. Small molecules may be designed, for example, in silico based on the crystal structure of potential drug targets, where sites presumably responsible for the biological activity and involved in the regulation of expression of genes identified herein, can be identified and verified in in vivo assays such as in vivo HTS (high-throughput screening) assays.

The term "antisense nucleic acid molecule" is known in the art and refers to a nucleic acid which is complementary to a target nucleic acid. An antisense molecule according to the invention is capable of interacting with, more specifically hybridizing with the target nucleic acid. By formation of the hybrid, transcription of the target gene(s) and/or translation of the target mRNA is reduced or blocked. Preferably, the nucleic acid molecule is a antisense RNA molecule. Standard methods relating to antisense technology have been described (see, e.g., Melani et al., Cancer Res. (1991) 51:2897-2901).

For therapeutic uses, the RNA inactivation by antisense molecules or by ribozymes (cf. infra) appears to be implementable. Both classes of compounds can be synthesized chemically or produced in conjunction with a promoter by biological expression in vitro or even in vivo.

Small interfering RNAs (siRNA), sometimes known as short interfering RNAs or silencing RNAs, are a class of 18 to 30, preferably 20 to 25, most preferred 21 to 23 or 21 nucleotide-long double-stranded RNA molecules that play a variety of roles in biology. Most notably, siRNA is involved in the RNA interference (RNAi) pathway where the siRNA interferes with the expression of a specific gene. In addition to their role in the RNAi pathway, siRNAs also act in RNAi-related pathways, e.g. as an antiviral mechanism or in shaping the chromatin structure of a genome.

Said siRNA molecule or a metabolic processing product thereof is capable of mediating target-specific nucleic acid modifications, particularly RNA interference and/or DNA methylation. Preferably at least one RNA strand has a 5'- and/or 3'-overhang. Preferably, one end of the double-strand has a 3'-overhang from 1-5 nucleotides, more preferably from 1-3 nucleotides and most preferably 2 nucleotides. The other end may be blunt-ended or has up to 6 nucleotides 3'-overhang. In general, any RNA molecule suitable to act as siRNA is envisioned in the present invention.

Preferred siRNAs have a well defined structure: a short double-strand of RNA (dsRNA) with 2-nt 3' overhangs on either end. Each strand has a 5' phosphate group and a 3' hydroxyl (—OH) group. As regards naturally occurring siRNAs, this structure is the result of processing by dicer, an enzyme that converts either long dsRNAs or small hairpin RNAs into siRNAs. SiRNAs can also be exogenously (artificially) introduced into cells to bring about the specific knockdown of a gene of interest. Essentially any gene of which the sequence is known can thus be targeted based on sequence complementarity with an appropriately tailored siRNA.

The most efficient silencing was so far obtained with siRNA duplexes composed of 21-nt sense and 21-nt antisense strands, paired in a manner to have a 2-nt 3'-overhang. The sequence of the 2-nt 3' overhang makes a small contribution to the specificity of target recognition restricted to the unpaired nucleotide adjacent to the first base pair (Elbashir et al., EMBO J 2001, 20(23):6877-6888). 2'-deoxynucleotides in the 3' overhangs are as efficient as ribonucleotides, but are often cheaper to synthesize and probably more nuclease resistant.

A short hairpin RNA (shRNA) is a sequence of RNA that makes a tight hairpin turn that can be used to silence gene expression via RNA interference. shRNA uses a vector introduced into cells and utilizes the U6 promoter to ensure that the shRNA is always expressed. This vector is usually passed on to daughter cells, allowing the gene silencing to be inherited. The shRNA hairpin structure is cleaved by the cellular machinery into siRNA, which is then bound to the RNA-induced silencing complex (RISC). This complex binds to and cleaves mRNAs which match the siRNA that is bound to it.

Si/shRNAs to be used in the method of the present invention are preferably chemically synthesized using appropriately protected ribonucleoside phosphoramidites and a conventional DNA/RNA synthesizer. Suppliers of RNA synthesis reagents are Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA), and Cruachem (Glasgow, UK). Most conveniently, siRNAs are obtained from commercial RNA oligo synthesis suppliers, which sell RNA-synthesis products of different quality and costs. In general, the RNAs applicable in the present invention are conventionally synthesized and are readily provided in a quality suitable for RNAi.

Further molecules effecting RNAi include, for example, microRNAs (miRNA). Said RNA species are single-stranded RNA molecules which as endogenous RNA molecules regulate gene expression. Upon binding to a complementary mRNA transcript triggers the degradation of said mRNA transcript through a process similar to RNA interference. Accordingly, miRNAs may be employed to directly or indirectly regulate the expression of genes associated with PTSD.

A "ribozyme" (from ribonucleic acid enzyme, also called RNA enzyme or catalytic RNA) is an RNA molecule that catalyzes a variety of reactions. Many natural ribozymes catalyze either their own cleavage or the cleavage of other RNAs, but they have also been found to catalyze the aminotransferase activity of the ribosome.

Examples of well-characterized small self-cleaving RNAs are the hammerhead, hairpin, hepatitis delta virus, and in vitro-selected lead-dependent ribozymes. The organization of these small catalysts is contrasted to that of larger ribozymes, such as the group I intron.

The principle of catalytic self-cleavage has become well established in the last 10 years. The hammerhead ribozymes are characterized best among the RNA molecules with ribozyme activity. Since it was shown that hammerhead structures can be integrated into heterologous RNA sequences and that ribozyme activity can thereby be transferred to these molecules, it appears that catalytic antisense sequences for almost any target sequence can be created, provided the target sequence contains a potential matching cleavage site.

The basic principle of constructing hammerhead ribozymes is as follows: An interesting region of the RNA, which contains the GUC (or CUC) triplet, is selected. Two oligonucleotide strands, each with 6 to 8 nucleotides, are taken and the catalytic hammerhead sequence is inserted between them. Molecules of this type were synthesized for numerous target sequences. They showed catalytic activity in vitro and in some cases also in vivo. The best results are usually obtained with short ribozymes and target sequences.

Aptamers are oligonucleic acid or peptide molecules that bind a specific target molecule. Aptamers are usually created by selecting them from a large random sequence pool, but natural aptamers also exist in riboswitches. Aptamers can be used for both basic research and clinical purposes as macromolecular drugs. Further, they can be combined with ribozymes to self-cleave in the presence of their target molecule.

More specifically, aptamers can be classified as DNA or RNA aptamers or peptide aptamers. Whereas the former consist of (usually short) strands of oligonucleotides, the latter consist of a short variable peptide domain, attached at both ends to a protein scaffold. Nucleic acid aptamers are nucleic acid species that may be engineered through repeated rounds of in vitro selection or equivalently, SELEX (systematic evolution of ligands by exponential enrichment) to bind to various molecular targets such as small molecules, proteins, nucleic acids, and even cells, tissues and organisms.

Peptide aptamers are proteins that are designed to interfere with other protein interactions inside cells. They consist of a variable peptide loop attached at both ends to a protein scaffold. This double structural constraint greatly increases the binding affinity of the peptide aptamer to levels comparable to an antibody's (nanomolar range). The variable loop length is typically comprised of 10 to 20 amino acids, and the scaffold may be any protein which have good solubility properties. Currently, the bacterial protein Thioredoxin-A is the most used scaffold protein, the variable loop being inserted within the reducing active site, which is a -Cys-Gly-Pro-Cys- loop in the wild protein, the two cysteins lateral chains being able to form a disulfide bridge. Peptide aptamer selection can be made using different systems, but the most used is currently the yeast two-hybrid system.

Aptamers offer the utility for biotechnological and therapeutic applications as they offer molecular recognition properties that rival those of the commonly used biomolecules, in particular antibodies. In addition to their discriminate recognition, aptamers offer advantages over antibodies as they can be engineered completely in a test tube, are readily produced by chemical synthesis, possess desirable storage properties, and elicit little or no immunogenicity in therapeutic applications.

Non-modified aptamers are cleared rapidly from the bloodstream, with a half-life of minutes to hours, mainly due to nuclease degradation and clearance from the body by the kidneys, a result of the aptamer's inherently low molecular weight. Unmodified aptamer applications currently focus on treating transient conditions such as blood clotting, or treating organs such as the eye where local delivery is possible. This rapid clearance can be an advantage in applications such as in vivo diagnostic imaging. Several modifications, such as 2'-fluorine-substituted pyrimidines, polyethylene glycol (PEG) linkage, etc. are available to scientists with which the half-life of aptamers easily can be increased to the day or even week time scale.

A recent development is the combination of an aptamer recognizing a small compound with a hammerhead ribozyme. The conformational change induced in the aptamer upon binding the target molecule, is supposed to regulate the catalytic function of the ribozyme.

The term "antibody" as used herein can be, for example, relate to polyclonal or monoclonal antibodies. The term "antibody" also comprises derivatives or fragments thereof with retained binding specificity. Techniques for the production of antibodies are well known in the art and described, e.g. in Harlow and Lane "Antibodies, A Laboratory Manual", Cold Spring Harbor Laboratory Press, 1988 and Harlow and Lane "Using Antibodies: A Laboratory Manual" Cold Spring Harbor Laboratory Press, 1999. The antibodies can be used in accordance with the method of the invention to interfere with the regulation of expression of any gene associated with a risk to develop PTSD described herein. Also, antibodies may be useful, for example, for immunoprecipitation, affinity purification and immunolocalization of the gene products, i.e. the proteins, of the genes associated with a risk to develop PTSD as well as for the monitoring of the presence and amount of such proteins, for example, in cultures of eukaryotic cells or organisms.

An antibody to be used in accordance with the invention also includes embodiments such as chimeric (human constant domain, non-human variable domain), single chain and humanized (human antibody with the exception of non-human CDRs) antibodies, as well as antibody fragments, like, inter alia, Fab or Fab' fragments. Antibody fragments or derivatives further comprise Fd, $F(ab')_2$, Fv or scFv fragments; see, for example, Harlow and Lane (1988) and (1999), loc. cit. Various procedures are known in the art and may be used for the production of such antibodies and/or fragments. For example, the (antibody) derivatives can be produced by peptidomimetics. Further, techniques described for the production of single chain antibodies (see, inter alia, U.S. Pat. No. 4,946,778) can be adapted to produce single chain antibodies specific for any target epitope/s. Also, transgenic animals or plants (see, e.g., U.S. Pat. No. 6,080,560) may be used to express (humanized) antibodies specific for any target epitope/s. For the preparation of monoclonal antibodies, any technique which provides antibodies produced by continuous cell line cultures can be used. Examples for such techniques include the hybridoma technique (Köhler and Milstein, Nature 256 (1975), 495-497), the trioma technique, the human B-cell hybridoma technique (Kozbor, Immunology Today 4 (1983), 72) and the EBV-hybridoma technique to produce human monoclonal antibodies (Cole et al., Monoclonal Antibodies and Cancer Therapy, Alan R. Liss, Inc. (1985), 77-96). Surface plasmon resonance as employed in the BIAcore system can be used to increase the efficiency of phage antibodies which bind to an epitope of an polypeptide of the invention (Schier, Human Antibodies Hybridomas 7 (1996), 97-105; Malmborg, J. Immunol. Methods 183 (1995), 7-13). It is also envisaged in the context of this invention that the term "antibody" comprises antibody constructs which may be expressed in cells, e.g. antibody constructs which may be transfected and/or transduced via, amongst others, viruses or plasmid vectors.

The antibody to be used in the method of the invention is capable to specifically bind/interact with a target epitope. The term "specifically binding/interacting with" as used in accordance with the present invention means that the antibody does not or essentially does not cross-react with an epitope of similar structure. Cross-reactivity of a panel of antibodies under investigation may be tested, for example, by assessing binding of said panel of antibodies under conventional conditions to the epitope of interest as well as to a number of more or less (structurally and/or functionally) closely related epitopes. Only those antibodies that bind to the epitope of interest in its relevant context (e.g. a specific motif in the structure of a protein) but do not or do not essentially bind to any of the other epitope are considered specific for the epitope of interest and thus to be antibodies in accordance with this invention. Corresponding methods are described e.g. in Harlow and Lane, 1988 and 1999, loc cit.

With regard to genes whose expression levels are upregulated when indicative for a risk to develop PTSD it is possible to decrease expression levels by using, e.g., the above described antisense nucleic acid molecule, the RNA molecules or antibodies. Said compounds may be designed by methods well-known in the art to interact target-specifically with either mRNA or protein molecules and thereby reduce the expression level. For example, RNA molecules suitable for RNA interference can be designed leading to a reduction of mRNA molecules and hence of the expression level of the target gene(s). However, it may also be possible to indirectly reduce the expression level of said gene(s) by using any of the above-mentioned compounds by reducing and/or inhibiting, e.g., protein or mRNA molecules that are involved in the regulation of expression of said target gene(s). Also target gene(s) whose expression is decreased when indicative for a risk to develop PTSD may directly or indirectly be targeted by the above compounds resulting in an increase of expression levels. For example, said target gene(s) may be targeted indirectly by increasing the amount of protein or mRNA molecules that are involved in the regulation of expression of said gene(s) such as, e.g., transcription factors or transcription enhancing factors.

In preferred embodiments of the method of the invention, the expression level is assessed on the transcriptional level or on the translational level.

As previously outlined herein supra, the expression of a gene is a process that can be subdivided into two distinct processes characterised by their end products. Without wishing to be bound by a specific scientific theory but to provide a simplistic view of a complicated process, the process of transcription can be said to result in the generation of mRNA, which in the second process, i.e. translation, is used as a starting point for the production of a peptide or protein. Accordingly, it is possible to determine the expression level of a gene not only on the transcriptional level, but also on the translational level. Nevertheless, a variety of methods have been developed and successfully employed to determine translational gene activity, which are well-known in the art (cf., e.g., Kingsmore S F, Nat Rev Drug Discovery 2006; 5: 310-20; Turck C W et al (in press), Proteomic strategies for biomarker discovery—from differential expression to isoforms to pathways. In: Turck C W (ed) Biomarkers for psychiatric disorders. Springer, Berlin Heidelberg New York.), all of which generally can be employed in accordance with the invention.

In a more preferred embodiment, the expression on the transcriptional level is assessed using Northern blotting, reverse transcriptase polymerase chain reaction-based methods, microarray or tag-based methods.

"Northern blotting" is a technique used to study gene expression and is based upon the electrophoretic separation on either agarose or denaturing polyacrylamide gels, wherein the latter gels are preferentially used for smaller fragments of RNA, and the subsequent detection of the target RNA with a hybridisation probe. The probe may be made from DNA or RNA. Also, a "reverse Northern blot" may be performed in order to assess gene expression levels. In this assay, the substrate nucleic acid which is affixed to a membrane is a collection of isolated DNA fragments and the probe is RNA extracted from a sample and e.g. radioactively labeled. The basic principle and technique of Northern blotting is well-known in the art and the skilled person knows how to adapt said technique to his specific experimental needs, particularly how to design suitable probes.

DNA microarrays are devices for high-throughput assays used to simultaneously assay a variety of target genes and capture the status quo of a sample with respect to, e.g., gene expression or genotype. The use of microarrays has dramatically increased in the last 10 years and the use as well as the design of microarray studies can be considered common general knowledge in the technical field of the invention, i.e. medical genetics. Generally, it consists of an arrayed series of a specified number of microscopic spots, also called features, where DNA oligonucleotides are immobilized each containing picomoles of a specific DNA sequence. This can be a short section of a gene or other DNA element that are used as probes to hybridize a cDNA or cRNA sample (called target) under high-stringency conditions. Probe-target hybridization is usually detected and quantified by fluorescence-based detection of fluorophore-labeled targets to determine relative abundance of nucleic acid sequences in the target.

In standard microarrays, the probes may be attached to a solid surface by a covalent bond to a chemical matrix (via epoxy-silane, amino-silane, lysine, polyacrylamide or others). The solid surface can be glass or a silicon chip, in which case they are commonly known as gene chip or colloquially "Affy chip" when an Affymetrix chip is used. Other microarray platforms, such as Illumina, use microscopic beads, instead of a large solid support. DNA arrays are different from other types of microarray only in that they either measure DNA or use DNA as part of its detection system.

DNA microarrays can be used to measure changes in expression levels of the genes associated with a risk to develop PTSD in accordance with the method of the invention. Factors to be considered when conducting microarray experiments are the experimental design and the methods of analyzing the data, which are mostly effected using computer-aided analyzing programs, all of which belong to the common general knowledge in the technical field of the invention (cf. e.g., Bakay M et al., *BMC Bioinformatics* 2002, 3: 4; Gentleman R et al. (2005). Bioinformatics and computational biology solutions using R and bioconductor. Springer: New York; Heber S. & Sick B., *Omics* 2006; 10: 358-68).

The reverse transcriptase polymerase chain reaction-based methods to be used in accordance with the method of the invention are based on the principle of initially converting in a first step RNA obtained from a sample into DNA. Briefly, an mRNA template, dNTPs and reverse transcriptase are combined with a DNA primer in a reverse transcriptase buffer to produce complementary DNA (cDNA). In a second step, the generated cDNA is subjected to PCR that amplifies the target cDNA. The resulting DNA amplicons may be employed in further assays such as, e.g., a Northern blot. A preferred reverse transcriptase polymerase chain reaction-based method is the so called (quantitative) real-time PCR which is used to simultaneously amplify and quantify a target DNA molecule. The general principles of PCR as well as the numerous established variations based on said principle are well-known in the art and described in a variety of textbooks as well as scientific articles (cf., e.g., Saiki R K et al., Science 1988; 239: 487-91; Mullis K B et al. (1994). PCR: Polymerase Chain Reaction. Birkhauser: Boston). Briefly, PCR is performed on an automated cycler device, which can heat and cool containers with the reaction mixture in a very short time. The PCR, generally, consists of many repetitions of a cycle which consists of: (a) a denaturing step, which melts both strands of a DNA molecule and terminates all previous enzymatic reactions; (b) an annealing step, which is aimed at allowing the primers to anneal specifically to the melted strands of the DNA molecule; and (c) an extension step, which elongates the annealed primers by using the information provided by the template strand. Generally, PCR can be performed for example in a 50 μl reaction mixture containing 5 μl of 10×PCR buffer with 1.5 mM $MgCl_2$, 200 μM of each deoxynucleoside triphosphate, 0.5 μl of each primer (10 μM), about 10 to 100 ng of template DNA and 1 to 2.5 units of Taq Polymerase. The primers for the amplification may be labeled or be unlabeled. DNA amplification can be performed, e.g., with a model 2400 thermal cycler (Applied Biosystems, Foster City, Calif.): 2 min at 94° C., followed by 30 to 40 cycles consisting of annealing (e. g. 30 s at 50° C.), extension (e. g. 1 min at 72° C., depending on the length of DNA template and the enzyme used), denaturing (e. g. 10 s at 94° C.) and a final annealing step at 55° C. for 1 min as well as a final extension step at 72° C. for 5 min. Suitable polymerases for use with a DNA template include, for example, *E. coli* DNA polymerase I or its Klenow fragment, T4 DNA polymerase, Tth polymerase, Taq polymerase, a heat-stable DNA polymerase isolated from *Thermus aquaticus* Vent, Amplitaq, Pfu and KOD, some of which may exhibit proof-reading function and/or different temperature optima. The person skilled in the art knows how to optimize PCR conditions for the amplification of specific nucleic acid molecules with primers of different length and/or composition or to scale down or increase the volume of the reaction mix.

The exponential amplification via reverse transcription polymerase chain reaction provides for a highly sensitive technique, where a very low copy number of RNA molecules can be detected. Reverse transcription polymerase chain reaction is widely used in the diagnosis of genetic diseases—applied to the method of the invention for the semiquantitative determination of the abundance of specific different RNA molecules within a cell or tissue as a measure of gene expression.

Tag-based methods refer to methods relying on the extraction of a short sequence (tag) that is unique for a specific transcript. These tags are ligated together, cloned and sequenced. The advantage of tag-based methods over microarray methods is their potential to evaluate expression of known as well as unknown genes. The disadvantages are the higher efforts and the qualitative nature of the standard procedure. Most prominent example for tag-based gene expression methods is the Serial Analysis of Gene Expression (SAGE), which is meanwhile a standard method in the science and introduced in many review articles and text books (Velculescu et al., Science 1995; 270: 484-7; Nielsen K L (2008) Serial Analysis of Gene Expression (SAGE); Methods and protocols. Humana Press: Totowa, N.J.).

Further developments of the SAGE technique resulted in so called Digital Gene Expression methods with an improved detection for low-abundance transcripts (Kin et al., Science 2007; 316: 1481-4).

The detection of proteins to determine the expression levels of genes associated with a risk to develop PTSD in accordance with the invention may be performed using a variety of methods suitable to quantify protein amounts.

In a more preferred embodiment of the method of the invention, the expression on the translational level is assayed using antibody arrays or mass spectrometry assays.

Antibody arrays facilitate the simultaneous detection of multiple proteins and can be designed as antibody microarrays to allow for a high-throughput setup. For example, antibodies directed to the proteins of the genes associated with a risk to develop PTSD may be arranged to form an antibody array that can be used as a test system in a clinical setting as well as private practice for the diagnosis of a risk to develop PTSD.

Mass spectrometry is an analytical technique that identifies the chemical composition of a compound or sample on the basis of the mass-to-charge ratio of charged particles. The method employs chemical fragmentation of a sample into charged particles (ions) and measurements of two properties, charge and mass, of the resulting particles, the ratio of which is deduced by passing the particles through electric and magnetic fields in a mass spectrometer. The design of a mass spectrometer has three essential modules: an ion source, which transforms the molecules in a sample into ionized fragments; a mass analyzer, which sorts the ions by their masses by applying electric and magnetic fields; and a detector, which measures the value of some indicator quantity and thus provides data for calculating the abundances each ion fragment present. Besides allowing a quantitative analysis of a sample in accordance with the method of the invention, the technique also other uses, such as identifying unknown compounds, determining the isotopic composition of elements in a compound, determining the structure of a compound by observing its fragmentation, studying the fundamentals of gas phase ion chemistry (the chemistry of ions and neutrals in vacuum), and determining other physical, chemical, or biological properties of compounds. Mass spectrometry assays for quantitative analysis of samples described herein are well-known in the art. For example, the Absolute QUAntification (AQUA) mass spectrometry method using stable isotope labelled internal standard peptides is a frequently applied technique to determine precisely quantitative protein expression levels from cell lysates (Kirkpatrick D S et al., Methods 2005; 35: 265-43).

A further embodiment of the invention relates to a method of selecting a therapy to prevent or treat PTSD comprising the steps of: (a) identifying a predisposition for developing post-traumatic stress disorder according to the method of the invention; and (b) selecting a therapy based on the results obtained in the preceding step.

As is evident to the person skilled in the art, the knowledge deduced from the present invention can now be used to exactly and reliably characterize the expression profile of a subject as far as it is relevant in the identification of a predisposition to develop PTSD. Advantageously, PTSD can be predicted or diagnosed and preventive or therapeutical measures can be applied accordingly. Moreover in accordance with the foregoing, in cases where a given therapy proves to be not effective, a suitable individual therapy can be designed based on the knowledge of the individual gene expression profile of a subject with respect to the genes associated with a risk to develop PTSD and new and/or improved therapeutics can be identified, for example, by the method of the invention, and/or developed as has been discussed supra.

A variety of therapies exist to treat PTSD. Generally, physicians choose from psychotherapeutic interventions alone or in combination with psychopharmacological drugs from the type of a selective serotonin reuptake inhibitor (SSRI) or of a benzodiazepine (BZD) for severe forms of the disorder. While psychotherapeutic interventions are costly in terms of money and time, SSRIs and BZD have also impediments, especially with respect to their side-effects. SSRIs can induce a number of medical problems related to the peripheral effects of these drugs. This includes nausea, stomach upset, muscle pain, tachycardia or heart arrhythmia, diminished sexual interest and/or performance, and sleep disturbances. BZD are usually medically well tolerated, but can produce psychomotor side effects and memory disturbances, as well as and foremost can induce tolerance, withdrawal symptoms, and dependence. If an ongoing development of PTSD can be diagnosed prior to the development of full symptoms, the outcome of the disorder would be more favorable (Breslau N. J Clin Psychiatry 2001; 62 Suppl 17: 55-9), especially, as patients with a predominant avoidance behavior, which are less likely to seek medical treatment, are at greater risk to develop a chronic course of the disorders (Perkonigg et al., Am J Psychiatry 2005; 162: 1320-27). As is evident from the above, once diagnosed with a predisposition to develop PTSD a subject may upon exposure to a traumatic event or prior thereto be treated depending on his/her individual genetic make up and accordingly, psychotherapeutic and/or psychopharmacological drugs may be selected by the physician as therapeutical intervention. If the development of severe symptoms can be predicted according to the method of the invention, even a suitable psychopharmacological drug may be selected as therapy such as, e.g. a SSRI, which can be given at a lower dosage than it can be expected for the case of the development of severe symptoms, potentially also saving the subject from side effects.

As outlined above, a reliable method to diagnose a predisposition to develop PTSD has not been available prior to the present invention. Hence, an early diagnosis of a predisposition potentially demands for a different therapy than treating acute PTSD symptoms. Further, depending on the severity of the symptoms it may also be necessary to adjust a therapy accordingly.

In conclusion, due to the invention it is possible to select a suitable therapy such as, e.g., a drug and/or psychotherapy, and a suitable dosage regimen having overall a more beneficial effect than therapeutic approaches without having regard to the individual gene expression profile of the genes associated with a risk to develop PTSD. The effects of therapies, e.g., pharmacologic effects of drugs, can be determined by methods well-known in the art and include, for example, in vitro methods or collecting data relating to disease symptoms in a patient or group of patients.

In accordance with the above, in a preferred embodiment, the method of the invention comprises prior to step (b) a further step (a') of applying and monitoring a therapy.

The step of selecting a therapy may comprise the additional step (a') of applying and monitoring a therapy and based on its outcome select a therapy. For example, subjects that are diagnosed to be at risk for developing PTSD and put on a prophylactic therapy can be monitored and, if necessary, their therapy subsequently be adjusted or changed depending on whether PTSD symptoms occur and to which extent or not. Also, a therapy may be applied to a patient having acute PTSD and routinely the effect of the therapy is monitored and recorded. The recorded data provides the basis for the assessment whether the therapy applied is beneficial to the patient or not. Based on said assessment the person skilled in the art, in this case likely a clinician, will be able to adjust the currently applied therapy, e.g., by increasing/decreasing dosage regimen or dosage amount of the therapy, or decide to completely switch to another therapy.

In accordance with the foregoing, the therapy comprises in another preferred embodiment administration of psychopharmacological medication and/or psychotherapy.

The figures show:

FIG. 1:

Gene activity of FKBP5, STAT5B, and NFIA involved in the fine-regulation of the HPA axis as well as of 21 further genes was profoundly altered in survivors of the New York WTC terrorist attacks who developed PTSD. Effect sizes were beyond the limits of a large effect according to common statistical interpretation guidelines (dashed lines).

The examples illustrate the invention:

EXAMPLE 1

Participants and Clinical Evaluation

A random sample of Caucasians who met criteria for PTSD in at least two out of four waves following 9/11 was invited by mail to participate in this study. After 20 participants were successfully recruited, a random sample of participants who had not met criteria for PTSD at any time were invited to participate, selected to match the PTSD participants in severity of trauma exposure (i.e., high direct vs. low and/or indirect exposure), age, and gender. All participants were Caucasians according to their responses in a self-report questionnaire asking for nationality, first language and ethnicity of the participant and all 4 grandparents. The study was approved by the Mount Sinai School of Medicine and the New York Academy of Medicine. All participants provided written, informed consent, and then further screened to determine eligibility. Participants were not invited to participate further if they had psychotic or bipolar illness, alcohol or substance dependence, or major medical, endocrinological, or neurological illness, confirmed by medical examination. No participant was in active treatment at the time of the study, and none were taking antidepressants.

Diagnostic evaluation at the time of the blood draw (wave 5) was performed by trained psychologists with established interrater reliability on the Clinician Administered PTSD scale (CAPS) (see, Blake et al., *J Trauma Stress* 1995; 8: 75-90) and the Structured Clinical Interview for the DSM-IV (SCID) (see, Spitzer R L, Gibbon M., Williams J B W. *Structured Clinical Interview for DSM-IV Axis* 1 *Disorders* (*SCID*). New York State Psychiatric Institute, Biometrics Research: New York, 1995). These scales, respectively, determined the presence of PTSD and confirmed the absence of other psychiatric disorders. To supplement information already collected in previous waves, information about other lifetime traumatic life events was obtained using the Trauma History Questionnaire (Green B L, Trauma history questionnaire. In Stamm B. (ed) *Measurement of Stress, Trauma, and Adaptation*. Sidran Press: Lutherville, Md., 1996, pp 366-369). Participants also completed the Childhood Trauma Questionnaire (Bernstein et al., *Child Abuse Negl* 2003; 27: 169-190).

EXAMPLE 2

Blood Drawing and Processing

Fasting blood samples were obtained by routine venipuncture between 08:00-09:00 h. Plasma samples were frozen for the subsequent determination of cortisol by radioimmunoassay (RIA). The intra-assay and inter-assay coefficients of variation for this method was 4.0 and 6.8%.

For RNA, blood was processed using the Paxgene RNA stabilization system, which prevents degradation of many short-lived RNA transcripts and prevent further transcription and metabolic activity from altering the composition of the sample.[24] In addition, the samples were subjected to the globin mRNA reduction method as this greatly improves the data quality of stabilized RNA samples hybridized to microarrays. Gene expression studies were carried out using an Affymetrix Human Genome U133 Plus 2.0 Array containing 47 000 transcripts, using standard methods.

Quantitative polymerase chain reaction (qPCR) was performed to validate FKBP5 gene expression. For this procedure, total RNA prepared as above was used to generate cDNA using SuperScript II Reverse Transcriptase (Invitrogen, CA) according to the manufacturer's instructions. Gene expression probes and primers for FKBP5 were designed based on the NCBI sequence (NM_004117.2) using the ProbeFinder v2.41 software (Roche, http://www.universal-probelibrary.com). Four different exon junctions including exon 4 to 5 (4&5), exon 7 to 8 (7&8), exon 8 to 9 (8&9) and exon 11 to 12 (11&12) were quantitatively amplified. qPCR was performed on an ABI Prism™ 7900HT sequence detection system (Applied Biosystems, CA). Each sample was analyzed in quadruplicate in a reaction including 25 ng cDNA, 200 nM of each primer, 100 nM UPL probe, and 1× Platinum Quantitative PCR SuperMix-Uracil-N-Glycosylase (UDG) with ROX (Invitrogen, CA). The values were evaluated using the Sequence Detection Software v2.2.1 (Applied Biosystems, CA).

To test whether the observed FKBP5 expression differences might be partially determined by genotypic variation, we genotyped four single nucleotide polymorphisms (SNPs) in the FKBP5 gene region (rs3800737, rs9296158, rs1360780, rs9470080), which were previously reported as associated with PTSD risk or PTSD related symptoms (Koenen et al., *Mol Psychiatry* 2005; 10: 1058-9; Binder et al., *JAMA* 2008; 299: 1291-305). Genotyping was performed with a Roche LightCycler 480 System using allele-specific hybridization probes obtained from Metabion International AG (Martinsried, Germany); sequences are available upon request. None of the SNPs showed significant deviation from Hardy-Weinberg Equilibrium (p>0.09); genotypes could be determined with a call rate of greater than 97%. Linkage disequilibrium (LD) structure was evaluated with HAPLOVIEW, version 4.0, (http://www.broad.mit.edu/mpg/haploview/) revealing $r^2$ between 0.77 and 0.95, which agrees with previous reports about the LD structure of this gene (Binder et al., *Nat Genet* 2004; 36: 1319-25; Binder et al., *JAMA* 2008; 299: 1291-305).

EXAMPLE 3

Statistical Analysis

Groups were compared on demographic, clinical measures and biological measures using t-tests, or chi-square tests as appropriate.

To analyze the microarray data, RNA expression was compared between cases and controls using dChip 2007 (build date Sep. 5, 2007). Invariant Set Normalization was carried out with all 40 arrays and model-based expression was evaluated using PM-MM probe data. Parameters were chosen using empirically derived false discovery rates (FDR). The use of t-test P-value for identifying differentially expressed genes showed a U-shaped curve in these analyses, with a minimum FDR at P=0.01. Other parameters showed increased FDR with more restrictive filtering. Differentially expressed genes were therefore first identified using P-values of 0.01 or lower as the criterion. As an example, using these parameters and comparing 20 controls and 20 cases with lifetime PTSD led to the identification of genes with an empirical median FDR of 16% and an empirical 90% FDR of 59% (from 200 permutations). Subsequently, the large proportion of these genes where the absolute expression differences were ≤50 were identified as very low-expressing genes and removed from further analyses.

To determine how the above noted gene expression changes might differentiate between persons with and without PTSD, the data were subjected to linear discriminate analysis (LDA), as implemented in dChip.

Data analysis for qPCR was performed using qBase. Reference genes chosen from GAPDH, ACTB, B2M and RPLPO were included based on the minimal coefficient of variation. A normal control sample was run in the each plate as a normalization control set to a value of 1. ANOVA was used to compare the expression levels between PTSD and controls.

Stepwise regression analyses were used to predict the contribution of individual genes to PTSD severity. For genes associated with FKBP5 additional regression analyses were performed to predict the contribution of trauma related variables and plasma cortisol levels to gene expression.

TABLE 1

Gene expression of 24 genes was distinctly altered in survivors of the Sep. 11, 2001, terrorist attacks on the New York World Trade Center, who developed PTSD compared to survivors without PTSD. Among these genes, FKBP5, STAT5B, and NFIA form a network related to the regulatory function of the glucocorticoid receptor, which is the main regulatory element of the primary stress-hormone system.

| Transcript | Fold-change[1] | p |
|---|---|---|
| FKBP5 (transcript a, b) | 0.79/0.78 | <0.0087 |
| STAT5B | 0.77 | 0.0068 |
| NFIA | 0.87 | 0.0058 |
| MAN2C1 | 1.33 | 0.0009 |
| DDX17 | 1.32 | 0.0073 |
| CPNE1 | 0.87 | 0.0081 |
| TSC1 | 0.86 | 0.0080 |
| ADAM17 | 0.85 | 0.0090 |
| RNF181 | 0.84 | 0.0078 |
| MYO1C | 0.84 | 0.0055 |
| MOBKL1B | 0.83 | 0.0071 |
| GBA | 0.81 | 0.0032 |
| C2orf34 | 0.80 | 0.0043 |
| TMEM167A | 0.80 | 0.0099 |
| MAST4 | 0.77 | 0.0027 |
| ASAH1 | 0.77 | 0.0014 |
| CGGBP1 | 0.76 | 0.0055 |
| FAM175B | 0.76 | 0.0059 |
| BIN1 | 0.75 | 0.0024 |
| KLF12 | 0.75 | 0.0027 |
| METTL7A | 0.73 | 0.0068 |
| TMEM49 | 0.71 | 0.0080 |
| RPS6KA5 | 0.71 | 0.0011 |
| DR HLA-DRB1 | 0.24 | 0.0092 |

[1]of gene expression in PTSD compared with trauma exposed controls.

The invention claimed is:

1. A method for diagnosing and treating a human subject with a predisposition to post-traumatic stress disorder (PTSD), comprising:

i) detecting in a blood sample obtained from the human subject a test expression level of FK506 binding protein (FKBP5) gene mRNA;

ii) comparing the test expression level to a mean expression level of FK506 binding protein gene mRNA in control blood samples from a population not predisposed to PTSD and detecting that the test expression level is decreased compared to the mean expression level;

iii) correlating the detected test expression level with the presence of a predisposition to PTSD in the subject; and iv) applying to the subject a therapy to treat or prevent PTSD selected from psychopharmacological medication and/or psychotherapy.

2. The method of claim 1, further comprising detecting in a sample from said subject at least a second test expression level of a mRNA product of a gene selected from the group of genes consisting of: a signal transducer and activator of transcription (STAT5B) gene, a nuclear factor 1A (NF1A) gene, a mannosidase-alpha class 2C, member 1 (MAN2C1) gene; a DEAD box polypeptide 17 (DDX17) gene, a copine I (CPNE1) gene, a tuberous sclerosis 1 (TSC1) gene, an ADAM metallopeptidase domain 17 (ADAM17) gene, a ring finger protein 181 (RNF181) gene, a myosin IC (MYO1C) gene, a Mps One Binder kinase activator-like 1B (MOBKL1B) gene, a glucosidase-beta acid (GBA) gene, a chromosome 2 open reading frame 34 (C2orf34) gene, a transmembrane protein 167A (TMEM167A) gene, a microtubule associated serine/threonine kinase family member 4 (MAST4) gene, a N-acylsphingosine amidohydrolase (ASAH1) gene, a CGG triplet repeat binding protein 1 (CGGBP1) gene, a family with sequence similarity 175, member B (FAM175B) gene, a bridging integrator 1(BIN1) gene, a kruppel-like factor 12 (KLF12) gene, a methyltransferase like 7A (METTL7A) gene, a transmembrane protein 49 (TMEM49) gene, a ribosomal protein S6 kinase, 90 kDa polypeptide (RPS6KA5) gene, and a major histocompatibility complex, class II, DR beta (DR HLA-DRB1) gene.

3. The method of claim 1, wherein the test expression level of FK506 binding protein gene mRNA is about 79% or less of the mean expression level of FK506 binding protein gene mRNA in control blood samples from a population not predisposed to PTSD.

4. The method of claim 1, in which the expression level of mRNA is assessed using a nucleic acid amplification method that utilizes a primer that is specific for binding to a nucleotide sequence present in the mRNA and that is labeled so as to be detectable, or in which the expression level of mRNA is assessed using a method of binding mRNA that is labeled for detection to nucleic acids immobilized on a substrate.

5. The method of claim 4, in which the label is a fluorescent label or a radioactive label.

6. The method of claim 4, in which the FK506 bindin protein gene mRNA includes an exon junction in the FKBP5 gene.

7. The method of claim 6, in which the exon junction is one or more selected from the group consisting of the exon junction joining exons 4 and 5, the exon junction joining exons 7 and 8, the exon junction joining exons 8 and 9, the exon junction joining exons 11 and 12.

8. The method of claim 2, in which the expression level of said FK506 binding protein mRNA is less than the expression level of said FK506 binding protein mRNA in a population not predisposed to PTSD, and the expression level of the mRNA of the MAN2C1 gene or the product of the DDX17 gene is assessed and said expression level of the mRNA of the MAN2C1 gene or the mRNA of the DDX17 gene is greater than the mean expression level of said MAN2C1 or DDX17 mRNA in control samples from a population not predisposed to PTSD.

9. The method of claim 8, in which the expression level of the mRNA of the MAN2C1 gene or the mRNA of the DDX17 gene is assessed and said expression level of the mRNA of the MAN2C1 gene or of the DX17 gene is about 1.3times the mean expression level of said MAN2C1 or DDX17 mRNA in control samples from a population not predisposed to PTSD.

10. The method of claim 2, in which the expression levels of at least a FK506binding protein gene, a STAT5 gene and the expression level of mRNA of all three of said FK506 binding protein, STAT5 and NFIA genes are decreased compared to the mean expression level of said FK506 binding protein, STATS and NFIA mRNAs in control samples from a population not predisposed to PTSD.

11. The method of claim 1, further comprising assessment in said sample of the expression level of at least a second mRNA analyte species of a gene selected from the group of genes consisting of a CPNE1 gene, a TSC1 gene, a ADAM17 gene, a RNF181 gene, a MYO1C gene, a MOBKL1B gene, a GBA gene, a C2orf34 gene or a TMEM167A gene, and the expression level of said FK506 binding protein is about 79% compared to the mean expression level of said FK506 binding protein mRNA in control samples from a population not predisposed to PTSD, and the expression level of said second mRNA analyte species is from 80% to 87% compared to the mean expression level of said second mRNA analyte species in control samples from a population not predisposed to PTSD.

12. The method of claim 1, further comprising assessment in said sample of the expression level of at least a second mRNA analyte species of at least one gene selected from the group consisting of a MAST4 gene, an ASAH1 gene, a CGGBP1 gene, a FAM175B gene, a BIN1 gene, a KLF12 gene, a METTL7A gene, a TMEM49 gene and a PRS6KA5 gene is also assessed, and the mRNA expression level of said FK506 binding protein is about 79% compared to the mean mRNA expression level of said FK506 binding protein product in control samples from a population not predisposed to PTSD, and the expression level of second mRNA analyte is from 71% to 77 compared to the mean expression level of said second mRNA analyte in control samples from a population not predisposed to PTSD.

13. The method of claim 2, in which the FKBP5 gene has a coding sequence as shown in SEQ ID NO: 1, the STAT5B gene has a coding sequence as shown in SEQ ID NO: 2, the NF1A gene has a coding sequence as shown in SEQ ID NO: 3, the MAN2C1 gene has a coding sequence as shown in SEQ ID NO: 4; the DDX17 gene has a coding sequence as shown in SEQ ID NO: 5; the CPNE1 gene has a coding sequence as shown in SEQ ID NO: 6; the TSC1 gene has a coding sequence as shown in SEQ ID NO: 7; the ADAM17 gene has a coding sequence as shown in SEQ ID NO: 8; the RNF181 gene has a coding sequence as shown in SEQ ID NO: 9; the MYO1C gene has a coding sequence as shown in SEQ ID NO: 10; the MOBKL1B gene has a coding sequence as shown in SEQ ID NO: 11; the GBA gene has a coding sequence as shown in SEQ ID NO: 12; the C2orf34 gene has a coding sequence as shown in SEQ ID NO: 13; the TMEM167A gene has a coding sequence as shown in SEQ ID NO: 14; the MAST4 gene has a coding sequence as shown in SEQ ID NO: 15 or 16; the ASAH1 gene has a coding sequence as shown in SEQ ID NO: 17; the CGGBP1 gene has a coding sequence as shown in SEQ ID NO: 18, the FAM175B gene has a coding sequence as shown in SEQ ID NO: 19; the BIN1 gene has a coding sequence as shown in SEQ ID NO: 20; the KLF12 gene has a coding sequence as shown in SEQ ID NO: 21; the METTL7A gene has a coding sequence as shown in SEQ ID NO: 22; the TMEM49 gene has a coding sequence as shown in SEQ ID NO: 23; the RPS6KA5 gene has a coding sequence as shown in SEQ ID NO: 24; and the DR HLA-DRB1 gene has a coding sequence as shown in SEQ ID NO: 25, or said gene has a coding sequence that is at least 95% identical to said SEQ ID NO.

14. The method of claim 13, in which said gene has a coding sequence that is at least 98% identical to said SEQ ID NO.

15. The method of claim 1, in which the subject is treated by administration of a benzodiazepine compound or one or more selective serotonin reuptake inhibitors.

* * * * *